(12) United States Patent
Jacobson et al.

(10) Patent No.: US 8,871,208 B2
(45) Date of Patent: *Oct. 28, 2014

(54) 11-β-HYDROXYSTEROID DEHYDROGENASE TYPE 1 (11β-HSD1) INHIBITORS AND USES THEREOF

(75) Inventors: Peer B. Jacobson, Libertyville, IL (US); Lisa M. Olson, Hopkinton, MA (US); Sreeinvasarao Vepachedu, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/958,826

(22) Filed: Dec. 2, 2010

(65) Prior Publication Data
US 2011/0159005 A1 Jun. 30, 2011

Related U.S. Application Data

(60) Provisional application No. 61/266,581, filed on Dec. 4, 2009.

(51) Int. Cl.
| | |
|---|---|
| *A61K 31/00* | (2006.01) |
| *A61K 31/4184* | (2006.01) |
| *A61K 31/426* | (2006.01) |
| *A61K 31/433* | (2006.01) |
| *A61K 31/56* | (2006.01) |
| *A61K 45/06* | (2006.01) |
| *A61K 31/497* | (2006.01) |
| *A61K 31/35* | (2006.01) |

(52) U.S. Cl.
CPC ............... *A61K 31/00* (2013.01); *A61K 31/56* (2013.01); *A61K 31/433* (2013.01); *A61K 31/497* (2013.01); *A61K 45/06* (2013.01); *A61K 31/4184* (2013.01); *A61K 31/35* (2013.01); *A61K 31/426* (2013.01)
USPC .................... 424/158.1; 514/217.08; 514/343; 514/423; 514/616; 564/86; 564/155; 564/162

(58) Field of Classification Search
USPC ............... 514/217.08, 343, 423, 616; 564/86, 564/155, 162
See application file for complete search history.

(56) References Cited

U.S. PATENT DOCUMENTS 7,511,175 B2 * 3/2009 Patel et al. ....................... 564/86
7,737,137 B2 * 6/2010 Brune et al. ............. 514/217.08
7,855,308 B2 * 12/2010 Brune et al. .................. 564/155
7,880,001 B2 * 2/2011 Link et al. ..................... 544/360
2006/0074237 A1 4/2006 Amrein et al.
2009/0149503 A1 6/2009 Amrein et al.

OTHER PUBLICATIONS

Barf, T., et al. "Drugs of the Future," 2006, 31(3), pp. 231-243.
Hughes, K.A., et al., "Expert Opin. Investig. Drugs," 2008, 17(4), pp. 481-496.
Boyle, C.D., et al., "Expert Opin. Ther. Patents," 2009, 19(6), pp. 801-825.
Webster, S.P., et al., "Expert Opin. Ther. Patents," 2007, 17(12), pp. 1407-1422.
Boyle, C.D., et al., "Current Opinion in Drug Discovery & Development," 2008, 11(4), pp. 495-511.
Rew, Y., et al., "Bioorganic & Medicinal Chemistry Letters," 2009, 19, pp. 1797-1801.
Felson, et al., Arthritis Rheum., 38, pp. 727-735 (1995).
Alexander, et al., Brain Behav. Immun. 23(6), pp. 851-860, 2009.
Bennett, G.J., et al., Pain, 33(1), pp. 87-107 (1988).
Chaplan, S.R., et al., Journal of Neuroscience Methods, 53, pp. 55-63 (1994).
Dixon, W.J., Annu. Rev. Pharmacol. Toxicol., 20, pp. 441-462 (1980).
Kim, S.H., et al., Pain, 50(3), pp. 355-363 (1992).
Grennan, et al., Textbook of Pain, pp. 397-407 (1994).
Houge, et al., Ann. Pharmacother., (2002), 36, pp. 679-686.
McCarthy, et al., Textbook of Pain, pp. 387-395 (1994).
Felson, et al., Arthritis Rheum., 41, pp. 1564-1570 (1998).
Hardy, et al., Arthritis Res. Ther., 8, R108 (2006).
Cooper, et al., J. Bone Miner. Res. 16, pp. 1037-1044 (2001).
Buttgereit, et al., Annals of the Rheumatic Diseases, 67, pp. 1201-1203 (2008).
Chapman, et al., Ann. N.Y. Acad. Sci., 1088, pp. 265-273 (2006).
Crook, et al., Endocrine Abstracts, 13, P13 (2007).
Turner, et al., Calcif. Tissue Int., 54, pp. 311-315 (1995).
Lane, N.E., et al., Med. Pediatr. Oncol., 41, p. 212-216 (2003).
Bland, et al., J. Endocrinol., 161, pp. 455-464 (1999).
Cooper, et al., Bone, 23, pp. 119-125 (2000).
Cooper, et al., J. Bone Miner. Res., 17, pp. 979-986 (2002).
Cooper, et al., Bone, 27, pp. 375-381 (2000).
Walker, et al., J. of Clin. Endocrinology and Met., 80 pp. 3155-3159 (1995).
Hardy, et al., "Local and Systemic Gludocorticoid Metabolism in Inflammatory Arthritis", Annals of the Rheumatic Diseases, 2008, vol. 67, pp. 1204-1210.
International Search Report for Application No. PCT/US2010/058647 mailed on Aug. 17, 2011, 5 pages.

* cited by examiner

*Primary Examiner* — Kamal Saeed
(74) *Attorney, Agent, or Firm* — Lisa V. Mueller; Michael Best & Friedrich LLP

(57) ABSTRACT

A method for treating a patient suffering from inflammation, chronic inflammation, pain, rheumatoid arthritis (RA), osteoarthritis and osteoporosis, comprising administering an effective amount of a selective inhibitor of the 11-β-hydroxysteroid dehydrogenase Type 1 enzyme.

8 Claims, 2 Drawing Sheets

11-β-HYDROXYSTEROID DEHYDROGENASE TYPE 1 (11β-HSD1) INHIBITORS AND USES THEREOF

CROSS REFERENCE TO RELATED APPLICATIONS

This application claims priority from U.S. Provisional Application Ser. No. 61/266,581 filed Dec. 4, 2009, which is incorporated herein by reference.

TECHNICAL FIELD

The present disclosure relates to a treatment of inflammation, chronic inflammation, pain, rheumatoid arthritis (RA), osteoarthritis and osteoporosis using 11-β-hydroxysteroid dehydrogenase type 1 (11β-HSD1) inhibitors.

BACKGROUND

Rheumatoid arthritis (RA) is one of the most common chronic inflammatory conditions in developed countries and is a common cause of disability. RA is an autoimmune disease that causes chronic inflammation of the joints. RA can also cause inflammation of the tissue around the joints, as well as in other organs in the body. Autoimmune diseases are illnesses that occur when the body's tissues are mistakenly attacked by their own immune system. The immune system is a complex organization of cells and antibodies designed normally to "seek and destroy" invaders of the body, particularly infections. Patients with autoimmune diseases have antibodies in their blood that target their own body tissues, where they can be associated with inflammation. Because it can affect multiple other organs of the body, RA is considered a systemic illness. The exact etiology of RA is unknown, but current hypotheses suggest that both genetic and microbiological factors may be important (Grennan & Jayson, Textbook of Pain, 397-407 (1994)).

It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, Ann Pharmacother., 2002, 36, 679-686; McCarthy et al., Textbook of Pain, 387-395 (1994)). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

People with RA have a broad range of options for treatment, and doctors may try several RA medication combinations before they find the one that works best for a patient. RA medications include: corticosteroids, nonsteroidal anti-inflammatory drugs (NSAIDs), analgesics and disease modifying antirheumatic drugs (DMARDs).

Corticosteroids may reduce some joint damage by reducing inflammation, but their limited effectiveness and high rate of side effects do not make corticosteroids a good long-term treatment strategy. Corticosteroid medications can be given orally or injected directly into tissues and joints. They are more potent than NSAIDs in reducing inflammation and in restoring joint mobility and function. Corticosteroids are useful for short periods during severe flares of disease activity or when the disease is not responding to NSAIDs. However, corticosteroids can have serious side effects, especially when given in high doses for long periods of time. These side effects include weight gain, facial puffiness, thinning of the skin and bone, easy bruising, cataracts, risk of infection, muscle wasting, and destruction of large joints, such as the hips. Corticosteroids also carry some increased risk of contracting infections.

Prednisone is an oral, synthetic corticosteroid used for suppressing the immune system and inflammation. It has effects similar to other corticosteroids such as triamcinolone, methylprednisolone, prednisolone and dexamethasone. These synthetic corticosteroids mimic the action of cortisol (hydrocortisone), the naturally-occurring corticosteroid produced in the body by the adrenal glands. Corticosteroids have many effects on the body, but they most often are used for their potent anti-inflammatory effects, particularly in those conditions in which the immune system plays an important role. Such conditions include arthritis, colitis, asthma, bronchitis, certain skin rashes, and allergic or inflammatory conditions of the nose and eyes. Prednisone is inactive in the body and, in order to be effective, first must be converted to prednisolone by enzymes in the liver. Therefore, prednisone may not work as effectively in people with liver disease whose ability to convert prednisone to prednisolone is impaired. Side effects of prednisone and other corticosteroids range from mild annoyances to serious, irreversible damage, and they occur more frequently with higher doses and more prolonged treatment. Side effects include retention of sodium (salt) and fluid, weight gain, high blood pressure, loss of potassium, headache and muscle weakness. Prednisone also causes puffiness of the face (moon face), growth of facial hair, thinning and easy bruising of the skin, impaired wound healing, glaucoma, cataracts, ulcers in the stomach and duodenum, worsening of diabetes, irregular menses, rounding of the upper back ("buffalo hump"), obesity, retardation of growth in children, convulsions, and psychiatric disturbances. The psychiatric disturbances include depression, euphoria, insomnia, mood swings, personality changes, and even psychotic behavior.

NSAIDs relieve symptoms and mild inflammation but do not have any modifying effect on the disease itself. Acetylsalicylate, naproxen, ibuprofen, and etodolac are examples of NSAIDs. NSAIDs are medications that can reduce tissue inflammation, pain, and swelling. The newer NSAIDs are effective in reducing inflammation and pain requiring fewer dosages per day. Patients' responses to different NSAID medications vary. The most common side effects of aspirin and other NSAIDs include stomach upset, abdominal pain, ulcers, and even gastrointestinal bleeding. Additional medications are frequently recommended to protect the stomach from the ulcer effects of NSAIDs. These medications include antacids, sucralfate, proton-pump inhibitors, and misoprostol. Newer NSAIDs include selective Cox-2 inhibitors, such as celecoxib, which offer antiinflammatory effects with less risk of stomach irritation and bleeding risk. Analgesics include creams (capsaicin) or pain medication pills such as propoxyphene or oxycodone.

DMARDs can slow, and sometimes even prevent, joint damage, and destruction associated with rheumatoid arthritis. They include leflunomide, sulfasalazine, hydroxychloroquine, and methotrexate. Methotrexate is the most commonly prescribed first-line treatment for RA because it provides quick relief and has a relatively low rate of side effects. Biologic DMARDs are a newer group of drugs derived from living organisms. These medications block various elements of the immune system that can fuel inflammation. They include medications etanercept, infliximab, anakinra, adalimumab, rituximab and abatacept.

Etanercept, infliximab, and adalimumab are biologic medications that intercept a messenger protein in the joints called tumor necrosis factor (TNF) that promotes inflammation of the joints in RA. These TNF-blockers intercept TNF before it can act on its natural receptor to "switch on" inflammation. This effectively blocks the TNF inflammation messenger from recruiting the cells of inflammation. Symptoms can be significantly, and often rapidly, improved in patients using these drugs. Etanercept must be injected subcutaneously once or twice a week. Infliximab is given by infusion directly into a vein (intravenously). Adalimumab is injected subcutaneously either every other week or weekly. Each of these medications is being evaluated by doctors in practice to determine what role they may have in treating patients in various stages of rheumatoid arthritis. Research has shown that biological response modifiers also prevent the progressive joint destruction of rheumatoid arthritis. They are currently recommended for use after other second-line medications have not been effective. The biological response modifiers (TNF-inhibitors) are expensive treatments. They are also frequently used in combination with methotrexate and other DMARDs, because the TNF-blocking biologics are more effective when combined with methotrexate.

Anakinra is another biologic treatment that is used to treat moderate to severe rheumatoid arthritis. Anakinra works by binding to a cell messenger protein (IL-1, a proinflammation cytokine). Anakinra is injected under the skin daily. Anakinra can be used alone or with other DMARDs. The response rate of anakinra does not seem to be as high as with other biologic medications. Rituximab is an antibody that was first used to treat lymphoma, a cancer of the lymph nodes. Rituximab can be effective in treating autoimmune diseases like RA because it depletes B-cells, which are important cells of inflammation and in producing abnormal antibodies that are common in these conditions. Rituximab is now available to treat moderate to severely active RA in patients who have failed treatment with the TNF-blocking biologics. Preliminary studies have shown that rituximab was also found to be beneficial in treating severe RA complicated by blood vessel inflammation (vasculitis) and cryoglobulinemia. Abatacept is a biologic medication that blocks T-cell activation to treat adult patients who have failed treatment with a traditional DMARD or TNF-blocking biologic medication.

Glycyrrhetinic acid, a non-selective inhibitor of both 11β-hydroxysteroid dehydrogenase type 1 and 2 isozymes (11β-HSD-1 and 11β-HSD-2), has been identified as a possible drug for RA (International Publication WO2005/027882). However, inhibition of 11β-HSD-2 causes serious side effects, such as hypertension.

11β-HSD-1 is a low affinity enzyme with $K_m$ for cortisone in the micromolar range that prefers NADPH/NADP$^+$ (nicotinamide adenine dinucleotide phosphate) as cofactors. 11β-HSD-1 is widely expressed and particularly high expression levels are found in liver, brain, lung, adipose tissue, bone and vascular smooth muscle cells. Many studies have shown that 11β-HSD-1 functions primarily as a reductase in vivo and in intact cells. It converts inactive 11-ketoglucocorticoids (i.e., cortisone or dehydrocorticosterone) to active 11-hydroxyglucocorticoids (i.e., cortisol or corticosterone), and thereby amplifies glucocorticoid action in a tissue-specific manner.

The present application describes the utility of the selective inhibitors of 11β-HSD-1 in the treatment of inflammation, chronic inflammation, pain, RA, osteoarthritis and osteoporosis.

SUMMARY OF THE INVENTION

Figure 1:
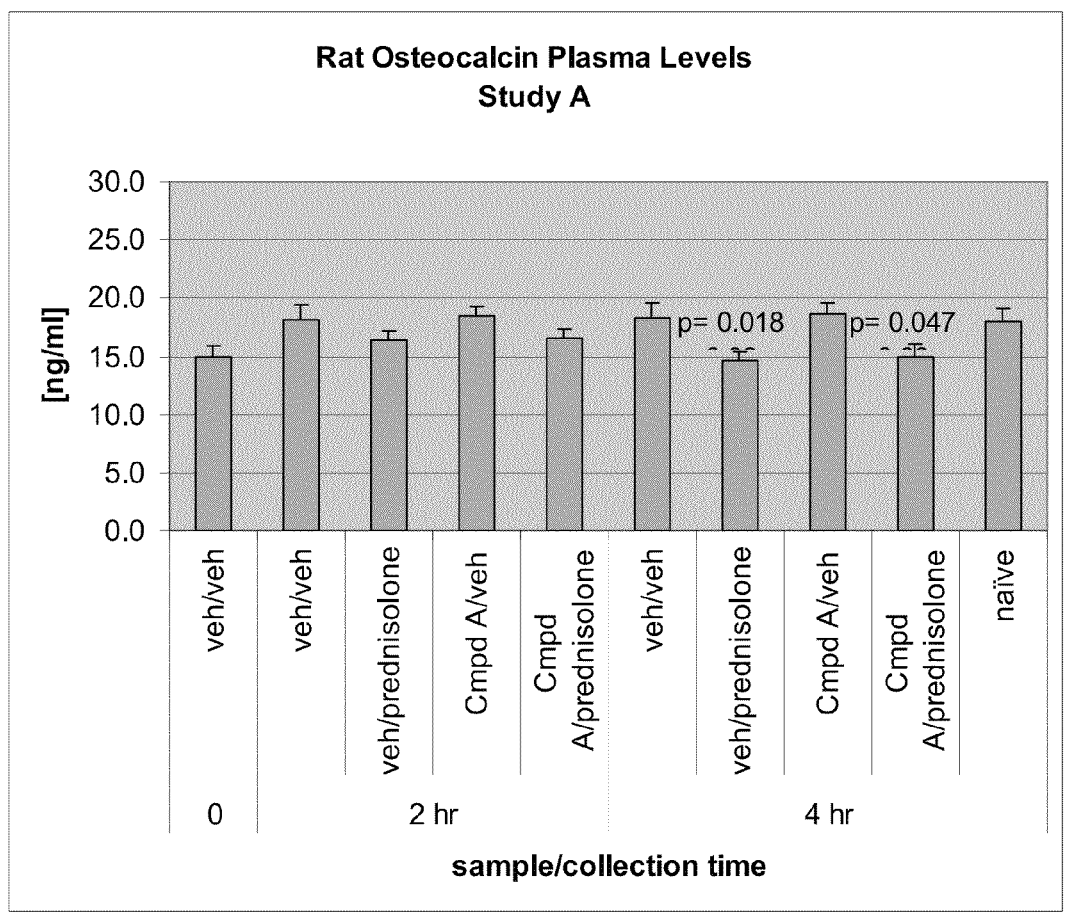
FIG. 1 shows the results of study A where rats were pre-dosed with compound A-801195 (Compound A) at 30 mg/kg 1 hour prior to administration with the active glucocorticoid, prednisolone, at 10 mg/kg, po. At 2 and 4 hours after dosing prednisolone, rats were sacrificed, and blood evaluated for levels of osteocalcin. Since prednisolone is the active glucocorticoid, and is not generated via 11β-HSD-1, it was expected that Compound A would have no effect on osteocalcin reduction as shown in this FIG. 1. At the 4 hour time point, rats pre-treated with vehicle or prednisolone had significant reductions in plasma osteocalcin.

One embodiment is directed to a method of treating inflammation, chronic inflammation, pain, RA, osteoarthritis and osteoporosis, comprising administering a compound of formula (I)

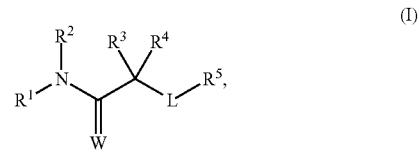

wherein
L is —(CH$_2$)$_n$—, or —(CH$_2$)$_m$—X—(CH$_2$)$_n$—;
m is 0, 1, or 2;
n is independently at each occurrence 0, 1, or 2;
R$^1$ is cycloalkyl or heterocycle;
R$^2$ is hydrogen, alkyl, or aryl; or R$^2$ and R$^3$ together with the atoms to which they are attached form a heterocycle;
R$^3$ and R$^4$ are independently hydrogen or alkyl; or R$^3$ and R$^4$ together with the atom to which they are attached form a cycloalkyl or heterocycle;
R$^5$ is hydrogen, alkyl, amino, aryl, cycloalkyl, heteroaryl, or heterocycle; or R$^4$ and R$^5$ together with the atoms to which they are attached form a cycloalkyl or heterocycle;
X is —O—, —S—, —S(O)—, —S(O)$_2$—, —NR$^{36}$—, or —CR$^{36}$R$^{37}$—;
R$^{36}$ and R$^{37}$ are independently at each occurrence hydrogen or alkyl; or R$^{36}$ and R$^2$ together with the atoms to which they are attached form a heterocycle;
W is N—CN, N—OR$^6$, N—R$^6$, O, or S; and
R$^6$ is hydrogen, alkyl or aryl; or
a pharmaceutically acceptable salt, ester, amide, or prodrug thereof.

Another embodiment is directed to a pharmaceutical composition comprising a compound of formula (I), wherein the compound of formula (I) shows an IC$_{50}$ value less than 100 nM, and a pharmaceutically acceptable carrier to treat inflammation, chronic inflammation, pain, RA, osteoarthritis and osteoporosis.

DETAILED DESCRIPTION OF THE INVENTION

Definition of Terms

For a variable that occurs more than one time in any substituent or in the compound of the disclosure or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

As used throughout this specification and the appended claims, the following terms have the following meanings:

The term "acetyl" means a —C(O)CH$_3$ group.

The term "acyl" means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" means an acyl group, as defined herein, appended to the parent molecular moiety through an oxygen atom. Representative examples of acyloxy include, but are not limited to, acetyloxy, propionyloxy, and isobutyryloxy.

The term "alkenyl" means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, hexyloxy and the like.

The term "alkoxyalkoxy" means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" means an alkoxy group, as defined herein, appended to the parent molecular moiety through a —C(=NH)— group, which also is defined as an imino group. Representative examples of alkoxyimino include, but are not limited to, imino(methoxy)methyl, ethoxy(imino)methyl and tert-butoxy(imino)methyl.

The term "alkoxysulfonyl" means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

In some instances, the number of carbon atoms in a hydrocarbyl substituent (e.g., alkyl, alkenyl, alkynyl, or cycloalkyl) is indicated by the prefix "$C_x$—$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "alkyl-NH-alkyl" refers to an alkyl group, as defined herein, appended to a second alkyl group, as defined herein through an —NH— group. Said second alkyl group is appended to the parent molecular moiety.

The term "alkylcarbonyl" refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcycloalkyl" means an alkyl group, as defined herein, appended to the parent molecular moiety through a cycloalkyl group, as defined herein. Representative examples of alkylcycloalkyl include, but are not limited to, 4-ethylcyclohexyl, 3-methylcyclopentyl, and 2-isopropylcyclopropyl.

The term "alkylsulfonyl" means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" means an alkyl group, as defined herein, appended to the parent molecular moiety through a sulfur atom. Representative examples of alkylthio include, but are not limited, methylthio, ethylthio, tert-butylthio, and hexylthio.

The term "amino" is —NR$^{90}$R$^{91}$, wherein R$^{90}$ and R$^{91}$ are each independently hydrogen, alkyl, alkoxy, alkylsulfonyl, aryl, arylalkyl, aryloxy, aryloxyalkyl, arylsulfonyl, alkyl-NH-alkyl, aryl-NH-alkyl, arylalkyl, haloalkyl, aryl-heterocycle, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocycle-NH-alkyl, heterocyclealkyl, heterocycle-heterocycle, heterocycleoxyalkyl, heterocycleoxy, heterocyclesulfonyl, or hydroxyl.

The term "alkynyl" means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "American College of Rheumatology (ACR) response" is a standard assessment used to measure patients' responses to anti-rheumatic therapies, devised by the ACR, which includes changes in number of swollen joints, tender joints, physician global assessment of disease, patient global assessment of disease, patient assessment of pain, C-reactive protein or erythrocyte sedimentation rate, and health assessment questionnaire (HAQ) score (Felson et al., *Arthritis Rheum.*, 41, 1564-1570 (1998)).

An ACR 20 response requires a patient to have a 20% reduction in the number of swollen and tender joints, and a reduction of 20% in three of the following five parameters: physician global assessment of disease, patient global assessment of disease, patient assessment of pain, C-reactive protein or erythrocyte sedimentation rate, and degree of disability in HAQ score.

An ACR 50 response requires a patient to have a 50% reduction in the number of swollen and tender joints, and a reduction of 50% in three of the following five parameters: physician global assessment of disease, patient global assessment of disease, patient assessment of pain, C-reactive protein or erythrocyte sedimentation rate, and degree of disability in HAQ score.

An ACR 70 response requires a patient to have a 70% reduction in the number of swollen and tender joints, and a reduction of 70% in three of the following five parameters: physician global assessment of disease, patient global assessment of disease, patient assessment of pain, C-reactive protein or erythrocyte sedimentation rate, and degree of disability in HAQ score.

The term "amido" means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "aryl" means phenyl, a bicyclic aryl, or a tricyclic aryl. The bicyclic aryl is naphthyl, a phenyl fused to a cycloalkyl, cycloalkenyl, heteroaryl or heterocycle, as defined herein. The bicyclic aryl must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. Tricyclic fused ring systems are exemplified by a bicyclic aryl, as defined herein, and fused to a cycloalkyl, phenyl, heteroaryl, or heterocycle, as defined herein. The tricyclic aryl is attached to the parent molecular moiety through any carbon atom contained within a phenyl ring. Representative examples of aryl include, but are not limited to, anthracenyl, phenanthrenyl, azulenyl, fluorenyl, indanyl, indenyl, naphthyl, phenyl and tetrahydronaphthyl.

The aryl groups of this disclosure may be substituted with 0, 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylsulfonyl, alkynyl, aryl, arylalkoxy, arylcarbonyl, aryloxy, arylsulfonyl, carboxy, carboxyalkyl, cyano, cyanoalkyl, ethylenedioxy, formyl, haloalkoxy, haloalkyl, halogen, heteroaryl, heteroarylalkyl, heteroarylcarbonyl, heterocycle, heterocyclecarbonyl, heterocycleoxy, heterocyclesulfonyl, hydroxy, hydroxyalkyl, nitro, $R_fR_gN$—, $R_fR_g$Nalkyl, $R_fR_g$Ncarbonyl, —N(H)C(O)N(H)(alkyl), and $R_fR_g$Nsulfonyl, wherein $R_f$ and $R_g$ are independently selected from the group consisting of hydrogen, alkyl, alkoxyalkyl, alkoxycarbonyl, alkylcarbonyl, alkylsulfonyl, cycloalkyl, haloalkyl, haloalkylcarbonyl and cycloalkylalkyl wherein the cycloalkyl, the cycloalkyl of cycloalkylalkyl as represented by $R_f$ and $R_g$ are each independently unsubstituted or substituted with 1, 2 or 3 substituents independently selected from the group consisting of halogen, alkyl and haloalkyl. The substituent aryl, the aryl of arylalkoxy, the aryl of arylcarbonyl, the aryl of aryloxy, the aryl of arylsulfonyl, the substituent heteroaryl, the heteroaryl of heteroarylalkyl, the heteroaryl of heteroarylcarbonyl, the substituent heterocycle, the heterocycle of heterocyclecarbonyl, the heterocycle of heterocycleoxy, the heterocycle of heterocyclesulfonyl may be optionally substituted with 1, 2 or 3 substituents independently selected from the group consisting of alkoxy, alkoxyalkyl, alkoxycarbonyl, alkyl, alkylcarbonyl, alkynyl, carboxy, carboxyalkyl, cyano, haloalkyl, halogen, hydroxy, hydroxyalkyl, nitro, $R_fR_gN$—, $R_fR_g$Nalkyl, $R_fR_g$Ncarbonyl and $R_fR_g$Nsulfonyl wherein $R_f$ and $R_g$ are as described herein.

The term "arylalkyl" means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "arylcarbonyl" means an aryl group, as defined herein, appended to the parent molecular moiety through a carbonyl group, as defined herein. Representative examples of arylcarbonyl include, but are not limited to, benzoyl and naphthoyl.

The term "aryloxy" means an aryl group, as defined herein, appended to the parent molecular moiety through an oxygen atom. Representative examples of aryloxy include, but are not limited to, phenoxy and tolyloxy.

The term "aryloxyalkyl" refers to an aryloxy group, as defined herein, appended to the parent molecular moiety through an alkyl group, as defined herein.

The term "arylsulfonyl" refers to an aryl group, as defined herein, appended to the parent molecular moiety through a sulfonyl group, as defined herein. Representative examples of arylsulfonyl include, but are not limited to, phenylsulfonyl, 4-bromophenylsulfonyl and naphthylsulfonyl.

The term "carbonyl" means a —C(O)— group.

The term "carboxy" means a —CO$_2$H group.

The term "carboxyalkyl" means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "carboxycycloalkyl" as used herein refers to a carboxy group as defined herein, appended to the parent molecular moiety through a cycloalkyl group as defined herein.

The term "combination therapy" is defined as the administration of a single pharmaceutical dosage formulation, which comprises two or more therapeutic agents.

The term "cyano" means a —CN group, attached to the parent molecular moiety through the carbon.

The term "cyanoalkyl" means a —CN group attached to the parent molecular moiety through an alkyl group. Representative examples of "cyanoalkyl" include, but are not limited to, 3-cyanopropyl, and 4-cyanobutyl.

The term "cycloalkoxy" means a cycloalkyl group, as defined herein, appended to the parent molecular moiety through an oxygen atom. Representative examples of cycloalkoxy include, but are not limited to, cyclohexyloxy and cyclopropoxy.

The term "cycloalkoxyalkyl" means a cycloalkoxy group, as defined herein, appended to the parent molecular moiety through an alkyl group, wherein alkyl is as defined herein. Representative examples of cycloalkoxylalkyl include, but are not limited to, cyclobutoxymethyl, cyclopentyloxymethyl, 2-(cyclopentyloxy)ethyl and cyclohexyloxymethyl.

The term "cycloalkyl" means a monocyclic, bicyclic, or tricyclic ring system. Monocyclic ring systems are exemplified by a saturated cyclic hydrocarbon group containing from 3 to 4 carbon atoms (($C_3$-$C_4$)cycloalkyl), 5 to 6 carbon atoms (($C_5$-$C_6$)cycloalkyl), 3 to 6 carbon atoms (($C_3$-$C_6$)cycloalkyl), from 7 to 8 carbon atoms (($C_7$-$C_8$)cycloalkyl), or from 3 to 8 carbon atoms (($C_3$-$C_8$)cycloalkyl). Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptanyl, bicyclo[2.2.1]heptanyl, bicyclo[2.2.2]octanyl, bicyclo[3.2.2]nonanyl, bicyclo[3.3.1]nonanyl, and bicyclo[4.2.1]nonanyl. Bicyclic ring systems are also exemplified by a monocyclic ring system fused to a phenyl or heteroaryl ring. Representative examples of bicyclic ring systems include, but are not limited to, 1,2,3,4-tetrahydronaphthalenyl, indanyl, and 6,7-dihydro-5H-cyclopenta[c]pyridinyl. The bicyclic cycloalkyl is connected to the parent molecular moiety through any carbon atom contained within the unsaturated cycloalkyl ring. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonanyl and tricyclo[3.3.1.1$^{3,7}$]decanyl(adamantanyl).

The cycloalkyl groups of the present disclosure are substituted with 0, 1, 2, 3 or 4 substituents selected from the group consisting of alkyl, alkenyl, alkyl-NH-alkyl, alkylcarbonyl, alkylsulfonyl, cyano, cyanoalkyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, —NO$_2$, —NR$^8$—[C(R$^9$R$^{10}$)]$_p$C(O)—R$^{11}$, —[C(R$^{12}$R$^{13}$)$_q$]—C(O)—R$^{14}$, —[C(R$^{12}$R$^{13}$)]$_q$—S(O)$_2$—R$^{14}$, —O—[C(R$^{12}$R$^{13}$)]$_q$—C(O)—R$^{14}$, —OR$^{15}$, —N(R$^{16}$R$^{17}$), —CO$_2$R$^{18}$, —C(O)—N(R$^{19}$R$^{20}$), —C(R$^{21}$R$^{22}$)—OR$^{23}$, and —C(R$^{24}$R$^{25}$)—N(R$^{26}$R$^{27}$), —C(=NOH)—N(H)$_2$, —C(R$^{28}$R$^{29}$)—C(O)N(R$^{30}$R$^{31}$), —S(O)$_2$—N(R$^{32}$R$^{33}$), and —C(R$^{28}$R$^{29}$)—S(O)$_2$—N(R$^{32}$R$^{33}$), wherein p is 1, 2, 3, 4, 5 or 6;

q is 0, 1, 2, 3, 4, 5 or 6;

R$^8$ is hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, or heterocycleoxyalkyl;

R$^9$ and R$^{10}$ are each independently hydrogen, alkyl, carboxy, carboxyalkyl, cycloalkyl, carboxycycloalkyl, aryl, arylalkyl, aryloxyalkyl, heterocycle, heterocyclealkyl, or heterocycleoxyalkyl, or R$^9$ and R$^{10}$ together with the atom to which they are attached form cycloalkyl or heterocycle;

R$^{11}$ is hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, or —N(R$^{28}$R$^{29}$);

R$^{12}$ and R$^{13}$ are each independently hydrogen, alkyl, carboxy, carboxyalkyl, cycloalkyl, carboxycycloalkyl, aryl, arylalkyl, aryloxyalkyl, heterocycle, heterocyclealkyl, or heterocycleoxyalkyl, or R$^{12}$ and R$^{13}$ together with the atom to which they are attached form cycloalkyl or heterocycle;

R$^{14}$ is hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, or —N(R$^{30}$R$^{31}$);

R$^{15}$ is hydrogen, alkyl, alkylcarbonyl, carboxyalkyl, cycloalkyl, carboxycycloalkyl, aryl, arylalkyl, aryloxyalkyl, haloalkyl, heterocycle, heterocyclealkyl, or heterocycleoxyalkyl;

R$^{16}$ and R$^{17}$ are each independently hydrogen, alkyl, alkylcarbonyl, carboxyalkyl, cycloalkyl, carboxycycloalkyl, aryl, arylalkyl, aryloxyalkyl, haloalkyl, heterocycle, heterocyclealkyl, heterocycleoxyalkyl, alkylsulfonyl, cycloalkylsulfonyl, arylsulfonyl, or heterocyclesulfonyl, or R$^{16}$ and R$^{17}$ together with the atom to which they are attached form a heterocycle;

R$^{18}$ is hydrogen, alkyl, carboxyalkyl, cycloalkyl, carboxycycloalkyl, aryl, arylalkyl, aryloxyalkyl, heterocycle, heterocyclealkyl, or heterocycleoxyalkyl;

R$^{19}$ and R$^{20}$ are each independently hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, or heterocyclesulfonyl, or R$^{19}$ and R$^{20}$ together with the atom to which they are attached form a heterocycle;

R$^{21}$, R$^{22}$ and R$^{23}$ are each independently hydrogen, alkyl, carboxyalkyl, carboxycycloalkyl, cycloalkyl, haloalkyl, aryl, or heterocycle;

R$^{24}$ and R$^{25}$ are each independently hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, or heterocycle;

R$^{26}$ and R$^{27}$ are each independently hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, or heterocycle, or R$^{26}$ and R$^{27}$ together with the atom to which they are attached form a heterocycle;

R$^{28}$ and R$^{29}$ are each independently at each occurrence hydrogen or alkyl;

R$^{30}$ and R$^{31}$ are each independently at each occurrence hydrogen, alkyl, alkylcarbonyl, alkoxy; alkylsulfonyl, aryl, arylcarbonyl, aryloxy, arylsulfonyl, carboxyalkyl, carboxycycloalkyl, cycloalkyl, cycloalkylcarbonyl, cycloalkyloxy, cycloalkylsulfonyl, heteroaryl, heteroarylcarbonyl, heteroaryloxy, heteroarylsulfonyl, heterocycle, heterocyclecarbonyl, heterocycleoxy, heterocyclesulfonyl, or hydroxy, or R$^{30}$ and R$^{31}$ taken together with the atom to which they are attached form heteroaryl or heterocycle; and R$^{32}$ and R$^{33}$ are each independently at each occurrence selected from the group consisting of hydrogen, alkyl, alkoxy, alkylsulfonyl, aryl, arylalkyl, aryloxy, aryloxyalkyl, arylsulfonyl, alkyl-NH-alkyl, aryl-NH-alkyl, arylalkyl, haloalkyl, aryl-heterocycle, carboxy, carboxyalkyl, carboxycycloalkyl, cycloalkyl, cycloalkyloxy, cycloalkylsulfonyl, heteroaryl, heteroarylalkyl, heteroaryloxyalkyl, heteroaryloxy, heteroarylsulfonyl, heterocycle, heterocycle-NH-alkyl, heterocyclealkyl, heterocycle-heterocycle, heterocycleoxyalkyl, heterocycleoxy, heterocyclesulfonyl, and hydroxy, or R$^{32}$ and R$^{33}$ taken together with the atom to which they are attached form a heterocycle.

The term "cycloalkylalkyl" means a cycloalkyl group, as defined herein, appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl.

The term "cycloalkylcarbonyl" means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "cycloalkylsulfonyl" refers to cycloalkyl group, as defined herein, appended to the parent molecular moiety through a sulfonyl group, as defined herein. Representative examples of cycloalkylsulfonyl include, but are not limited to, cyclohexylsulfonyl and cyclobutylsulfonyl.

The term "formyl" means a —C(O)H group.

The term "halo" or "halogen" means —Cl, —Br, —I or —F.

The term "haloalkoxy" means at least one halogen, as defined herein, appended to the parent molecular moiety through an alkoxy group, as defined herein. Representative examples of haloalkoxy include, but are not limited to, fluoroalkoxy, chloroalkoxy, bromoalkoxy and iodoalkoxy, such as fluoromethoxy, difluoromethoxy, trifluoromethoxy, 2-fluoroethoxy, trifluoromethoxy, 2,2,2-trifluoroethoxy, and pentafluoroethoxy.

The term "haloalkyl" means at least one halogen, as defined herein, appended to the parent molecular moiety through an alkyl group, as defined herein. Representative examples of haloalkyl include, but are not limited to, difluoromethyl, chloromethyl, 2-fluoroethyl, trifluoromethyl, 2,2,2-trifluoroethyl, pentafluoroethyl, and 2-chloro-3-fluoropentyl.

The term "halocycloalkyl" means at least one halogen, as defined herein, appended to the parent molecular moiety through a cycloalkyl group, as defined herein. Representative examples of halocycloalkyl include, but are not limited to, fluorocyclohexyl, bromocyclopropyl, and trans-2,3-dichlorocyclopentyl.

The term "halocycloalkylalkyl" means a halocycloalkyl group as defined herein, attached to the parent molecular moiety through an alkyl group. Representative examples of halocycloalkylalkyl include, but are not limited to, (4-fluorocyclohexyl)methyl, (2,2-difluorocyclobutyl)methyl and the like.

The term "halothioalkoxy" means at least one halogen, as defined herein, appended to the parent molecular moiety through a thioalkoxy group, as defined herein. Representative examples of halothioalkoxy include, but are not limited to, 2-chloroethylsulfane and trifluoromethylsulfane.

The term "heteroaryl" means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, 1H-pyrrolo[2,3-b]pyridinyl, quinolinyl, quinoxalinyl and thienopyridinyl.

The heteroaryl groups are optionally substituted with 1, 2, 3 or 4 substituents independently selected from the group consisting of acyloxy, alkenyl, alkoxy, alkoxycarbonyl, alkyl, alkylcarbonyl, alkylsulfonyl, alkylthio, alkynyl, amido, aryl, aryloxy, carboxy, carboxyalkyl, cyano, cyanoalkyl, cycloalkyl, cycloalkoxy, formyl, haloalkoxy, haloalkyl, halogen, halothioalkoxy, thioalkoxy, thiocycloalkoxy, thioaryloxy, nitro, and —NR$^{96}$R$^{97}$, wherein R$^{96}$ and R$^{97}$ are independently hydrogen, alkoxyalkyl, alkoxycarbonyl, alkyl, alkylcarbonyl, alkylsulfonyl, aryl, cycloalkyl, haloalkyl, heteroaryl, or heterocycle.

The term "heteroarylalkyl" means a heteroaryl, as defined herein, appended to the parent molecular moiety through an alkyl group, as defined herein.

The term "heterocycle" or "heterocyclic" means a monocyclic heterocycle, a bicyclic heterocycle, or tricyclic heterocycle. The monocyclic heterocycle is a 3, 4, 5, 6 or 7 membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring contains zero, one, or two double bonds provided that the ring, when taken together with a substituent, does not tautomerize with a substituent to form an aromatic ring and one, two, three, or four heteroatoms selected from the group consisting of O, N and S. The monocyclic heterocycle is connected to the parent molecular moiety through any carbon atom or any nitrogen atom contained within the monocyclic heterocycle.

Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, hexahydropyrrolo[3,4-b]pyrrol-1(2H)-yl, tetrahydro-1H-pyrrolo[3,4-b]pyridin-6(2H,7H,7aH)-yl, 3-azabicyclo[3.2.0]heptane and 1,2,3,4-tetrahydroquinolinyl. Representative examples of tricyclic heterocyclic systems include, but are not limited to, aza-adamantanyl and oxa-adamantanyl.

The heterocycles are substituted with hydrogen, or substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, aryl, carboxy, cyano, cyanoalkyl, cycloalkyl, formyl, haloalkoxy, haloalkyl, halogen, heteroaryl, hydroxy, hydroxyalkyl, mercapto, nitro, oxo, —NR$^{98}$R$^{99}$, (NR$^{98}$R$^{99}$)carbonyl, —SO$_2$N(R$^{98}$)(R$^{99}$), —NR$^{98}$(C=O)NR$^{98}$R$^{99}$, —NR$^{98}$(C=O)Oalkyl, and —N(R$^{98}$)SO$_2$(R$^{99}$), wherein R$^{98}$ and R$^{99}$ each are each independently selected from the group consisting of acyl, alkoxyalkyl, alkoxycarbonyl, alkyl, alkylcarbonyl, alkylcycloalkyl, alkylsulfonyl, amido, aryl, cyanoalkyl, cycloalkoxyalkyl, cycloalkyl, haloalkyl, halocycloalkyl, halocycloalkylalkyl, heteroaryl, heterocycle, hydrogen, formyl, hydroxy, and hydroxyalkyl.

The term "heterocyclealkyl" means a heterocycle, as defined herein, appended to the parent molecular moiety through an alkyl group, as defined herein. Representative examples of heterocyclealkyl include, but are not limited, (pyrrolidin-2-yl)methyl, 2-(morpholin-4-yl)ethyl, and (tetrahydrofuran-3-yl)methyl.

The term "heterocyclecarbonyl" refers to a heterocycle, as defined herein, appended to the parent molecular moiety through a carbonyl group, as defined herein. Representative examples of heterocyclecarbonyl include, but are not limited to, 1-piperidinylcarbonyl, 4-morpholinylcarbonyl, pyridin-3-ylcarbonyl and quinolin-3-ylcarbonyl.

The term "heterocycle-heterocycle" means a heterocycle, as defined herein, appended to the parent molecular moiety through a second heterocycle, as defined herein.

The term "heterocycleoxyalkyl" refers to a heterocycle-oxy, as defined herein, appended to the parent molecular moiety through an alkyl group, as defined herein.

The term "heterocyclesulfonyl" refers to a heterocycle, as defined herein, appended to the parent molecular moiety through a sulfonyl group, as defined herein. Representative examples of heterocyclesulfonyl include, but are not limited to, 1-piperidinylsulfonyl, 4-morpholinylsulfonyl, pyridin-3-ylsulfonyl and quinolin-3-ylsulfonyl.

The term "hydroxy" or "hydroxyl" means an —OH group.

The term "hydroxyalkyl" means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "imino" means a —C(=NH)— group.

The term "mercapto" means a —SH group.

The term "multivalent binding protein" denotes a binding protein comprising two or more antigen binding sites. The multivalent binding protein is preferably engineered to have three or more antigen binding sites, and is generally not a naturally occurring antibody. The term "multispecific binding protein" refers to a binding protein capable of binding two or more related or unrelated targets. Binding proteins that comprise two or more antigen binding sites and are tetravalent or multivalent binding proteins are known as dual variable domain (DVD) binding proteins. Such DVDs may be monospecific, i.e capable of binding one antigen or multispecific, i.e. capable of binding two or more antigens. DVD binding proteins comprising two heavy chain DVD polypeptides and two light chain DVD polypeptides are referred to a DVD-Ig. Each half of a DVD-Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. Pat. No. 7,612,181.

The term "nitro" means a —NO$_2$ group.

The term "oxo" means (=O).

The term "pain" includes neuropathic pain and mixed pain. Neuropathic pain includes central neuropathic pain and peripheral neuropathic pain. Mixed pain includes osteoarthritic pain, pain resulting from a migraine, chronic lower-back pain, and pain associated with fibromyalgia.

The term "parenterally" refers to modes of administration, including intravenous, intramuscular, intraperitoneal, intrasternal, subcutaneous, intraarticular injection and infusion.

The term "pharmaceutically acceptable salt" or "salt" refers to those salts which are, within the scope of sound medical judgment, suitable for use in contact with the tissues of humans and lower animals without undue toxicity, irritation, allergic response, and the like, and are commensurate with a reasonable benefit/risk ratio and effective for their intended use. Pharmaceutically acceptable salts are well-known in the art. The salts can be prepared in situ during the final isolation and purification of the compounds of the disclosure or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid. Basic addition salts can be prepared in situ during the final isolation and purification of compounds of this disclosure by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediammonium, ethanolammonium, diethanolammonium, piperidinium, and piperazinium.

The term "pharmaceutically acceptable ester" or "ester" refers to esters of compounds of the disclosure which hydrolyze in vivo and include those that break down readily in the human body to leave the parent compound or a salt thereof. Examples of pharmaceutically acceptable, non-toxic esters of the disclosure include, but are not limited to, $C_1$-$C_6$ alkyl esters and $C_5$-$C_7$ cycloalkyl esters. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" or "amide" refers to non-toxic amides of the disclosure derived from ammonia, primary $C_1$-$C_3$ alkyl amines, primary $C_4$-$C_6$ alkyl amines, secondary $C_1$-$C_2$ dialkyl amines and secondary $C_3$-$C_6$ dialkyl amines. In the case of secondary amines, the amine can also be in the form of a 5- or 6-membered heterocycle containing one nitrogen atom. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the disclosure in the form of a pharmaceutically acceptable prodrug.

The term "pharmaceutically acceptable prodrug" or "prodrug" represents those prodrugs of the compounds of the disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the disclosure can be rapidly transformed in vivo to a parent compound of formula (I), for example, by hydrolysis. A thorough discussion is provided in Higuchi et al., Prodrugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "pharmaceutically acceptable carrier" or "carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The term "sulfonyl" means a —$SO_2$— group.

The phrase "therapeutically effective amount" means a sufficient amount of the compound to treat disorders, at a reasonable benefit/risk ratio applicable to any medical treatment.

The term "therapeutically suitable excipient" generally refers to pharmaceutically suitable, solid, semi-solid or liquid fillers, diluents, encapsulating material, formulation auxiliary and the like.

The term "therapeutically suitable metabolite" generally refers to a pharmaceutically active compound formed by the in vivo biotransformation of compounds of formula I.

The term "thioalkoxy" refers to an alkyl group, as defined herein, appended to the parent molecular moiety through a sulfur atom. Representative examples of thioalkoxy include, but are not limited to, methylthio, ethylthio, tert-butylthio, and hexylthio.

The term "thiocyloalkoxy" refers to a cycloalkyl group, as defined herein, appended to the parent molecular moiety through a sulfur atom. Representative examples of thiocycloalkoxy include, but are not limited to, cyclopentylsulfane and cyclohexylsulfane.

The term "thioaryloxy" means an aryl group, as defined herein, appended to the parent molecular moiety through a sulfur atom. Representative examples of thioaryloxy include, but are not limited to, thiophenoxy and tolylsulfane.

Methods of the Invention

It has been shown that synovial fibroblasts express 11β-HSD1 in vitro and in vivo indicating that in synovial cells (and in osteoblasts) 11β-HSD1 activity is upregulated by proinflammatory cytokines (Hardy et al., *Arthritis Res. Ther.*, 8, R108 (2006); Cooper et al., *J Bone Miner Res*, 16, 1037-44 (2001)). In animal models of RA, glycyrrhetinic acid, a pharmacologically active metabolite of a prodrug contained in the liquorice root *Glycyrrhiza glabra*, reduced inflammation and tissue destruction as well as bone erosion due to local cortisol concentrations in affected tissues (Buttgereit et al., *Annals of the Rheumatic Diseases*, 67, 1201-1203 (2008)); Chapman et al., *Ann. N.Y. Acad. Sci.*, 1088, 265-73 (2006); International Publication WO2005/027882).

Crook et al characterized local glucocorticoid (GC) metabolism in bone cells derived from C57BL/6 mice and examined its functional consequences in mice with targeted deletion of H6PDH. Primary mouse osteoblast cultures were derived from calvaria (n=8 mice) and long bones (n=8) of mice by outgrowth of collagenase treated bone chips. The osteoblastic character of these cells was confirmed by high basal and GC-inducible alkaline phosphatase activity bone restricted gene expression. 11β-HSD1 but not 11β-HSD2 mRNA was detected. Enzyme activity studies revealed predominant glucocorticoid activation (cortisone to cortisol conversion 3.8+2.1; dehydrocorticosterone to corticosterone 6.6+1.1 pmol/mg/hr) further indicating 11β-HSD1 expression. As in human osteoblasts 11β-HSD1 expression increased with IL-1b treatment (2.5+0.2 fold with 10 ng/ml IL-1b). Hexose-6-phosphate dehydrogenase (H6PDH) was also expressed and targeted deletion changed the directionality of 11β-HSD1 activity towards predominant glucocorticoid inactivation. Primary cultures of mouse osteoclasts were established from bone marrow treated with MCSF/RANKL. 11β-HSD1 mRNA expression and activity were initially low but transiently increased (mRNA expression by 120%; activity by 30%) on day 5 coincident with the appearance of multinucleated osteoclasts. Marrow cultures from mice with H6PDH deletion were unexpectedly found to have substantially greater numbers of osteoclasts than the wild type. These data indicate that mouse osteoblasts and osteoclasts express GC activating enzymes and this activity is dependent on H6PDH. The finding of increased osteoclastogenesis in H6PDH KO mice suggests that glucocorticoid activation negatively impacts on osteoclast differentiation (Crook et al., *Endocrine Abstracts*, 13, P13 (2007)).

Glucocorticoids are also known to increase bone resorption and reduce bone formation in mammals (Turner et al. *Calcif Tissue Int.*, 54, 311-5 (1995); Lane, N E et al. *Med Pediatr Oncol.*, 41, 212-6, (2003)). 11β-HSD-1 mRNA expression and reductase activity have been demonstrated in primary cultures of human osteoblasts in homogenates of human bone (Bland et al., *J. Endocrinol.*, 161, 455-464 (1999); Cooper et al., *Bone*, 23, 119-125 (2000)). In surgical explants obtained from orthopedic operations, 11β-HSD-1 expression in primary cultures of osteoblasts was found to be increased approximately 3-fold between young and old donors (Cooper et al., *J. Bone Miner Res.*, 17, 979-986 (2002)). Glucocorticoids, such as prednisone and dexamethasone, are also commonly used to treat a variety of inflammatory conditions including arthritis, inflammatory bowel disease, and asthma. These steroidal agents have been shown to increase expression of 11β-HSD-1 mRNA and activity in human osteoblasts (Cooper et al., *J. Bone Miner Res.*, 17, 979-986 (2002)). These studies suggest that 11β-HSD-1 plays a potentially important role in the development of bone-related adverse events as a result of excessive glucocorticoid levels or activity. Bone samples taken from healthy human volunteers orally dosed with the non-selective HSD1/2 inhibitor carbenoxolone showed a significant decrease in markers of bone resorption (Cooper et al., *Bone*, 27, 375-81 (2000)). Therefore, potent, selective 11β-HSD-1 inhibitors would treat, control, ameliorate, delay, or prevent the onset of conditions of glucocorticoid-induced or age-dependent osteoporosis.

Glycyrrhetinic acid, nonselective 11β-HSD inhibitor, has been identified as a possible drug for RA (International Publication WO2005/027882). Previous studies (Walker et al., *J. of Clin. Endocrinology and Met.*, 80, 3155-3159 (1995)) have demonstrated that administration of carbenoxolone, a nonselective 11β-HSD inhibitor, improves insulin sensitivity in humans, causing serious side effects, such as hypertension, due to the inhibition of 11β-HSD-2.

Accordingly, an embodiment relates to a treatment of inflammation, chronic inflammation, pain, RA, osteoarthritis and osteroporosis using selective. 11β-HSD1 inhibitors.

Another embodiment provides a method for treating RA in a subject such that signs and symptoms of inflammation are reduced, and that bone integrity is maintained. In one embodiment, the methods of the disclosure include inducing a major clinical response of a subject having RA (WO 2007/120656), or osteoporosis.

Another embodiment is a method comprising administering to a subject in need thereof, a compound of formula (I)

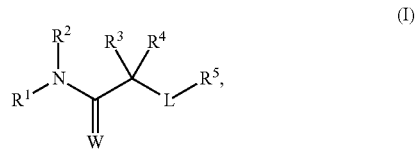

wherein

L is —(CH$_2$)$_n$—, or —(CH$_2$)$_m$—X—(CH$_2$)$_n$—;

m is 0, 1, or 2;

n is independently at each occurrence 0, 1, or 2;

R$^1$ is cycloalkyl or heterocycle;

R$^2$ is hydrogen, alkyl, or aryl; or R$^2$ and R$^3$ together with the atoms to which they are attached form a heterocycle;

R$^3$ and R$^4$ are independently hydrogen or alkyl; or R$^3$ and R$^4$ together with the atom to which they are attached form a cycloalkyl or heterocycle;

R$^5$ is hydrogen, alkyl, amino, aryl, cycloalkyl, heteroaryl, or heterocycle; or R$^4$ and R$^5$ together with the atoms to which they are attached form a cycloalkyl or heterocycle;

X is —O—, —S—, —S(O)$_2$—, —NR$^{36}$—, or —CR$^{36}$R$^{37}$—;

R$^{36}$ and R$^{37}$ are independently at each occurrence hydrogen or alkyl; or R$^{36}$ and R$^2$ together with the atoms to which they are attached form a heterocycle;

W is N—CN, N—OR$^6$, N—R$^6$, O, or S; and

R$^6$ is hydrogen, alkyl or aryl; or a pharmaceutically acceptable salt, ester, amide, or prodrug thereof.

Synthesis of compounds of the disclosure are described in U.S. Pat. Nos. 7,528,282; 7,511,175; 7,435,833 and 7,217, 838; U.S. Application Publication Nos. U.S. 2009/0054426; U.S. 2008/0312214; U.S. 2008/0076819; U.S. 2006/0281773; U.S. 2005/0277747; U.S. 2006/0149070; U.S. 2007/0208001; U.S. 2007/0129345; U.S. 2007/0167622; U.S. 2007/0066584; U.S. 2007/0088088; International Publication Nos. WO 2006132436; WO 2007118185; WO 2007111921; WO 2007145834; WO 2007145835; WO 2008088540; WO 2008011453; WO 2008099145; WO 2008012532; WO 2008053194; WO 2008024892; WO 2008074384; WO 2008052638; WO 2007124337; WO 2007127765; WO 2007127726; WO 2007127693; WO 2007127704; WO 2007127688; WO 2007127901; WO 2007127763; WO 2007124329; WO 2007124254; WO 2007107470; WO 2007101270; WO 2008069313; WO 2007084314; WO 2008157752; WO 2008142859; WO 2008006703; WO 2008006702; WO 2007107550; WO 2007115935; WO 2007051810; WO 2007051811; WO 2008110196; WO 2007144394; WO 2008134221; WO 2008127924; WO 2006048750; WO 2007058346; WO 2007114124; WO 2008142986; WO-2007114125; WO 2008101886; WO 2008101907; WO 2008101885; WO 2008101914; WO 2008119017; U.S. patent application Ser. No. 11/697,044; Barf, T. et al., *Drugs of the Future* 2006, 31(3), 231-243; Hughes, K. A., et al., *Expert Opin. Investig. Drugs* 2008, 17(4), 481-496; Boyle, C. D. et al., *Expert Opin. Ther. Patents* 2009, 19(6), 801-825; Webster, S. P. et al., *Expert Opin. Ther. Patents* 2007, 17(12), 1407-1422; Boyle, C. D. *Current Opinion in Drug Discovery & Development* 2008, 11(4), 495-511; and Rew, Y.; et al., *Bioorganic & Medicinal Chemistry Letters* 2009, 19, 1797-1801.

Representative examples of formula I include, but are not limited to:

1. N—[(Z)-5-hydroxy-2-adamantyl]-2-{4-[5-(trifluoromethyl)pyridin-2-yl]piperazin-1-yl}acetamide;
2. N-[(E)-5-hydroxy-2-adamantyl]-2-{4-[5-(trifluoromethyl)pyridin-2-yl]piperazin-1-yl}acetamide;
3. N-[(E)-5-hydroxy-2-adamantyl]-2-{4-[5-(trifluoromethyl)pyridin-2-yl]piperazin-1-yl}propanamide;
4. 2-[(cis)-2,6-dimethylmorpholin-4-yl]-N-[(E)-5-hydroxy-2-adamantyl]propanamide;
5. N—[(Z)-5-hydroxy-2-adamantyl]-2-(4-hydroxypiperidin-1-yl)propanamide;
6. N-[(E)-5-hydroxy-2-adamantyl]-2-(4-hydroxypiperidin-1-yl)propanamide;
7. 2-azepan-1-yl-N-[(E)-5-hydroxy-2-adamantyl]propanamide;
8. (E)-4-[({4-[5-(trifluoromethyl)pyridin-2-yl]piperazin-1-yl}acetyl)amino]-1-adamantyl carbamate;
9. (E)-4-[(2-{4-[5-(trifluoromethyl)pyridin-2-yl]piperazin-1-yl}acetyl)amino]-1-adamantyl acetate;
10. N-[(E)-5-(acetylamino)-2-adamantyl]-2-{4-[5-(trifluoromethyl)pyridin-2-yl]piperazin-1-yl}acetamide;
11. N-[(E)-5-fluoro-2-adamantyl]-2-{4-[5-(trifluoromethyl)pyridin-2-yl]piperazin-1-yl}acetamide;
12. N—[(Z)-5-fluoro-2-adamantyl]-2-{4-[5-(trifluoromethyl)pyridin-2-yl]piperazin-1-yl}acetamide;
13. N-[(E)-5-hydroxy-2-adamantyl]-2-[4-(5-methylpyridin-2-yl)piperazin-1-yl]propanamide;
14. [(E)-5-hydroxy-2-adamantyl]-2-methyl-2-{4-[5-(trifluoromethyl)pyridin-2-yl]piperazin-1-yl}propanamide;
15. (E)-4-{2-methyl-2-[4-(5-trifluoromethyl-pyridin-2-yl)-piperazin-1-yl]-propionylamino}-adamantane-1-carboxylic acid;
16. (E)-4-({1-[4-(5-trifluoromethyl-pyridin-2-yl)-piperazin-1-yl]-cyclopropanecarbonyl}-amino)-adamantane-1-carboxylic acid;
17. (E)-4-({1-[4-(5-trifluoromethyl-pyridin-2-yl)-piperazin-1-yl]-cyclopropanecarbonyl}-amino)-adamantane-1-carboxyamide;
18. (E)-4-{2-[4-(5-trifluoromethyl-pyridin-2-yl)-piperazin-1-yl]-butyrylamino}-adamantane-1-carboxyamide;
19. (E)-4-{2-cyclopropyl-2-[4-(5-trifluoromethyl-pyridin-2-yl)-piperazin-1-yl]-acetylamino}-adamantane-1-carboxyamide;
20. (E)-4-({1-[4-(5-trifluoromethyl-pyridin-2-yl)-piperazin-1-yl]-cyclobutanecarbonyl}-amino)-adamantane-1-carboxamide;
21. (E)-N-(5-hydroxymethyl-adamantan-2-yl)-2-[4-(5-trifluoromethyl-pyridin-2-yl)-piperazin-1-yl]-isobutyramide;
22. (E)-N-(5-formyl-adamantan-2-yl)-2-[4-(5-trifluoromethyl-pyridin-2-yl)-piperazin-1-yl]-isobutyramide;
23. (E)-4-{2-methyl-2-[4-(5-trifluoromethyl-pyridin-2-yl)-piperazin-1-yl]-propionylamino}-adamantane-1-carboxyamide;
24. (E)-4-{2-methyl-2-[4-(5-trifluoromethyl-pyridin-2-yl)-piperazin-1-yl]-propionylamino}-adamantane-1-carboxylic acid hydroxyamide;
25. (E)-4-{2-[4-(5-trifluormethyl-pyridin-2-yl)-piperazin-1-yl]-acetylamino}adamantane-1-carboxylic acid;
26. (E)-4-[2-(3,3-difluoro-piperidin-1-yl)-acetylamino]-adamantane-1-carboxylic acid;
27. (E)-4-[2-(2-trifluoromethyl-pyrrolidin-1-yl)-acetylamino]-adamantane-1-carboxylic acid;
28. (E)-4-{2-[4-(5-trifluoromethyl-pyridin-2-yl)-piperazin-1-yl]-acetylamino}-adamantane-1-carboxyamide;
29. (E)-4-[2-(2-trifluoromethyl-pyrrolidin-1-yl)-acetylamino]-adamantane-1-carboxyamide;
30. (E)-4-[2-(3,3-difluoro-piperidin-1-yl)-acetylamino]-adamantane-1-carboxyamide;
31. (E)-4-[2-(3-fluoropyrrolidin-1-yl)-propionylamino]-adamantane-1-carboxyamide;
32. (E)-4-[2-(3,3-difluoropiperidine-1-yl)-propionylamino]-adamantane-1-carboxyamide;
33. (E)-4-[2-(2-trifluoromethylpyrrolidin-1-yl)-propionylamino]-adamantane-1-carboxyamide;
34. (E)-4-{2-[4-(5-chloro-pyridin-2-yl)-piperazin-1-yl]-2-methyl-propionylamino}-adamantane-1-carboxylic acid;
35. (E)-4-[2-methyl-2-(1,2,4,5-tetrahydro-benzo[d]azepin-3-yl)-propionylamino]-adamantane-1-carboxylic acid;
36. (E)-4-[2-methyl-2-(4-m-tolyl-[1,4]diazepan-1-yl)-propionylamino]-adamantane-1-carboxylic acid;
37. (E)-4-[2-methyl-2-(4-phenyl-piperidin-1-yl)-propionylamino]-adamantane-1-carboxylic acid;
38. (E)-4-{2-[4-(4-chloro-phenyl)-piperidin-1-yl]-2-methyl-propionylamino}-adamantane-1-carboxylic acid;
39. (E)-4-{2-[5-(6-chloro-pyridin-3-yl)-hexahydro-pyrrolo[3,4-c]pyrrol-2-yl]-2-methyl-propionylamino}-adamantane-1-carboxyamide;
40. (E)-4-{2-[4-(5-fluoro-pyridin-3-yl)-[1,4]diazepan-1-yl]-2-methyl-propionylamino}-adamantane-1-carboxyamide;
41. (E)-4-[2-methyl-2-(3-pyridin-3-yl-3,9-diazbicyclo[4.2.1]non-9-yl)-propionylamino]-adamantane-1-carboxyamide;
42. (E)-4-[2-methyl-2-(2-trifluoromethyl-pyrrolidin-1-yl)-propionylamino]-adamantane-1-carboxyamide;
43. (E)-4-[2-(3,3-difluoro-piperidin-1-yl)-2-methyl-propionylamino]-adamantane-1-carboxyamide;
44. (E)-4-[2-(3-fluoro-pyrrolidin-1-yl)-2-methyl-propionylamino]-adamantane-1-carboxyamide;
45. (E)-4-{2-[4-(5-trifluormethyl-pyridin-2-yl)-piperazin-1-yl]-acetylamino}-adamantane-1-carboxamide;
46. (E)-4-[2-(3,3-difluoro-piperidin-1-yl)-2-methyl-propionylamino]-adamantane-1-carboxylic acid 3,4-dimethoxy-benzylamide;
47. (E)-4-[({4-[2-(3,3-difluoro-piperidin-1-yl)-2-methyl-propionylamino]-adamantane-1-carbonyl}-amino)-methyl]-benzoic acid;
48. (E)-4-[2-(3,3-difluoro-piperidin-1-yl)-2-methyl-propionylamino]-adamantane-1-carboxylic acid (furan-2-ylmethyl)-amide;
49. (E)-4-[2-(3,3-difluoro-piperidin-1-yl)-2-methyl-propionylamino]-adamantane-1-carboxylic acid (thiazol-5-ylmethyl)-amide;
50. (E)-4-[2-(3,3-difluoro-piperidin-1-yl)-2-methyl-propionylamino]-adamantane-1-carboxylic acid 2-methoxy-benzylamide;
51. (E)-4-(2-methyl-2-phenylamino-propionylamino)-adamantane-1-carboxyamide;
52. (E)-4-[2-methyl-2-(3-pyridin-3-yl-3,9-diazbicyclo[4.2.1]non-9-yl)-propionylamino]-adamantane-1-carboxyamide;
53. (E)-4-{2-methyl-2-[5-(3-trifluoromethyl-phenyl)-[1,5]diazocan-1-yl]-propionylamino}-adamantane-1-carboxylic acid;
54. (E)-4-{2-[7-(5-bromo-pyridin-2-yl)-3,7-diazbicyclo[3.3.1]non-3-yl]-2-methyl-propionylamino}-adamantane-1-carboxyamide;
55. $N^2$-[2-(4-chlorophenyl)ethyl]-$N^1$-[(E)-5-hydroxy-2-adamantyl]alaninamide;
56. 2-(4-benzylpiperidin-1-yl)-N-[(E)-5-hydroxy-2-adamantyl]propanamide;

57. N-[(E)-5-hydroxy-2-adamantyl]-2-(6,7,9,10-tetrahydro-8H[1,3]dioxolo[4,5-g][3]benzazepin-8-yl)propanamide;
58. N-[(E)-5-hydroxy-2-adamantyl]-2-(4-pyridin-2-ylpiperazin-1-yl)propanamide;
59. 2-[4-(4-fluorophenyl)piperazin-1-yl]-N-[(E)-5-hydroxy-2-adamantyl]propanamide;
60. N-[(E)-5-hydroxy-2-adamantyl]-2-[4-(4-methoxyphenyl)piperazin-1-yl]propanamide;
61. 2-[4-(5-cyanopyridin-2-yl)piperazin-1-yl]-N-[(E)-5-hydroxy-2-adamantyl]propanamide;
62. 2-[4-(2-furoyl)piperazin-1-yl]-N-[(1R,3S)-5-hydroxy-2-adamantyl]propanamide;
63. 2-(1,3-dihydro-2H-isoindol-2-yl)-N-[(E)-5-hydroxy-2-adamantyl]propanamide;
64. N-[(E)-5-hydroxy-2-adamantyl]-2-{4-[4-(trifluoromethyl)phenyl]piperazin-1-yl}(2S)—N-[(E)-5-hydroxy-2-adamantyl]-2-{4-[5-(trifluoromethyl)pyridin-2-yl]piperazin-1-yl}propanamide;
65. (2R)—N-[(E)-5-hydroxy-2-adamantyl]-2-{4-[5-(trifluoromethyl)pyridin-2-yl]piperazin-1-yl}propanamide;
66. 2-[3-(4-chlorophenoxy)azetidin-1-yl]-N-[(E)-5-hydroxy-2-adamantyl]propanamide;
67. 2-[4-(2-fluorophenoxy)piperidin-1-yl]-N-[(E)-5-hydroxy-2-adamantyl]propanamide;
68. 2-[3-(2-fluorophenoxy)piperidin-1-yl]-N-[(E)-5-hydroxy-2-adamantyl]propanamide;
69. 2-[3-(3-fluorophenoxy)pyrrolidin-1-yl]-N-[(E)-5-hydroxy-2-adamantyl]propanamide;
70. $N^2$-[2-(3,4-dichlorophenyl)ethyl]-$N^1$-[(E)-5-hydroxy-2-adamantyl]-$N^2$-methylalaninamide;
71. $N^2$-[2-(4-chlorophenyl)-1-methylethyl]-$N^1$-[(E)-5-hydroxy-2-adamantyl]-$N^2$-methylalaninamide;
72. 2-(5-chloro-2,3-dihydro-1H-indol-1-yl)-N-[(E)-5-hydroxy-2-adamantyl]propanamide;
73. 2-[4-(6-chloropyridin-3-yl)piperazin-1-yl]-N-[(E)-5-hydroxy-2-adamantyl]propanamide;
74. N-[(E)-5-hydroxy-2-adamantyl]-2-(3-phenylazetidin-1-yl)propanamide;
75. (E)-N-methyl-4-[(2-methyl-2-{4-[5-(trifluoromethyl)pyridin-2-yl]piperazin-1-yl}propanoyl)amino]adamantane-1-carboxamide;
76. (E)-N-methoxy-4-[(2-methyl-2-{4-[5-(trifluoromethyl)pyridin-2-yl]piperazin-1-yl}propanoyl)amino]adamantane-1-carboxamide;
77. N-[(E)-5-(aminomethyl)-2-adamantyl]-2-methyl-2-{4-[5-(trifluoromethyl)pyridin-2-yl]piperazin-1-yl) propanamide;
78. N-[(E)-5-hydroxy-2-adamantyl]-1-{[4-(trifluoromethyl)benzyl]amino}cyclopropanecarboxamide;
79. N-[(E)-5-cyano-2-adamantyl]-2-methyl-2-{4-[5-(trifluoromethyl)pyridin-2-yl]piperazin-1-yl}propanamide;
80. N-[(E)-5-hydroxy-2-adamantyl]-1-piperidin-1-ylcyclopropanecarboxamide;
81. 2-methyl-N-[(E)-5-(5-methyl-1,2,4-oxadiazol-3-yl)-2-adamantyl]-2-{4-[5-(trifluoromethyl)pyridin-2-yl]piperazin-1-yl}propanamide;
82. 2-methyl-N-[(E)-5-(2H-tetraazol-5-yl)-2-adamantyl]-2-{4-[5-(trifluoromethyl)pyridin-2-yl]piperazin-1-yl}propanamide;
83. (E)-4-[(2-{4-[[(4-chlorophenyl)sulfonyl](cyclopropyl)amino]piperidin-1-yl}propanoyl)amino]adamantane-1-carboxamide;
84. N-[(E)-5-hydroxy-2-adamantyl]-2-methyl-2-[2-(trifluoromethyl)pyrrolidin-1-yl]propanamide;
85. (E)-4-({2-[(3S)-3-fluoropyrrolidin-1-yl]-2-methylpropanoyl}amino)adamantane-1-carboxamide;
86. methyl (E)-4-{[2-methyl-2-(4-pyridin-2-ylpiperazin-1-yl)propanoyl]amino}adamantane-1-carboxylate;
87. (E)-4-{[2-methyl-2-(4-pyridin-2-ylpiperazin-1-yl)propanoyl]amino}adamantane-1-carboxylic acid;
88. (E)-4-({2-methyl-2-[(2S)-2-methyl-4-pyridin-2-ylpiperazin-1-yl]propanoyl}amino) adamantane-1-carboxylic acid;
89. (E)-4-{[2-methyl-2-(4-pyridin-2-ylpiperazin-1-yl)propanoyl]amino}adamantane-1-carboxamide;
90. 2-methyl-N-[(E)-5-(4H-1,2,4-triazol-3-yl)-2-adamantyl]-2-{4-[5-(trifluoromethyl)pyridin-2-yl]piperazin-1-yl}propanamide;
91. (E)-4-{([2-(3,3-difluoropiperidin-1-yl)-2-methylpropanoyl]amino}-N-(pyridin-4-ylmethyl) adamantane-1-carboxamide;
92. (E)-4-[(2-methyl-2-{4-[4-(trifluoromethyl)phenyl]piperazin-1-yl}propanoyl)amino]adamantane-1-carboxylic acid;
93. (E)-4-({2-methyl-2-[(2R)-2-methyl-4-(5-methylpyridin-2-yl)piperazin-1-yl]propanoyl}amino)adamantane-1-carboxylic acid;
94. (E)-4-({2-[(3S)-3-fluoropiperidin-1-yl]propanoyl}amino)adamantane-1-carboxamide;
95. (E)-4-[((2S)-2-{4-[5-(trifluoromethyl)pyridin-2-yl]piperazin-1-yl}propanoyl)amino]adamantane-1-carboxamide;
96. (E)-4-[((2R)-2-{4-[5-(trifluoromethyl)pyridin-2-yl]piperazin-1-yl}propanoyl)amino]adamantane-1-carboxamide;
97. (E)-4-[({2-(trifluoromethyl)-4-[5-(trifluoromethyl)pyridin-2-yl]piperazin-1-yl}acetypamino]adamantane-1-carboxamide;
98. (E)-4-[(cyclopropyl{4-[5-(trifluoromethyl)pyridin-2-yl]piperazin-1-yl}acetyl)amino]adamantane-1-carboxylic acid;
99. (E)-4-{[(1-{4-[5-(trifluoromethyl)pyridin-2-yl]piperazin-1-yl}cyclobutyl)carbonyl]amino}adamantane-1-carboxylic acid;
100. (E)-4-({2-[9-(6-chloropyridin-3-yl)-3,9-diazabicyclo[4.2.1]non-3-yl]-2-methylpropanoyl}amino)adamantane-1-carboxamide;
101. (E)-4-({2-[4-(2,3-dichlorophenyl)piperazin-1-yl]-2-methylpropanoyl}amino) adamantane-1-carboxylic acid;
102. (E)-4-{[2-methyl-2-(4-phenylpiperazin-1-yl)propanoyl]amino}adamantane-1-carboxylic acid;
103. (E)-4-({2-methyl-2-[4-(4-methylphenyl)piperazin-1-yl]propanoyl}amino) adamantane-1-carboxylic acid;
104. (E)-4-({2-[4-(1,3-benzothiazol-2-yl)piperazin-1-yl]-2-methylpropanoyl}amino) adamantine-1-carboxylic acid;
105. (E)-4-({2-[4-(3,4-dichlorophenyl)piperazin-1-yl]-2-methylpropanoyl}amino) adamantane-1-carboxylic acid;
106. (E)-4-({2-methyl-2-[4-(3-methylphenyl)piperazin-1-yl]propanoyl}amino) adamantane-1-carboxylic acid;
107. (E)-4-[(2-methyl-2-{4-[2-(trifluoromethyl)phenyl piperazin-1-yl}propanoyl)amino]adamantane-1-carboxylic acid;
108. (E)-4-({2-[4-(2,4-difluorophenyl)piperazin-1-yl]-2-methylpropanoyl}amino) adamantane-1-carboxylic acid;
109. (E)-4-({2-methyl-2-[4-(6-methylpyridin-2-yl)piperazin-1-yl]propanoyl}amino)adamantane-1-carboxylic acid;
110. (E)-4-{[2-methyl-2-(4-pyrimidin-2-ylpiperazin-1-yl)propanoyl]amino}adamantane-1-carboxylic acid;
111. (E)-4-({2-[4-(4-fluorophenyl)piperazin-1-yl]-2-methylpropanoyl}amino)adamantane-1-carboxylic acid;

112. (E)-4-[(2-methyl-2-{4-[3-(trifluoromethyl)phenyl]piperazin-1-yl}propanoyl)amino]adamantane-1-carboxylic acid;
113. (E)-4-[(2-methyl-2-{4-[3-(trifluoromethyl)pyridin-2-yl]piperazin-1-yl}propanoyl)amino]adamantane-1-carboxylic acid;
114. (E)-4-({2-[4-(3-chlorophenyl)piperazin-1-yl]-2-methylpropanoyl}amino)adamantane-1-carboxylic acid;
115. (E)-4-({2-[4-(4-acetylphenyl)piperazin-1-yl]-2-methylpropanoyl}amino)adamantane-1-carboxylic acid;
116. (E)-N,N-dimethyl-4-[(2-methyl-2-{4-[5-(trifluoromethyl)pyridin-2-yl]piperazin-1-yl}propanoyl)amino]adamantane-1-carboxamide;
117. N-[(E)-5-(acetylamino)-2-adamantyl]-2-{4-[5-(trifluoromethyl)pyridin-2-yl]piperazin-1-yl}propanamide;
118. (E)-4-{([2-methyl-2-(4-pyrimidin-2-ylpiperazin-1-yl)propanoyl]amino}adamantane-1-carboxamide;
119. (E)-4-{[2-methyl-2-(4-pyrazin-2-ylpiperazin-1-yl)propanoyl]amino}adamantane-1-carboxamide;
120. (E)-4-({2-[4-(4-fluorophenyl)piperazin-1-yl]-2-methylpropanoyl}amino)adamantane-1-carboxamide;
121. (E)-4-({2-[4-(3-cyanopyridin-2-yl)piperazin-1-yl]-2-methylpropanoyl}amino) adamantane-1-carboxamide;
122. (E)-4-({2-methyl-2-[4-(6-methylpyridin-3-yl)-1,4-diazepan-1-yl]propanoyl}amino)adamantane-1-carboxamide;
123. (E)-4-[(2-{4-[3-chloro-5-(trifluoromethyl)pyridin-2-yl]piperazin-1-yl}-2-methylpropanoyl)amino]adamantane-1-carboxylic acid;
124. 4-(2-{[((E)-4-{[2-(3,3-difluoropiperidin-1-yl)-2-methylpropanoyl]amino}-1-adamantyl) carbonyl] amino}ethyl)benzoic acid;
125. N-{(E)-5-[(methylsulfonyl)amino]-2-adamantyl}-2-{4-[5-(trifluoromethyl)pyridin-2-yl]piperazin-1-yl}propanamide;
126. N-[(E)-5-(1-hydroxy-1-methylethyl)-2-adamantyl]-2-methyl-2-{4-[5-(trifluoromethyl)pyridin-2-yl]piperazin-1-yl}propanamide;
127. (E)-4-{[2-methyl-2-(4-phenylpiperazin-1-yl)propanoyl]amino}adamantane-1-carboxamide;
128. (E)-4-({2-[4-(2-methoxyphenyl)piperazin-1-yl]-2-methylpropanoyl}amino)adamantane-1-carboxamide;
129. (E)-4-[(N,2-dimethyl-N-phenylalanyl)amino]adamantane-1-carboxamide;
130. (E)-4-({2-[4-(2,4-dimethoxyphenyl)piperazin-1-yl]-2-methylpropanoyl}amino) adamantine-1-carboxamide;
131. (E)-4-({2-[4-(2,3-dicyanophenyl)piperazin-1-yl]-2-methylpropanoyl}amino) adamantane-1-carboxamide;
132. N-[(E)-5-(cyanomethyl)-2-adamantyl]-2-methyl-2-{4-[5-(trifluoromethyl)pyridin-2-yl]piperazin-1-yl}propanamide;
133. (E)-4-({2-methyl-2-[4-(4-nitrophenyl)piperazin-1-yl]propanoyl}amino)adamantane-1-carboxylic acid;
134. (E)-4-({2-[4-(2,4-dichlorophenyl)piperazin-1-yl]-2-methylpropanoyl}amino) adamantane-1-carboxylic acid;
135. {(E)-4-[(2-methyl-2-{4-[5-(trifluoromethyl)pyridin-2-yl]piperazin-1-yl}propanoyl)amino]-1-adamantyl}acetic acid;
136. (E)-4-({2-[4-(4-chloro-2-fluorophenyl)piperazin-1-yl]-2-methylpropanoyl}amino)adamantane-1-carboxylic acid;
137. (E)-4-[(2-methyl-2-{4-[4-(trifluoromethyl)pyrimidin-2-yl]piperazin-1-yl}propanoyl)amino]adamantane-1-carboxylic acid;
138. (E)-4-({2-[4-(3-chloro-4-fluorophenyl)piperazin-1-yl]-2-methylpropanoyl}amino)adamantane-1-carboxylic acid;
139. (E)-4-({2-[4-(4-cyanophenyl)piperazin-1-yl]-2-methylpropanoyl}amino)adamantane-1-carboxylic acid;
140. (E)-4-({2-[4-(4-bromophenyl)piperazin-1-yl]-2-methylpropanoyl}amino) adamantane-1-carboxylic acid;
141. (E)-4-({2-[4-(5-chloro-2-methoxyphenyl)piperazin-1-yl]-2-methylpropanoyl}amino)adamantane-1-carboxylic acid;
142. (E)-4-({2-[4-(2-chlorophenyl)piperazin-1-yl]-2-methylpropanoyl}amino)adamantane-1-carboxylic acid;
143. (E)-4-({2-[4-(2-cyanophenyl)piperazin-1-yl]-2-methylpropanoyl}amino)adamantane-1-carboxylic acid;
144. (E)-4-({2-[4-(2-fluorophenyl)piperazin-1-yl]-2-methylpropanoyl}amino)adamantane-1-carboxylic acid;
145. (E)-4-({2-methyl-2-[4-(2-methylphenyl)piperazin-1-yl]propanoyl}amino) adamantane-1-carboxylic acid;
146. (E)-4-({2-[4-(4-chlorophenyl)piperazin-1-yl]-2-methylpropanoyl}amino)adamantane-1-carboxylic acid;
147. (E)-4-({2-[4-(3-chloropyridin-2-yl)piperazin-1-yl]-2-methylpropanoyl}amino) adamantine-1-carboxylic acid;
148. (E)-4-[(2-{4-[2-chloro-4-(trifluoromethyl)phenyl]piperazin-1-yl}-2-methylpropanoyl)amino]adamantane-1-carboxylic acid;
149. (E)-4-({2-[(3R)-3-fluoropyrrolidin-1-yl]-2-methylpropanoyl}amino)-N-(pyridin-3-ylmethyl)adamantane-1-carboxamide;
150. (E)-4-{[2-methyl-2-(3-phenylpiperidin-1-yl)propanoyl]amino}adamantane-1-carboxamide;
151. (E)-4-({2-[4-(2-chloro-4-methylphenyl)piperazin-1-yl]-2-methylpropanoyl}amino)adamantane-1-carboxylic acid;
152. (E)-4-({2-[4-(2-fluorophenyl)piperidin-1-yl]-2-methylpropanoyl}amino)adamantane-1-carboxylic acid;
153. (E)-4-({2-methyl-2-[4-(2-methylphenyl)piperidin-1-yl]propanoyl}amino) adamantane-1-carboxylic acid;
154. (E)-4-({2-[4-(2-chloro-4-fluorophenyl)piperazin-1-yl]-2-methylpropanoyl}amino)adamantane-1-carboxamide;
155. (E)-4-({2-[4-(2-furoyl)piperazin-1-yl]-2-methylpropanoyl}amino)adamantane-1-carboxylic acid;
156. (E)-4-({2-[4-(2-chloro-4-cyanophenyl)piperazin-1-yl]-2-methylpropanoyl}amino)adamantane-1-carboxylic acid;
157. (E)-4-({2-[4-(2-chloro-4-fluorophenyl)piperazin-1-yl]-2-methylpropanoyl}amino)adamantane-1-carboxylic acid;
158. (E)-4-[(2-methyl-2-{4-[5-(trifluoromethyl)pyridin-2-yl]piperazin-1-yl}propanoyl)amino]-1-adamantyl carbamate;
159. (E)-4-[(2-{4-[(4-chlorophenyl)sulfonyl]piperazin-1-yl}-2-methylpropanoyl)amino]adamantane-1-carboxylic acid;
160. (E)-4-({2-[4-(2,4-difluorophenyl)piperidin-1-yl]-2-methylpropanoyl}amino) adamantane-1-carboxylic acid;
161. (E)-4-({2-[4-(4-cyano-2-fluorophenyl)piperazin-1-yl]-2-methylpropanoyl}amino)adamantane-1-carboxylic acid;
162. (E)-4-[(2-methyl-2-{3-methyl-4-[5-(trifluoromethyl)pyridin-2-yl]piperazin-1-yl}propanoyl)amino]adamantane-1-carboxylic acid;
163. (E)-4-({2-[4-(4-cyanophenyl)-3,5-dimethyl-1H-pyrazol-1-yl]-2-methylpropanoyl}amino)adamantane-1-carboxylic acid;
164. (E)-4-({2-[4-(4-cyanophenyl)-3,5-dimethyl-1H-pyrazol-1-yl]-2-methylpropanoyl}amino)adamantane-1-carboxamide;
165. (E)-4-{[2-methyl-N-(3-methylphenyl)alanyl]amino}adamantane-1-carboxamide;

166. tert-butyl 4-(2-{[(E)-5-(aminocarbonyl)-2-adamantyl]amino}-1,1-dimethyl-2-oxoethyl)piperazine-1-carboxylate;
167. (2R)-2-[(3R)-3-fluoropyrrolidin-1-yl]-N-[(E)-5-hydroxy-2-adamantyl]propanamide;
168. (E)-4-({2-[4-(2-bromophenyl)piperazin-1-yl]-2-methylpropanoyl}amino)adamantane-1-carboxylic acid;
169. (E)-4-{[N-(3-chlorophenyl)-2-methylalanyl]amino}adamantane-1-carboxamide;
170: (E)-4-{[N-(3-methoxyphenyl)-2-methylalanyl]amino}adamantane-1-carboxamide;
171. (E)-4-({2-[4-(4-cyanophenyl)-3,5-dimethyl-1H-pyrazol-1-yl]-2-methylpropanoyl}amino)-N-(1,3-thiazol-5-ylmethyl)adamantane-1-carboxamide;
172. (E)-4-({2-[4-(6-chloropyrimidin-4-yl)piperazin-1-yl]-2-methylpropanoyl}amino)adamantane-1-carboxylic acid;
173. (E)-4-({2-[4-(6-chloropyridazin-3-yl)piperazin-1-yl]-2-methylpropanoyl}amino)adamantane-1-carboxylic acid;
174. (E)-4-({2-[4-(2-chloropyrimidin-4-yl)piperazin-1-yl]-2-methylpropanoyl}amino)adamantane-1-carboxylic acid;
175. N-[({(E)-4-[(2-methyl-2-{4-[5-(trifluoromethyl)pyridin-2-yl]piperazin-1-yl}propanoyl)amino]-1-adamantyl}amino)carbonyl]glycine;
176. (E)-4-({2-[4-(5-cyanopyridin-2-yl)piperazin-1-yl]-2-methylpropanoyl}amino)adamantine-1-carboxylic acid;
177. (E)-4-({2-[4-(3-chloro-5-cyanopyridin-2-yl)piperazin-1-yl]-2-methylpropanoyl}amino)adamantane-1-carboxylic acid;
178. (E)-4-({2-methyl-2-[4-(1,3-thiazol-2-yl)piperazin-1-yl]propanoyl}amino) adamantane-1-carboxylic acid;
179. (E)-4-{[N-(4-methoxyphenyl)-2-methylalanyl]amino}adamantane-1-carboxamide;
180. (E)-4-({N-[4-(dimethylamino)phenyl]-2-methylalanyl}amino)adamantane-1-carboxamide;
181. (E)-4-({2-methyl-N-[4-(trifluoromethyl)phenyl]alanyl}amino)adamantane-1-carboxamide;
182. (E)-4-({2-methyl-N-[3-(trifluoromethyl)phenyl]alanyl}amino)adamantane-1-carboxamide;
183. (E)-4-({2-[4-(2-hydroxyphenyl)piperazin-1-yl]-2-methylpropanoyl}amino) adamantane-1-carboxylic acid;
184. 4-(2-{[(E)-5-(aminocarbonyl)-2-adamantyl]amino}-1,1-dimethyl-2-oxoethyl)-N-(tert-butyl)piperazine-1-carboxamide; and
185. N-[(E)-5-(formylamino)-2-adamantyl]-2-methyl-2-{4-[5-(trifluoromethyl)pyridin-2-yl]piperazin-1-yl}propanamide.
186. (E)-4-[(2-methyl-2-phenoxypropanoyl)amino]adamantane-1-carboxamide;
187. (E)-4-[(2-methyl-2-{[4-(trifluoromethyl)benzyl]oxy}propanoyl)amino]adamantane-1-carboxamide;
188. (E)-4-({2-methyl-2-[(2-methylcyclohexyl)oxy]propanoyl}amino)adamantane-1-carboxylic acid;
189. (E)-4-({2-methyl-2-[(3-methylcyclohexyl)oxy]propanoyl}amino)adamantane-1-carboxylic acid;
190. (E)-4-{[2-(cycloheptyloxy)-2-methylpropanoyl]amino}adamantane-1-carboxylic acid;
191. (E)-4-{[2-(cyclohexylmethoxy)-2-methylpropanoyl]amino}adamantane-1-carboxylic acid;
192. (E)-4-{[2-(4-chlorophenoxy)-2-methylpropanoyl]amino}adamantane-1-carboxylic acid;
193. (E)-4-{[2-(4-chlorophenoxy)-2-methylpropanoyl]amino}adamantane-1-carboxamide;
194. (E)-4-({2-methyl-2-[(4-methylcyclohexyl)oxy]propanoyl}amino)adamantane-1-carboxamide;
195. (E)-4-[(2-phenoxypropanoyl)amino]adamantane-1-carboxamide;
196. (E)-4-{[2-methyl-2-(2-methyl-phenoxy)propanoyl]amino}adamantane-1-carboxylic acid;
197. (E)-4-{[2-methyl-2-(4-methylphenoxy)propanoyl]amino}adamantane-1-carboxylic acid;
198. (E)-4-{[2-(2-chlorophenoxy)-2-methylpropanoyl]amino}adamantane-1-carboxylic acid;
199. (E)-4-{[2-(2-methoxyphenoxy)-2-methylpropanoyl]amino}adamantane-1-carboxamide;
200. (E)-4-{[2-(4-methoxyphenoxy)-2-methylpropanoyl]amino}adamantane-1-carboxamide;
201. (E)-4-({2-methyl-2-[3-(trifluoromethyl)phenoxy]propanoyl}amino)adamantane-1-carboxamide;
202. (E)-4-{[2-(3-methoxyphenoxy)-2-methylpropanoyl]amino}adamantane-1-carboxamide;
203. (E)-2-(4-chloro-phenoxy)-N-(5-hydroxy-adamantan-2-yl)-2-methyl-propionamide;
204. (E)-{[2-methyl-2-(4-methylphenoxy)propanoyl]amino}adamantane-1-carboxamide;
205. (E)-4-{[2-(3-chlorophenoxy)-2-methylpropanoyl]amino}adamantane-1-carboxamide;
206. (E)-4-({2-methyl-2-[4-(trifluoromethoxy)phenoxy]propanoyl}amino)adamantane-1-carboxamide;
207. (E)-4-{[2-(3-bromophenoxy)-2-methylpropanoyl]amino}adamantane-1-carboxylic acid;
208. 4-({[((E)-4-{[2-(4-chlorophenoxy)-2-methylpropanoyl]amino}-1-adamantyl)carbonyl]amino}methyl) benzoic acid;
209. (E)-4-{[2-(2,3-dimethylphenoxy)-2-methylpropanoyl]amino}adamantane-1-carboxylic acid;
210. tert-butyl 4-(2-{[(E)-5-(aminocarbonyl)-2-adamantyl]amino}-1,1-dimethyl-2-oxoethoxy)phenylcarbamate;
211. (E)-N-[4-(aminocarbonyl)benzyl]-4-{[2-(4-chlorophenoxy)-2-methylpropanoyl]amino}adamantane-1-carboxamide;
212. (E)-N-[4-(aminocarbonyl)methyl]-4-{[2-(4-chlorophenoxy)-2-methylpropanoyl]amino}adamantane-1-carboxamide;
213. 3-({[((E)-4-{[2-(4-chlorophenoxy)-2-methylpropanoyl amino}-1-adamantyl) carbonyl]amino}methyl)benzoic acid;
214. (E)-4-({2-[(5-bromopyridin-2-yl)oxy]-2-methylpropanoyl}amino)adamantane-1-carboxamide;
215. (E)-4-{[2-(2-cyanophenoxy)-2-methylpropanoyl]amino}adamantane-1-carboxamide;
216. (E)-4-{[2-(4-hydroxyphenoxy)-2-methylpropanoyl]amino}adamantane-1-carboxamide;
217. ((E)-4-{[2-(4-chlorophenoxy)-2-methylpropanoyl]amino}-1-adamantyl)acetic acid;
218. N-[(E)-5-(2-amino-2-oxoethyl)-2-adamantyl]-2-(4-chlorophenoxy)-2-methylpropanamide;
219. 2-(4-chlorophenoxy)-2-methyl-N-[(E)-5-(2H-tetraazol-5-ylmethyl)-2-adamantyl]propanamide;
220. N-{(E)-5-[(aminosulfonyl)methyl]-2-adamantyl}-2-(4-chlorophenoxy)-2-methyl propanamide;
221. N-{(E)-5-[(Z)-amino(hydroxyimino)methyl]-2-adamantyl}-2-(4-chlorophenoxy)-2-methyl propanamide;
222. (E)-N-[4-(aminosulfonyl)benzyl]-4-{[2-(4-chlorophenoxy)-2-methylpropanoyl]amino}adamantane-1-carboxamide;
223. (E)-4-{[2-(4-chlorophenoxy)-2-methylpropanoyl]amino}-N-(4{[(methylsulfonyl)amino]carbonyl}benzyl) adamantane-1-carboxamide;
224. (E)-4-({2-[(4-chlorophenyl)thio]-2-methylpropanoyl}amino)adamantane-1-carboxylic acid;

225. (E)-4-({2-[(4-methoxyphenyl)thio]-2-methylpropanoyl}amino)adamantane-1-carboxamide amide;
226. (E)-4-({2-[(4-methoxyphenyl)sulfinyl]-2-methylpropanoyl}amino)adamantane-1-carboxamide;
227. (E)-4-({2-[(4-methoxyphenyl)sulfonyl]-2-methylpropanoyl}amino)adamantane-1-carboxamide;
228. (E)-4-({2-[4-chloro-2-(pyrrolidin-1-ylsulfonyl)phenoxy]-2-methylpropanoyl}amino)adamantane-1-carboxamide;
229. (E)-4-({2-methyl-2-[4-(methylsulfonyl)phenoxy]propanoyl}amino)adamantane-1-carboxamide;
230. (E)-4-({2-methyl-2-[2-(methylsulfonyl)phenoxy]propanoyl}amino)adamantane-1-carboxamide;
231. (E)-4-[(2-{4-chloro-2-[(diethylamino)sulfonyl]phenoxy}-2-methylpropanoyl)amino]adamantane-1-carboxamide;
232. (E)-4-({2-methyl-2-[4-(pyrrolidin-1-ylsulfonyl)phenoxy]propanoyl}amino) adamantane-1-carboxamide;
233. 2-(2-chloro-4-fluorophenoxy)-N-[(E)-5-hydroxy-2-adamantyl]-2-methylpropanamide;
234. 2-(2-chloro-4-fluorophenoxy)-2-methyl-N-[(E)-5-(2H-tetraazol-5-yl)-2-adamantyl]propanamide;
235. 2-(2-chloro-4-fluorophenoxy)-2-methyl-N-[(E)-5-(methylthio)-2-adamantyl]propanamide;
236. 2-(2-chloro-4-fluorophenoxy)-2-methyl-N-[(E)-5-(methylsulfonyl)-2-adamantyl]propanamide;
237. 2-(2-chloro-4-fluorophenoxy)-2-methyl-N-[(E)-5-(methylsulfinyl)-2-adamantyl]propanamide;
238. N-[(E)-5-(aminosulfonyl)-2-adamantyl]-2-(4-chlorophenoxy)-2-methylpropanamide;
239. (E)-4-({[1-(4-chlorophenoxy)cyclobutyl]carbonyl}amino)adamantane-1-carboxamide;
240. 4-[({[((E)-4-{[2-(4-chlorophenoxy)-2-methylpropanoyl]amino}-1-adamantyl)methyl]sulfonyl}amino)methyl]benzoic acid;
241. 2-(4-chlorophenoxy)-N-[(E)-5-(1H-imidazol-2-yl)-2-adamantyl]-2-methylpropanamide;
242. (2E)-3-((E)-4-{[2-(4-Chlorophenoxy)-2-methylpropanoyl]amino}-1-adamantyl)acrylic acid;
243. (E)-4-[(2-methyl-2-{[5-(1H-pyrazol-1-yl)pyridin-2-yl]oxy}propanoyl)amino]adamantine-1-carboxamide;
244. 2-(4-chlorophenoxy)-N-[(E)-5-isoxazol-5-yl-2-adamantyl]-2-methylpropanamide;
245. 2-(4-chlorophenoxy)-2-methyl-N-{(E)-5-[(2-morpholin-4-ylethoxy)methyl]-2-adamantyl}propanamide;
246. N-[(E)-5-(aminosulfonyl)-2-adamantyl]-2-(2-chlorophenoxy)-2-methylpropanamide;
247. N-[(E)-5-(aminosulfonyl)-2-adamantyl]-2-methyl-2-(2-methylphenoxy) propanamide;
248. N-[(E)-5-(aminosulfonyl)-2-adamantyl]-2-methyl-2-(4-methylphenoxy) propanamide;
249. N-[(E)-5-(aminosulfonyl)-2-adamantyl]-2-methyl-2-[2-(trifluoromethyl)phenoxy]propanamide;
250. N-[(E)-5-(aminosulfonyl)-2-adamantyl]-2-methyl-2-[2-(trifluoromethoxy)phenoxy]propanamide;
251. N-[(E)-5-(aminosulfonyl)-2-adamantyl]-2-(2-chloro-4-fluorophenoxy)-2-methyl-propanamide;
252. (E)-4-{[2-(2-chlorophenoxy)-2-methyl-3-phenylpropanoyl]amino}adamantane-1-carboxamide;
253. 2-(4-chlorophenoxy)-N-[(E)-5-hydroxy-2-adamantyl]-2-methylpropanamide;
254. (E)-4-({2-methyl-2-[(5-morpholin-4-ylpyridin-2-yl)oxy]propanoyl}amino)adamantane-1-carboxamide;
255. (E)-4-{[2-methyl-2-(pyridin-2-yloxy)propanoyl]amino}adamantane-1-carboxamide;
256. 2-(4-chlorophenoxy)-2-methyl-N-{(E)-5-[(methylamino)sulfonyl]-2-adamantyl}propanamide;
257. 3-((E)-4-{[2-(4-chlorophenoxy)-2-methylpropanoyl]amino}-1-adamantyl)propanoic acid;
258. 2-(4-chlorophenoxy)-N-{(E)-5-[(dimethylamino)sulfonyl]-2-adamantyl}-2-methylpropanamide;
259. (E)-4-[(2-{[5-(1H-imidazol-1-yl)pyridin-2-yl]oxy}-2-methylpropanoyl)amino]adamantine-1-carboxamide;
260. 2-(4-chlorophenoxy)-2-methyl-N-[(E)-5-(1H-pyrazol-3-yl)-2-adamantyl]propanamide;
261. N-[(E)-5-(aminosulfonyl)-2-adamantyl]-2-(3-chlorophenoxy)-2-methylpropanamide;
262. N-[(E)-5-(aminosulfonyl)-2-adamantyl]-2-methyl-2-(3-methylphenoxy)propanamide;
263. N-[(E)-5-(aminosulfonyl)-2-adamantyl]-2-(2-methoxyphenoxy)-2-methylpropanamide;
264. N-[(E)-5-(aminosulfonyl)-2-adamantyl]-2-(3-methoxyphenoxy)-2-methylpropanamide;
265. N-[(E)-5-(aminosulfonyl)-2-adamantyl]-2-(4-methoxyphenoxy)-2-methylpropanamide;
266. N-[(E)-5-(aminosulfonyl)-2-adamantyl]-2-(4-cyanophenoxy)-2-methylpropanamide;
267. (E)-4-{[2-methyl-2-(2-methyl-phenoxy)propanoyl]amino}adamantane-1-carboxamide;
268. (E)-4-{[2-methyl-2-(3-methylphenoxy)propanoyl]amino}adamantane-1-carboxamide;
269. (E)-4-[(2-methyl-2-{[(1,2S)-2-methylcyclohexyl]oxy}propanoyl)amino]adamantane-1-carboxylic acid;
270. (E)-4-({2-methyl-2-[(2-methylcyclohexyl)oxy]propanoyl}amino)adamantane-1-carboxamide
271. (E)-4-{[2-(cycloheptyloxy)-2-methylpropanoyl]amino}adamantane-1-carboxamide;
272. (E)-4-{[2-(cyclohexylmethoxy)-2-methylpropanoyl]amino}adamantane-1-carboxamide;
273. (E)-4-({2-methyl-2-[(3-methylcyclohexyl)oxy]propanoyl}amino)adamantane-1-carboxamide;
274. (E)-4-{[2-(2-chlorophenoxy)-2-methylpropanoyl]amino}adamantane-1-carboxamide;
275. 4-{[({(E)-4-[(2-methyl-2-phenoxypropanoyl)amino]-1-adamantyl}carbonyl)amino]methyl}benzoic acid;
276. (E)-4-({2-[(4,4-dimethylcyclohexyl)oxy]-2-methylpropanoyl}amino)adamantane-1-carboxylic acid;
277. (E)-4-{[2-methyl-2-(1,2,3,4-tetrahydronaphthalen-2-yloxy)propanoyl]amino}adamantane-1-carboxylic acid;
278. (E)-4-{[2-(4-bromophenoxy)-2-methylpropanoyl]amino}adamantane-1-carboxylic acid;
279. (E)-4-{[2-methyl-2-(1-naphthyloxy)propanoyl]amino}adamantane-1-carboxylic acid;
280. (E)-4-{[2-(2,3-dichlorophenoxy)-2-methylpropanoyl]amino}adamantane-1-carboxylic acid;
281. (E)-4-{[2-(2,4-dichlorophenoxy)-2-methylpropanoyl]amino}adamantane-1-carboxylic acid;
282. (E)-4-{[2-(2,5-dichlorophenoxy)-2-methylpropanoyl]amino}adamantane-1-carboxylic acid;
283. (E)-4-{[2-(2,4-dimethylphenoxy)-2-methylpropanoyl]amino}adamantane-1-carboxylic acid;
284. (E)-4-{[2-(2,5-dimethylphenoxy)-2-methylpropanoyl]amino}adamantane-1-carboxylic acid;
285. (E)-4-{[2-methyl-2-(2-naphthyloxy)propanoyl]amino}adamantane-1-carboxylic acid;
286. (E)-4-{[2-(4-bromo-2-fluorophenoxy)-2-methylpropanoyl]amino}adamantane-1-carboxylic acid;
287. (E)-4-({2-methyl-2-[(7-methyl-2,3-dihydro-1H-inden-4-yl)oxy]propanoyl}amino)adamantane-1-carboxylic acid;
288. (E)-4-{[2-(4-bromo-2-chlorophenoxy)-2-methylpropanoyl]amino}adamantane-1-carboxylic acid;

289. (E)-4-{[2-(1,1'-biphenyl-3-yloxy)-2-methylpropanoyl]amino}adamantane-1-carboxylic acid;
290. (E)-4-{([2-(2-bromophenoxy)-2-methylpropanoyl]amino}adamantane-1-carboxylic acid;
291. (E)-N-[4-(aminocarbonyl)benzyl]-4-[(2-methyl-2-phenoxypropanoyl)amino]adamantane-1-carboxamide;
292. (E)-4-{[2-(4-chlorophenoxy)-2-methylpropanoyl]amino}-N-(1,3-thiazol-5-ylmethyl)adamantine-1-carboxamide;
293. (E)-4-{[2-(4-chlorophenoxy)-2-methylpropanoyl]amino}-N-(pyridin-4-ylmethyl) adamantine-1-carboxamide;
294. (E)-4-{[2-(4-aminophenoxy)-2-methylpropanoyl]amino}adamantane-1-carboxamide;
295. (E)-4-({2-methyl-2-[2-(trifluoromethoxy)phenoxy]propanoyl}amino)adamantane-1-carboxamide;
296. (E)-4-({2-methyl-2-[2-(trifluoromethyl)phenoxy]propanoyl}amino)adamantane-1-carboxamide;
297. (E)-4-({2-methyl-2-[4-(pyrrolidin-1-ylsulfonyl)phenoxy]propanoyl}amino) adamantane-1-carboxamide;
298. 2-(2-chloro-4-fluorophenoxy)-N-[(E)-5-hydroxy-2-adamantyl]-2-methylpropanamide;
299. 2-(2-chloro-4-fluorophenoxy)-N-[(E)-5-cyano-2-adamantyl]-2-methylpropanamide;
300. (E)-4-[(2-methyl-2-{4-[(trifluoroacetyl)amino]phenoxy}propanoyl)amino]adamantane-1-carboxamide;
301. (E)-4-{[2-(3-bromo-4-methoxyphenoxy)-2-methylpropanoyl]amino}adamantane-1-carboxamide;
302. (E)-4-{[2-(2,5-dibromo-4-methoxyphenoxy)-2-methylpropanoyl]amino}adamantane-1-carboxamide;
303. (E)-4-{[2-(2-bromo-4-methoxyphenoxy)-2-methylpropanoyl]amino}adamantane-1-carboxamide;
304. (E)-4-{[2-(2-chloro-4-fluorophenoxy)-2-methylpropanoyl]amino}-N,N-dimethyladamantane-1-carboxamide;
305. 2-(4-chlorophenoxy)-N-((E)-5-{[(4-methoxy-6-methylpyrimidin-2-yl)amino]methyl}-2-adamantyl)-2-methylpropanamide;
306. (E)-4-{[2-(4-{[(tert-butylamino)carbonyl]amino}phenoxy)-2-methylpropanoyl]amino}adamantane-1-carboxamide;
307. ethyl 4-(2-{[(E)-5-(aminocarbonyl)-2-adamantyl]amino}-1,1-aimethyl-2-oxoethoxy)phenylcarbamate;
308. (E)-4-[(2-methyl-2-{4-[(propylsulfonyl)amino]phenoxy}propanoyl)amino]adamantane-1-carboxamide;
309. (E)-4-[(2-{4-[(3,3-dimethylbutanoyl)amino]phenoxy}-2-methylpropanoyl)amino]adamantane-1-carboxamide;
310. (E)-4-{[2-methyl-2-(phenylsulfinyl)propanoyl]amino}adamantane-1-carboxylic acid;
311. (E)-4-{[2-methyl-2-(phenylsulfonyl)propanoyl]amino}adamantane-1-carboxylic acid;
312. N-[(E)-5-cyano-2-adamantyl]-2-[(4-methoxyphenyl)sulfonyl]-2-methylpropanamide;
313. 2-[(4-methoxyphenyl)sulfonyl]-2-methyl-N-[(E)-5-(2H-tetrazol-5-yl)-2-adamantyl]propanamide;
314. (E)-4-({2-[4-(benzyloxy)phenoxy]-2-methylpropanoyl}amino)adamantane-1-carboxamide;
315. (E)-4-{[1-(4-chloro-phenyl)-cyclobutanecarbonyl]-amino}-adamantane-1-carboxylic acid;
316. (E)-4-[(1-phenyl-cyclopropanecarbonyl)-amino]-adamantane-1-carboxylic acid;
317. (E)-4-(2-methyl-2-phenyl-propionylamino)-adamantane-1-carboxylic acid;
318. (E)-4-{[1-(4-chloro-phenyl)-cyclobutanecarbonyl]-amino}-adamantane-1-carboxylic acid amide;
319. (E)-4-[(1-phenyl-cyclopropanecarbonyl)-amino]-adamantane-1-carboxylic acid amide;
320. (E)-4-(2-methyl-2-phenyl-propionylamino)-adamantane-1-carboxylic acid amide;
321. (E)-4-({[1-(4-chlorophenyl)cyclohexyl]carbonyl}amino)adamantane-1-carboxamide;
322. (E)-4-({[1-(4-chlorophenyl)cyclopropyl]carbonyl}amino)adamantane-1-carboxamide;
323. (E)-4-({[1-(4-chlorophenyl)cyclopentyl]carbonyl}amino)adamantane-1-carboxamide;
324. (E)-4-{[2-(4-chlorophenyl)-2-methylpropanoyl]amino}adamantane-1-carboxamide;
325. (E)-4-{[(1-phenylcyclopentyl)carbonyl]amino}adamantane-1-carboxamide;
326. (E)-4-({[1-(3-fluorophenyl)cyclopentyl]carbonyl}amino)adamantane-1-carboxamide;
327. (E)-4-({[1-(2-chloro-4-fluorophenyl)cyclopentyl]carbonyl}amino)adamantane-1-carboxamide;
328. (E)-4-({[1-(4-fluorophenyl)cyclopentyl]carbonyl}amino)adamantane-1-carboxamide;
329. (E)-4-({[1-(2-fluorophenyl)cyclopentyl]carbonyl}amino)adamantane-1-carboxamide;
330. (E)-4-{[(1-methylcyclohexyl)carbonyl]amino}adamantane-1-carboxamide;
331. (E)-4-({[1-(2,4-dichlorophenyl)cyclopropyl]carbonyl}amino)adamantane-1-carboxamide;
332. (E)-4-({[1-(4-methoxyphenyl)cyclopropyl]carbonyl}amino)adamantane-1-carboxamide;
333. (E)-4-({[1-(4-methylphenyl)cyclopropyl]carbonyl}amino)adamantane-1-carboxamide;
334. (E)-4-{[2-methyl-2-(4-pyridin-4-ylphenyl)propanoyl]amino}adamantane-1-carboxamide;
335. (E)-4-[(2-methyl-2-thien-2-ylpropanoyl)amino]adamantane-1-carboxamide;
336. (E)-4-[(2-methyl-2-thien-3-ylpropanoyl)amino]adamantane-1-carboxamide;
337. (E)-4-({2-methyl-2-[5-(trifluoromethyl)pyridin-2-yl]propanoyl}amino)adamantane-1-carboxamide;
338. (E)-4-[(2-methyl-2-{4-[5-(trifluoromethyl)pyridin-2-yl]phenyl}propanoyl)amino]adamantane-1-carboxamide;
339. (E)-4-({[1-(4-methoxyphenyl)cyclopentyl]carbonyl}amino)adamantane-1-carboxamide;
340. (E)-4-{[2-(4-bromophenyl)-2-methylpropanoyl]amino}adarnantane-1-carboxamide;
341. (E)-4-[5-(aminocarbonyl)-2-adamantyl]-3-methyl-1-(2-methylbenzyl)-2-oxopiperidine-3-carboxamide;
342. (E)-4-(aminocarbonyl)-2-adamantyl]-1-benzyl-3-methyl-2-oxopyrrolidine-3-carboxamide;
343. (E)-4-(aminocarbonyl)-2-adamantyl]-3-methyl-1-(2-methylbenzyl)-2-oxopyrrolidine-3-carboxamide;
344. (E)-4-(aminocarbonyl)-2-adamantyl]-1-(2-chlorobenzyl)-3-methyl-2-oxopyrrolidine-3-carboxamide;
345. (E)-4-(aminocarbonyl)-2-adamantyl]-1-(3-chlorobenzyl)-3-methyl-2-oxopyrrolidine-3-carboxamide;
346. (E)-4-({2-methyl-2-[4-(1-methyl-1H-pyrazol-4-yl)phenyl]propanoyl}amino) adamantane-1-carboxamide;
347. (E)-4-{[2-(3-bromophenyl)-2-methylpropanoyl]amino}adamantane-1-carboxamide;
348. (E)-4-({2-[4-(3,5-dimethylisoxazol-4-yl)phenyl]-2-methylpropanoyl}amino) adamantane-1-carboxamide;
349. (E)-4-{[2-methyl-2-(4-pyridin-3-ylphenyl)propanoyl]amino}adamantane-1-carboxamide;
350. 4-{[({(E)-4-[(2-methyl-2-thien-2-ylpropanoyl)amino]-1-adamantyl}carbonyl)amino]methyl}benzoic acid;
351. (E)-4-({2-methyl-2-[4-(1H-pyrazol-4-yl)phenyl]propanoyl}amino)adamantane-1-carboxamide;
352. (E)-4-(aminocarbonyl)-2-adamantyl]-3-methyl-1-(1-methyl-1-phenylethyl)-2-oxopyrrolidine-3-carboxamide;

353. (E)-4-(aminocarbonyl)-2-adamantyl]-3-methyl-2-oxo-1-[(1R)-1-phenylethyl]pyrrolidine-3-carboxamide;
354. (E)-4-(aminocarbonyl)-2-adamantyl]-3-methyl-2-oxo-1-[(1S)-1-phenylethyl]pyrrolidine-3-carboxamide;
355. (E)-4-{[2-methyl-2-(1,3-thiazol-2-yl)propanoyl]amino}adamantane-1-carboxamide;
356. (E)-4-(aminocarbonyl)-2-adamantyl]-1-(4-chlorobenzyl)-3-methylpiperidine-3-carboxamide;
357. (E)-4-{[2-(4-hydroxyphenyl)-2-methylpropanoyl]amino}adamantane-1-carboxamide;
358. (E)-4-(aminocarbonyl)-2-adamantyl]-1-benzyl-3-methyl-2-oxopiperidine-3-carboxamide;
359. (E)-4-{[2-methyl-2-(4-phenoxyphenyl)propanoyl]amino}adamantane-1-carboxamide;
360. (E)-4-{[2-(1-benzothien-3-yl)-2-methylpropanoyl]amino}adamantane-1-carboxamide;
361. (E)-4-{[2-(5-fluoropyridin-2-yl)-2-methylpropanoyl]amino}adamantane-1-carboxamide;
362. 6-[(1-cycloheptyl-4,4-dimethyl-5-oxopyrrolidin-3-yl)methoxy]nicotinonitrile;
363. 4-(4-{[(5-cyanopyridin-2-yl)oxy]methyl}-3,3-dimethyl-2-oxopyrrolidin-1-yl)azepane-1-carboxamide;
364. 1-cycloheptyl-3,3-dimethyl-4-(phenoxymethyl)pyrrolidin-2-one;
365. 1-cycloheptyl-4-{[(2-fluorophenyl)(methyl)amino]methyl}-3,3-dimethylpyrrolidin-2-one;
366. 6-{[1-(5-hydroxycyclooctyl)-4,4-dimethyl-5-oxopyrrolidin-3-yl]methoxy}nicotinonitrile;
367. (E)-4-(4-{[(5-cyanopyridin-2-yl)oxy]methyl}-3,3-dimethyl-2-oxopyrrolidin-1-yl) adamantine-1-carboxamide;
368. 9-(4-{[(5-cyanopyridin-2-yl)oxy]methyl}-3,3-dimethyl-2-oxopyrrolidin-1-yl)bicyclo[3.3.1]nonane-3-carboxamide;
369. trans ethyl (1R,7S)-4-(4-{[(5-cyanopyridin-2-yl)oxy]methyl}-3,3-dimethyl-2-oxopyrrolidin-1-yl)bicyclo[5.1.0]octane-8-carboxylate;
370. trans ethyl (1S,7R)-4-(4-{[(5-cyanopyridin-2-yl)oxy]methyl}-3,3-dimethyl-2-oxopyrrolidin-1-yl)bicyclo[5.1.0]octane-8-carboxylate;
371. 6-{[4,4-dimethyl-1-(4-methylbicyclo[2.2.2]oct-1-yl)-5-oxopyrrolidin-3-yl]methoxy}nicotinonitrile;
372. 6-{[1-(5-cyanocyclooctyl)-4,4-dimethyl-5-oxopyrrolidin-3-yl]methoxy}nicotinonitrile;
373. (E)-4-(4-{[(5-cyanopyridin-2-yl)oxy]methyl}-3,3-dimethyl-2-oxopyrrolidin-1-yl) adamantane-1-carbonitrile;
374. (E)-4-(3,3-dimethyl-2-oxo-4-{[4-(1H-1,2,4-triazol-1-yl)phenoxy]methyl}pyrrolidin-1-yl) adamantane-1-carboxamide;
375. (E)-4-(4-{[4-(1H-imidazol-1-yl)phenoxy]methyl}-3,3-dimethyl-2-oxopyrrolidin-1-yl)adamantane-1-carboxamide;
376. (E)-4-[3,3-dimethyl-2-oxo-4-({[5-(trifluoromethyl)pyridin-2-yl]oxy}methyl) pyrrolidin-1-yl]-N'-hydroxyadamantane-1-carboximidamide;
377. (E)-4-[3,3-dimethyl-2-oxo-4-({[5-(trifluoromethyl)pyridin-2-yl]oxy}methyl)pyrrolidin-1-yl]adamantane-1-carboxamide;
378. (E)-4-[3,3-dimethyl-2-oxo-4-({[5-(trifluoromethyl)pyridin-2-yl]oxy}methyl)pyrrolidin-1-yl]adamantane-1-carboximidamide;
379. 1-[(4-methylphenyl)sulfonyl]-4-(4-nitrobenzoyl)piperazine;
380. N-{1-[(1-cyanocyclopropyl)methyl]piperidin-4-yl}-N-cyclopropyl-4-(2,2,2-trifluoro-1-hydroxy-1-methylethyl)benzamide;
381. [4-(cyclopropyl{-4-[2,2,2-trifluoro-1-hydroxy-1-methylethyl]benzoyl}amino)-1-(4-fluorophenyl)cyclohexyl]methyl carbamate;
382. N-cyclopropyl-N-[4-(2-hydroxyethyl)cyclohexyl]-4-isopropylbenzamide;
383. 3-(1-{[5-(4-methylphenyl)isoxazol-4-yl]carbonyl}pyrrolidin-3-yl)pyridine;
384. 4-[4-[(1-adamantylamino)carbonyl]-5-(1-methylcyclopropyl)-1H-pyrazol-1-yl]benzoic acid;
385. N-cyclohexyl-2-[(2-phenylethyl)thio]nicotinamide;
386. 4-[5-[(2-adamantylamino)carbonyl]-6-(propylthio)pyridin-2-yl]morpholine-2-carboxylic acid;
387. N-cyclopropyl-N-(4-cyclopropyl-4-hydroxycyclohexyl)-4-[2,2,2-trifluoro-1-hydroxy-1-methylethyl]benzamide;
388. 1-{[2-(4-fluorophenyl)-6-hydroxy-2-adamantyl]acetyl}azetidin-3-ol;
389. N-(2-adamantyl)-2-[1-(2-(isobutylamino)-2-oxoethyl)cyclopentyl]acetamide;
390. 1-({4-[(2-fluorophenyl)sulfonyl]-1,4-diazepan-1-yl}acetyl)decahydroquinoline;
391. cyclohexyl-3-[(3,5-dichloro-4'-{[4-(2-fluoroethyl)piperazin-1-yl]carbonyl}-1,1'-biphenyl-4-yl)methyl]pyrrolidin-2-one;
392. 3-[(3,5-dichloro-4'-{[4-(trifluoromethyl)piperidin-1-yl]carbonyl}-1,1'-biphenyl-4-yl)methyl]-1-piperidin-1-ylpyrrolidin-2-one;
393. 3-cyclohexyl-1-[(3,5-dichloro-4'-{[4-(2-fluoroethyl)piperazin-1-yl]carbonyl}-1,1'-biphenyl-4-yl)methyl]pyrrolidin-2-one;
394. 3-[(3,5-dichloro-4'-{[4-(trifluoromethyl)piperidin-1-yl]carbonyl}-1,1'-biphenyl-4-yl)methyl]-1-(4,4-difluorocyclohexyl)pyrrolidin-2-one;
395. 3-[(3,5-dichloro-4'-fluoro-1,1'-biphenyl-4-yl)methyl]-1-(4,4-difluorocyclohexyl)pyrrolidin-2-one;
396. 3-[(3,5-dichloro-4'-{[4-(trifluoromethyl)piperidin-1-yl]carbonyl}-1,1'-biphenyl-4-yl)methyl]-1-(4-hydroxypiperidin-1-yl)pyrrolidin-2-one;
397. methyl 4-{3-[(3,5-dichloro-4'-{[4-(trifluoromethyl)piperidin-1-yl]carbonyl}-1,1'-biphenyl-4-yl)methyl]-2-oxopyrrolidin-1-yl}piperidine-1-carboxylate;
398. 2-[(3,5-dichloro-4'-{[4-(trifluoromethyl)piperidin-1-yl]carbonyl}-1,1'-biphenyl-4-yl)methyl]-2-azaspiro[4.5]decan-1-one;
399. 3-[(3,5-dichloro-4'-{[4-(trifluoromethyl)piperidin-1-yl]carbonyl}-1,1'-biphenyl-4-yl)methyl]-1-(4,5,6,7-tetrahydro-1H-benzimidazol-6-yl)pyrrolidin-2-one;
400. 3-[(3,5-dichloro-4'-fluoro-1,1'-biphenyl-4-yl)methyl]-1-[(5S)-4,5,6,7-tetrahydro-2H-indazol-5-yl]pyrrolidin-2-one;
401. N-2-adamantyl-2'-tert-butyl-2'H-1,3'-bipyrazole-4'-carboxamide;
402. 1'-[(4-bromo-2-fluorophenyl)(hydroxy)acetyl]-3H-spiro[2-benzofuran-1,3'-pyrrolidin]-3-one;
403. N-(1-{[4-(2,5-dimethylphenyl)piperazin-1-yl]carbonyl}piperidin-3-yl)-4-hydroxyadamantane-1-carboxamide;
404. 7-acetyl-3-[1-(4-chlorophenyl)cyclopropyl]-1-oxa-2,7-diazaspiro[4.4]non-2-ene;
405. 7-(2-chlorophenyl)-1-isobutyl-1,7-diazaspiro[4.4]nonan-6-one;
406. 8-(3-chloropyridin-2-yl)-2-cyclohexyl-2,8-diazaspiro[4.5]decan-1-one;
407. 5-{3-fluoro-4-[2-(4-hydroxycyclohexyl)-1-oxo-2,7-diazaspiro[4.5]dec-7-yl]phenyl}-N,N-dimethylpyridine-2-carboxamide;

408. 2-(2-acetylphenyl)-N-cyclooctyl-1,3-thiazole-4-carboxamide;
409. 4-[5-cyclopropyl-4-({3-[2-(trifluoromethyl)phenyl]pyrrolidin-1-yl}carbonyl)-1H-pyrazol-1-yl]piperidine;
410. 2-(4-{2-[(4-chlorobenzoyl)amino]ethyl}phenoxy)-2-methylpropanoic acid;
411. 1'-{[2-(trifluoromethyl)phenoxy]acetyl}spiro[indole-3,4'-piperidin]-2(1H)-one;
412. 1-{4-[(2-adamantylamino)carbonyl]phenyl}piperidine-4-carboxylic acid;
413. N-{1-[4-(3-azabicyclo[3.2.2]non-3-ylcarbonyl)phenyl]pyrrolidin-3-yl}-N-methyl-1-phenylmethanesulfonamide;
414. 1-(1-adamantylcarbonyl)-4-[2-(1H-imidazol-2-ylthio)ethyl]piperidine;
415. N-2-adamantyl-4-[2-oxa-5-azabicyclo[2.2.1]hept-5-yl]benzamide;
416. 1,1,1-trifluoro-N-isopropy 1-N-(4-{[1,3,3-trimethyl-6-azabicyclo[3.2.1]oct-6-yl]carbonyl}benzyl)methanesulfonamide;
417. acetyl-N-[2-(5-{[1,3,3-trimethyl-6-azabicyclo[3.2.1]oct-6-yl]carbonyl}-1H-benzimidazol-1-yl)ethyl]piperidine-4-carboxamide;
418. ethyl 3-(4-{[1,3,3-trimethyl-6-azabicyclo[3.2.1]oct-6-yl]carbonyl}-1H-indol-1-yl)propanoate;
419. N-1-adamantyl-1-(thien-2-ylsulfonyl)piperidine-4-carboxamide;
420. 4-(2,4-dichlorophenoxy)-N-[4-(hydroxymethyl)-2-adamantyl]butanamide;
421. 4-[(5-chloropyridin-2-yl)oxy]-N-[4-(hydroxymethyl)cyclohexyl]-N-methylbenzamide;
422. $N^1$-2-adamantyl-$N^2$-cyclohexyl-$N^2$-methylglycinamide;
423. $N^2$-adamantyl-1-methyl-5-(2-phenylethoxy)-1H-pyrazole-4-carboxamide;
424. 4-(cyclopentylthio)-3-({[4(2,4-dichlorobenzoyl)amino]cyclopropyl}methoxy)-N-[5-hydroxy-2-adamantyl]isoxazole-5-carboxamide;
425. 4-[({1-[3-cyano-3-methylbut-1-enyl]-5-isobutoxy-1H-pyrazol-4-yl}carbonyl)amino]-1-adamantyl carbamate;
426. 2-(-5-hydroxy-2-adamantyl)-1H-isoindole-1,3(2H)-dione and 2-(6-hydroxy-2-adamantyl)-1H-isoindole-1,3(2H)-dione;
427. N-(5-hydroxy-2-adamantyl)-4-[(pyridin-2-ylsulfonyl)methoxy]benzamide;
428. 3-(cyclohexylmethoxy)-N-[5-(hydroxymethyl)-2-adamantyl]benzamide;
429. N-3-hydroxy-1-adamantyl]-4-[(methylsulfonyl)methoxy]benzamide;
430. N-(5-hydroxy-2-adamantyl)-N-methyl-3-(2-phenylethoxy)benzamide;
431. 8-[(9-methyl-9H-carbazol-3-yl)carbonyl]-8-azabicyclo[3.2.1]octan-3-ol;
1-acetyl-N-[2-(4-chlorophenoxy)phenyl]piperidin-4-amine;
432. {4-[(4-methylphenyl)sulfonyl]piperazin-1-yl}(4-nitrophenyl)methylenecyanamide;
433. N'-cyano-N-{1-[(1-cyanocyclopropyl)methyl]piperidin-4-yl}-N-cyclopropyl-4-(2,2,2-trifluoro-1-hydroxy-1-methylethyl)benzenecarboximidamide;
434. [4-[{(cyanoimino)[4-(2,2,2-trifluoro-1-hydroxy-1-methylethyl)phenyl]methyl}(cyclopropyl)amino]-1-(4-fluorophenyl)cyclohexyl]methyl carbamate;
435. N'-cyano-N-cyclopropyl-N-[4-(2-hydroxyethyl)cyclohexyl]-4-isopropylbenzenecarboximidamide[5-(4-methylphenyl)isoxazol-4-yl](3-pyridin-3-ylpyrrolidin-1-yl)methylenecyanamide;

437. 4-[4-[(1-adamantylamino)(cyanoimino)methyl]-5-(1-methylcyclopropyl)-1H-pyrazol-1-yl]benzoic acid;
438. N'-cyano-N-cyclohexyl-2-[(2-phenylethypthio]pyridine-3-carboximidamide;
439. 4-[5-[(2-adamantylamino)(cyanoimino)methyl]-6-(propylthio)pyridin-2-yl]morpholine-2-carboxylic acid;
440. N'-cyano-N-cyclopropyl-N-(4-cyclopropyl-4-hydroxycyclohexyl)-4-(2,2,2-trifluoro-1-hydroxy-1-methylethyl)benzenecarboximidamide;
441. 2-[2-(4-fluorophenyl)-6-hydroxy-2-adamantyl]-1-(3-hydroxyazetidin-1-yl)ethylidenecyanamide;
442. 2-{1-[2-(2-adamantylamino)-2-(cyanoimino)ethyl]cyclopentyl}-N-isobutylacetamide;
443. 2-{4-[(2-fluorophenyl)sulfonyl]-1,4-diazepan-1-yl}-1-octahydroquinolin-1(2H)-ylethylidenecyanamide;
444. cyclohexyl-3-[(3,5-dichloro-4'-{[4-(2-fluoroethyl)piperazin-1-yl]carbonyl}-1,1'-biphenyl-4-yl)methyl]pyrrolidin-2-ylidenecyanamide;
445. 3-[(3,5-dichloro-4'-{[4-(trifluoromethyl)piperidin-1-yl]carbonyl}-1,1'-biphenyl-4-yl)methyl]-1-piperidin-1-ylpyrrolidin-2-ylidenecyanamide;
446. 3-cyclohexyl-1-[(3,5-dichloro-4'-{[4(2-fluoroethyl)piperazin-1-yl]carbonyl}-1,1'-biphenyl-4-yl)methyl]pyrrolidin-2-ylidenecyanamide;
447. 3-[(3,5-dichloro-4'-{[4-(trifluoromethyl)piperidin-1-yl]carbonyl}-1,1'-biphenyl-4-yl)methyl]-1-(4,4-difluorocyclohexyl)pyrrolidin-2-ylidenecyanamide;
448. 3-[(3,5-dichloro-4'-fluoro-1,1'-biphenyl-4-yl)methyl]-1-(4,4-difluorocyclohexyl)pyrrolidin-2-ylidenecyanamide;
449. 3-[(3,5-dichloro-4'-{[4-(trifluoromethyl)piperidin-1-yl]carbonyl}-1,1'-biphenyl-4-yl)methyl]-1-(4-hydroxypiperidin-1-yl)pyrrolidin-2-ylidenecyanamide;
450. methyl 4-{2-(cyanoimino)-3-[(3,5-dichloro-4'-{[4-(trifluoromethyl)piperidin-1-yl]carbonyl}-1,1'-biphenyl-4-yl)methyl]pyrrolidin-1-yl}piperidine-1-carboxylate;
451. 2-[(3,5-dichloro-4'-{[4-(trifluoromethyl)piperidin-1-yl]carbonyl}-1,1'-biphenyl-4-yl)methyl]-2-azaspiro[4.5]dec-1-ylidenecyanamide;
452. 3-[(3,5-dichloro-4'-{[4-(trifluoromethyl)piperidin-1-yl]carbonyl}-1,1'-biphenyl-4-yl)methyl]-1-(4,5,6,7-tetrahydro-1H-benzimidazol-6-yl)pyrrolidin-2-ylidenecyanamide;
453. 3-[(3,5-dichloro-4'-fluoro-1,1'-biphenyl-4-yl)methyl]-1-(4,5,6,7-tetrahydro-2H-indazol-5-yl)pyrrolidin-2-ylidenecyanamide;
454. N-2-adamantyl-2'-tert-butyl-N'-cyano-2'H-1,3'-bipyrazole-4'-carboximidamide;
455. 2-(4-bromo-2-fluorophenyl)-2-hydroxy-1-(3-oxo-1'H,3H-spiro[2-benzofuran-1,3'-pyrrolidin]-1'-yl)ethylidenecyanamide;
456. N'-cyano-N-(1-{[4-(2,5-dimethylphenyl)piperazin-1-yl]carbonyl}piperidin-3-yl)-4-hydroxyadamantane-1-carboximidamide;
457. 1-{3-[1-(4-chlorophenyl)cyclopropyl]-1-oxa-2,7-diazaspiro[4.4]non-2-en-7-yl}ethylidenecyanamide;
458. 7-(2-chlorophenyl)-1-isobutyl-1,7-diazaspiro[4.4]non-6-ylidenecyanamide;
459. 8-(3-chloropyridin-2-yl)-2-cyclohexyl-2,8-diazaspiro[4.5]dec-1-ylidenecyanamide;
460. 5-{4-[1-(cyanoimino)-2-(4-hydroxycyclohexyl)-2,7-diazaspiro[4.5]dec-7-yl]-3-fluorophenyl}-N,N-dimethylpyridine-2-carboxamide;
461. 2-(2-acetylphenyl)-N'-cyano-N-cyclooctyl-1,3-thiazole-4-carboximidamide;

462. (5-cyclopropyl-1-piperidin-4-yl-1H-pyrazol-4-yl){3-[2-(trifluoromethyl)phenyl]pyrrolidin-1-yl}methylenecyanamide;

463. 2-[4-(2-{[(4-chlorophenyl)(cyanoimino)methyl]amino}ethyl)phenoxy]-2-methylpropanoic acid;

464. 1'-{[2-(trifluoromethyl)phenoxy]acetyl}spiro[indole-3,4'-piperidin]-2(1H)-ylidenecyanamide;

465. 1-{4-[(2-adamantylamino)(cyanoimino)methyl]phenyl}piperidine-4-carboxylic acid;

466. N-(1-{4-[3-azabicyclo[3.2.2]non-3-yl(cyanoimino)methyl]phenyl}pyrrolidin-3-yl)-N-methyl-1-phenyl-methanesulfonamide;

467. adamantyl {4-[2-(1H-imidazol-2-ylthio)ethyl]piperidin-1-yl}methylenecyanamide;

468. N-2-adamantyl-N'-cyano-4-(2-oxa-5-azabicyclo[2.2.1]hept-5-yl)benzenecarboximidamide;

469. N-{4-[(cyanoimino)(1,3,3-trimethyl-6-azabicyclo[3.2.1]oct-6-yl)methyl]benzyl}-1,1,1-trifluoro-N-isopropylmethanesulfonamide;

470. acetyl-N-(2-{5-[(cyanoimino)(1,3,3-trimethyl-6-azabicyclo[3.2.1]oct-6-yl)methyl]-1H-benzimidazol-1-yl}ethyl)piperidine-4-carboxamide;

471. ethyl 3-{4-[(cyanoimino)(1,3,3-trimethyl-6-azabicyclo[3.2.1]oct-6-yl)methyl]-1H-indol-1-yl}propanoate;

472. N-1-adamantyl-N'-cyano-1-(thien-2-ylsulfonyl)piperidine-4-carboximidamide;

473. N'-cyano-4-(2,4-dichlorophenoxy)-N-[4-(hydroxymethyl)-2-adamantyl]butanimidamide;

474. 4-[(5-chloropyridin-2-yl)oxy]-N'-cyano-N-[4-(hydroxymethyl)cyclohexyl]-N-methylbenzenecarboximidamide;

475. N-2-adamantyl-N'-cyano-2-[cyclohexyl(methyl)amino]ethanimidamide;

476. N-2-adamantyl-N-cyano-1-methyl-5-(2-phenylethoxy)-1H-pyrazole-4-carboximidamide;

477. 2,4-dichloro-N-[1-({[5-{(cyanoimino)[(5-hydroxy-2-adamantyl)amino]methyl}-4-(cyclopentylthio)isoxazol-3-yl]oxy}methyl)cyclopropyl]benzamide;

478. 4-[((cyanoimino){1-[3-cyano-3-methylbut-1-enyl]-5-isobutoxy-1H-pyrazol-4-yl}methyl)amino]-1-adamantyl-carbamate;

479. 2-(5-hydroxy-2-adamantyl)-3-oxo-2,3-dihydro-1H-isoindol-1-ylidenecyanamide and 2-(6-hydroxy-2-adamantyl)-3-oxo-2,3-dihydro-1H-isoindol-1-ylidenecyanamide;

480. N'-cyano-N-(5-hydroxy-2-adamantyl)-4-[(pyridin-2-ylsulfonyl)methoxy]benzenecarboximidamide;

481. N'-cyano-3-(cyclohexylmethoxy)-N-[5-(hydroxymethyl)-2-adamantyl]benzene carboximidamide;

482. N'-cyano-N-(3-hydroxy-1-adamantyl)-4-[(methylsulfonyl)methoxy]benzene carboximidamide;

483. N'-cyano-N-(5-hydroxy-2-adamantyl)-N-methyl-3-(2-phenylethoxy)benzene carboximidamide;

484. (3-hydroxy-8-azabicyclo[3.2.1]oct-8-yl)(9-methyl-9H-carbazol-3-yl)methylene cyanamide; and 485. acetyl-N-[2-(4-chlorophenoxy)phenyl]piperidin-4-amine.

Another embodiment is a method comprising administering an 11-β-HSD-1 inhibitor listed in tables 1-6.

TABLE 1

| | 11βHSD-1 Inhibitors (Barf, T. et al., *Drugs of the Future*, 31(3), 231-243 (2006)) | |
|---|---|---|
| Example | Structure | IC$_{50}$ |

486

487

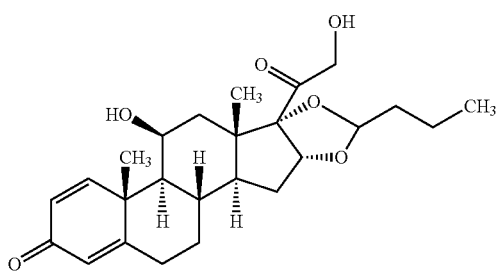

TABLE 1-continued

11βHSD-1 Inhibitors (Barf, T. et al., *Drugs of the Future*, 31(3), 231-243 (2006)

| Example | Structure | $IC_{50}$ |
|---------|-----------|-----------|
| 488 | 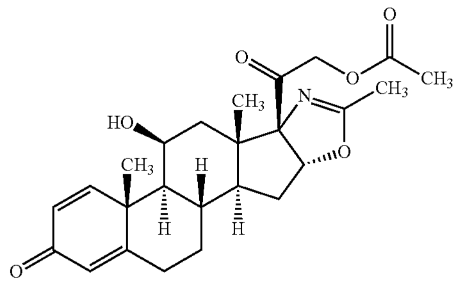 | |
| 489 | 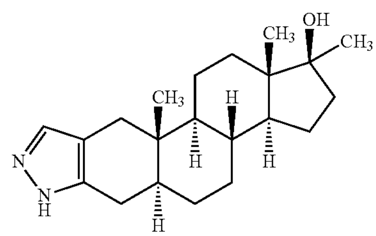 | |
| 490 | 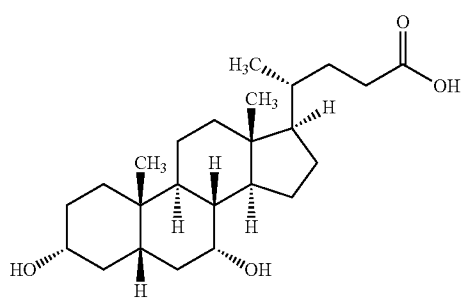 | 2.8 μM |
| 491 | 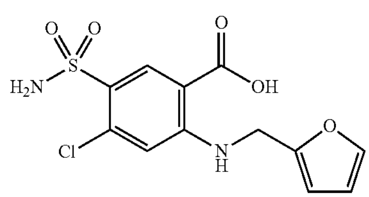 [SMILES: NS(=O)(=O)c1cc(C(=O)O)c(NCc2ccco2)cc1Cl] | 0.55 μM |
| 492-495 | 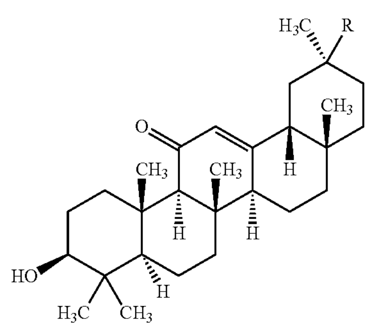 | 1.87 μM (7)<br>17 nM (10) |

(492) R = COOH
(493) R = CONHCH$_2$CH$_2$OH
(494) R = CONHCH$_2$CH$_2$OH
(495) R = CONHCH$_2$C$_6$H$_5$

TABLE 1-continued

11βHSD-1 Inhibitors (Barf, T. et al., *Drugs of the Future*, 31(3), 231-243 (2006))

| Example | Structure | IC$_{50}$ |
|---------|-----------|-----------|
| 496 | 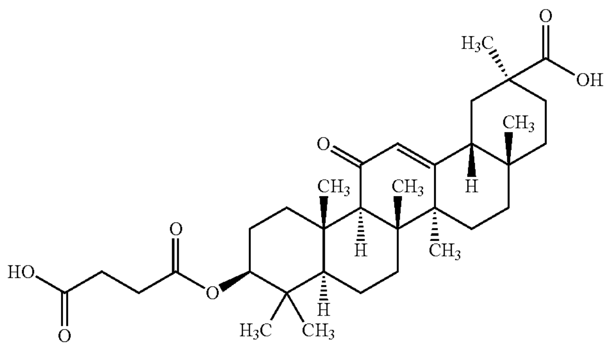 | 330 nM |
| 497-498 | (497) R = H<br>(498) R = OH | 18 μM (12)<br>10 μM (13) |
| 499 | 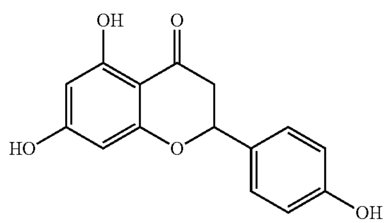 [SMILES: O=C1CC(c2ccc(O)cc2)Oc2cc(O)cc(O)c21] | |
| 500 | 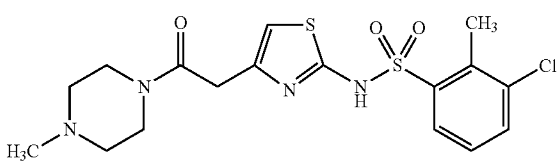 [SMILES: Cc1c(Cl)cccc1S(=O)(=O)Nc1nc(CC(=O)N2CCN(C)CC2)cs1] | 96 nM |
| 501 | 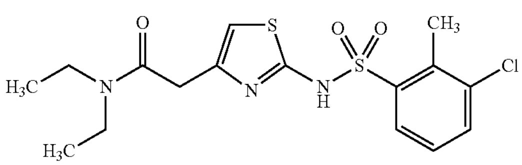 [SMILES: CCN(CC)C(=O)Cc1csc(NS(=O)(=O)c2cccc(Cl)c2C)n1] | 52 nM |
| 502 | 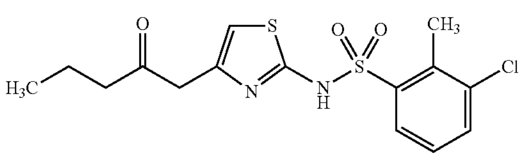 [SMILES: CCCC(=O)Cc1csc(NS(=O)(=O)c2cccc(Cl)c2C)n1] | 14 nM |
| 503 | 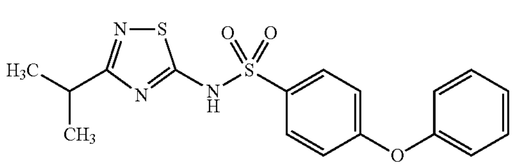 [SMILES: CC(C)c1nsc(NS(=O)(=O)c2ccc(Oc3ccccc3)cc2)n1] | 219 nM |

TABLE 1-continued

11βHSD-1 Inhibitors (Barf, T. et al., *Drugs of the Future*, 31(3), 231-243 (2006))

| Example | Structure | IC$_{50}$ |
|---|---|---|
| 504 | 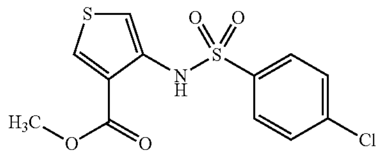 [SMILES: COC(=O)c1cscc1NS(=O)(=O)c1ccc(Cl)cc1] | |
| 505 | 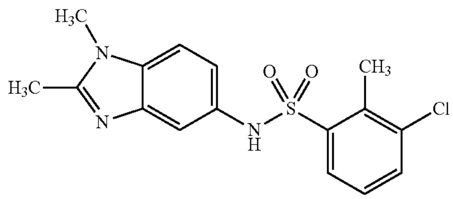 [SMILES: Cc1c(Cl)cccc1S(=O)(=O)Nc1ccc2c(c1)nc(C)n2C] | 110% @ 10 μM |
| 506 | 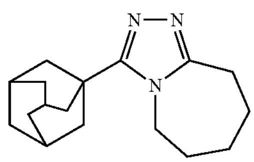 [SMILES: C1CCc2nnc(C34CC5CC(CC(C5)C3)C4)n2CC1] | 7.5 nM |
| 507 | 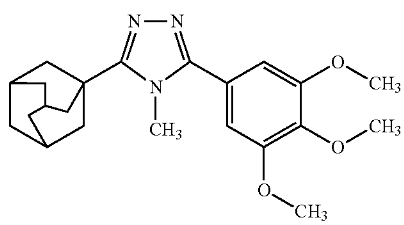 [SMILES: COc1cc(-c2nnc(C34CC5CC(CC(C5)C3)C4)n2C)cc(OC)c1OC] | <10 nM |
| 508 | 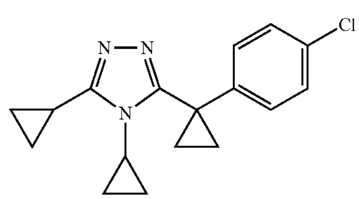 [SMILES: Clc1ccc(C2(c3nnc(C4CC4)n3C3CC3)CC2)cc1] | |
| 509 | 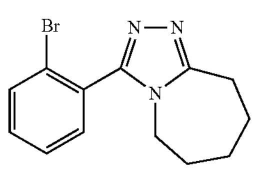 [SMILES: Brc1ccccc1-c1nnc2n1CCCCC2] | 230 nM |
| 510 | 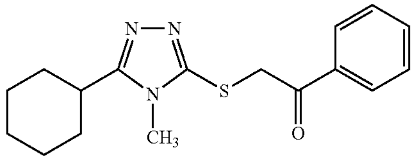 [SMILES: Cn1c(SCC(=O)c2ccccc2)nnc1C1CCCCC1] | 190 nM |
| 511 | 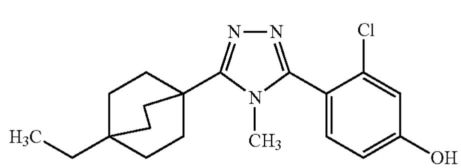 [SMILES: CCC12CCC(c3nnc(-c4ccc(O)cc4Cl)n3C)(CC1)CC2] | |

TABLE 1-continued

11βHSD-1 Inhibitors (Barf, T. et al., *Drugs of the Future*, 31(3), 231-243 (2006))

| Example | Structure | IC$_{50}$ |
|---------|-----------|-----------|
| 512 | 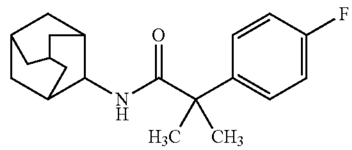 [SMILES: CC(C)(C(=O)NC1C2CC3CC(C2)CC1C3)c1ccc(F)cc1] | <1 μM |
| 513 | 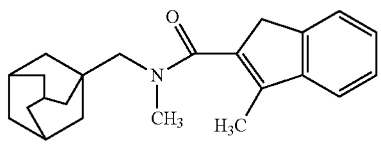 [SMILES: CC1=C(C(=O)N(C)CC23CC4CC(CC(C4)C2)C3)Cc2ccccc21] | 6.5 nM |
| 514 | 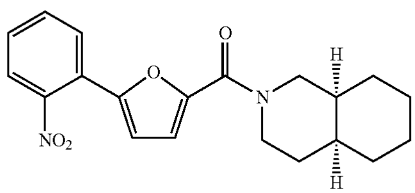 [SMILES: O=C(c1ccc(-c2ccccc2[N+](=O)[O-])o1)N1CC[C@@H]2CCCC[C@@H]2C1] | 7.7 nM |
| 515 | 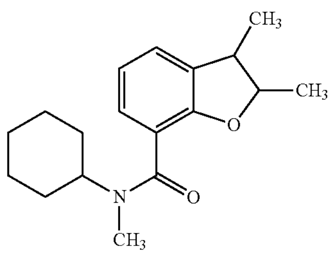 [SMILES: CC1Oc2c(C(=O)N(C)C3CCCCC3)cccc2C1C] | 6 nM |
| 516 | 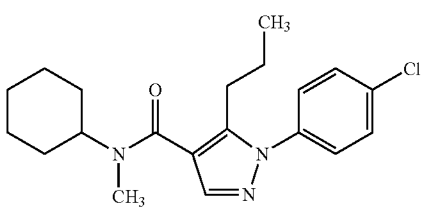 [SMILES: CCCc1c(C(=O)N(C)C2CCCCC2)cnn1-c1ccc(Cl)cc1] | 40 nM |
| 517 | 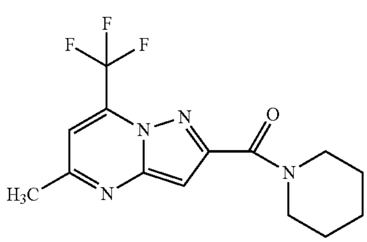 [SMILES: Cc1cc(C(F)(F)F)n2nc(C(=O)N3CCCCC3)cc2n1] | |
| 518 | 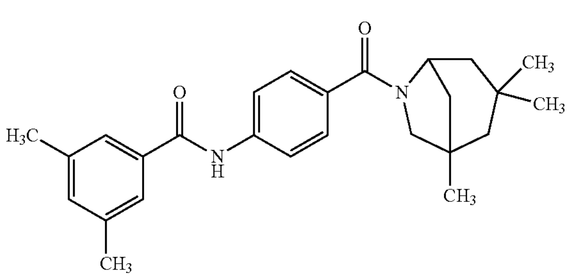 | |

TABLE 1-continued

11βHSD-1 Inhibitors (Barf, T. et al., *Drugs of the Future*, 31(3), 231-243 (2006))

| Example | Structure | IC$_{50}$ |
|---|---|---|
| 519 | 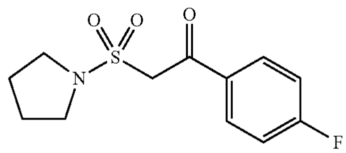 [SMILES: O=C(CS(=O)(=O)N1CCCC1)c1ccc(F)cc1] | 94 nM |
| 520 | 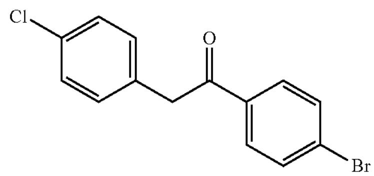 [SMILES: O=C(Cc1ccc(Cl)cc1)c1ccc(Br)cc1] | 77 nM |
| 521 | 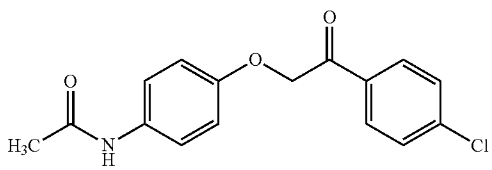 [SMILES: CC(=O)Nc1ccc(OCC(=O)c2ccc(Cl)cc2)cc1] | 153 nM |
| 522 | 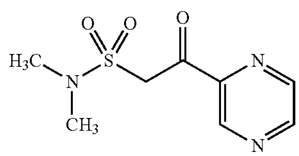 | 47 nM |
| 523 | 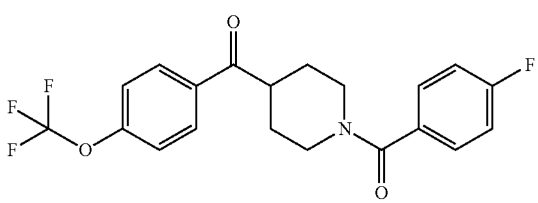 [SMILES: O=C(c1ccc(OC(F)(F)F)cc1)C1CCN(C(=O)c2ccc(F)cc2)CC1] | 50 nM |
| 524 | 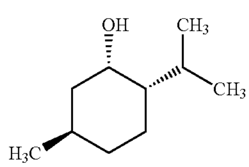 | 35 μM |
| 525 | 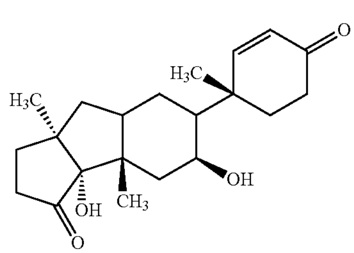 [SMILES: C[C@@]12CCC(=O)[C@]1(O)[C@@]1(C)C[C@H](O)C([C@]3(C)C=CC(=O)CC3)CC1C2] | |

TABLE 2

11βHSD-1 Inhibitors (Hughes, K. A., et al., *Expert Opin. Investig. Drugs*, 17(4), 481-496 (2008).

| Example | Structure | IC$_{50}$ |
|---------|-----------|-----------|
| 526 | 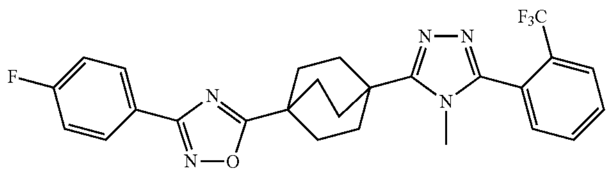 [SMILES: Cn1c(-c2ccccc2C(F)(F)F)nnc1C12CCC(c3nc(-c4ccc(F)cc4)no3)(CC1)CC2] | 2.2 nM |
| 527 | 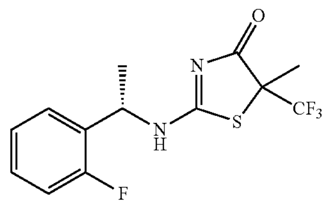 [SMILES: C[C@H](NC1=NC(=O)C(C)(C(F)(F)F)S1)c1ccccc1F] | 33 nM |
| 528 | 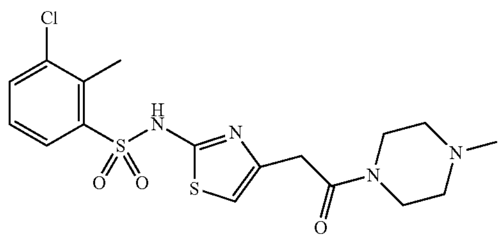 [SMILES: Cc1c(Cl)cccc1S(=O)(=O)Nc1nc(CC(=O)N2CCN(C)CC2)cs1] | 96 nM |
| 529 | 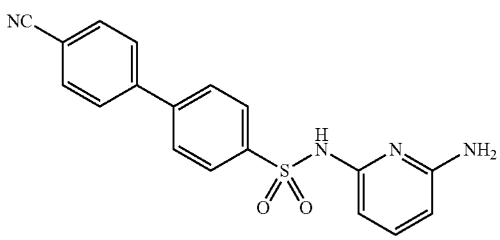 [SMILES: N#Cc1ccc(-c2ccc(S(=O)(=O)Nc3cccc(N)n3)cc2)cc1] | 15 nM |

TABLE 3

11βHSD-1 Inhibitors (Boyle, C. D. et al., *Expert Opin. Ther. Patents*, 19(6), 801-825 (2009)

| Example | Structure | IC$_{50}$ |
|---------|-----------|-----------|
| 530 | 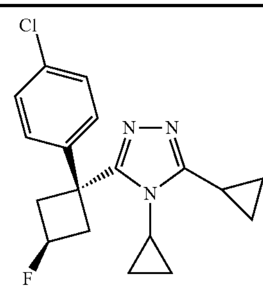 | |
| 531 | 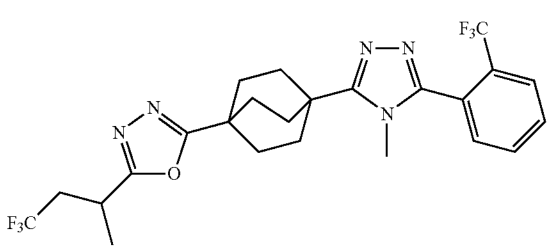 [SMILES: CC(CC(F)(F)F)c1nnc(C23CCC(c4nnc(-c5ccccc5C(F)(F)F)n4C)(CC2)CC3)o1] | 9-100 nM |

TABLE 3-continued

11βHSD-1 Inhibitors (Boyle, C. D. et al., *Expert Opin. Ther. Patents*, 19(6), 801-825 (2009))

| Example | Structure | IC$_{50}$ |
|---|---|---|
| 532 | 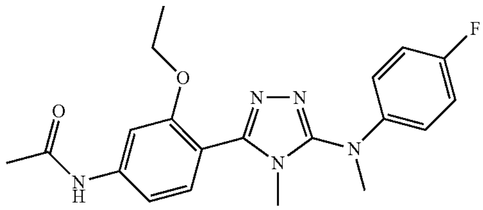 [SMILES: CCOc1cc(NC(C)=O)ccc1-c1nnc(N(C)c2ccc(F)cc2)n1C] | 3.4 nM |
| 533 | 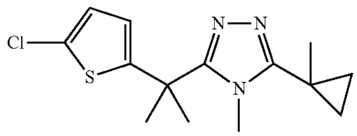 [SMILES: Cn1c(C2(C)CC2)nnc1C(C)(C)c1ccc(Cl)s1] | 2.4 nM |
| 534 | 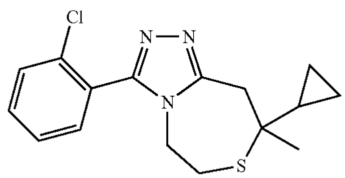 [SMILES: CC1(C2CC2)Cc2nnc(-c3ccccc3Cl)n2CCS1] | 71.8% @ 39 nM |
| 535 | 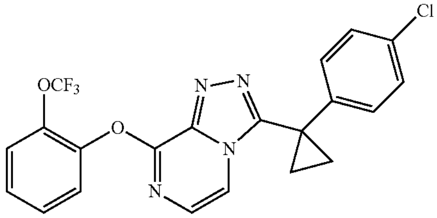 [SMILES: FC(F)(F)Oc1ccccc1Oc1nccn2c(C3(c4ccc(Cl)cc4)CC3)nnc12] | 0.5 nM |
| 536 | 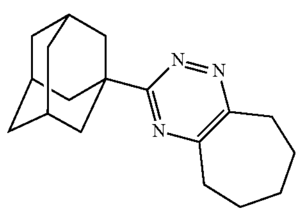 [SMILES: C1CCc2nnc(C34CC5CC(CC(C5)C3)C4)nc2CC1] | |
| 537 | 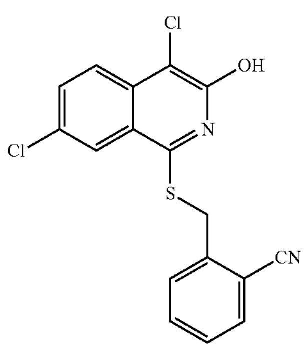 [SMILES: N#Cc1ccccc1CSc1nc(O)c(Cl)c2ccc(Cl)cc12] | 2 nM |
| 538 | 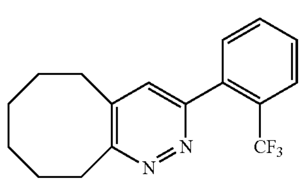 [SMILES: FC(F)(F)c1ccccc1-c1cc2c(nn1)CCCCCC2] | 3 nM |

TABLE 3-continued

11βHSD-1 Inhibitors (Boyle, C. D. et al., *Expert Opin. Ther. Patents*, 19(6), 801-825 (2009))

| Example | Structure | $IC_{50}$ |
|---|---|---|
| 539 | 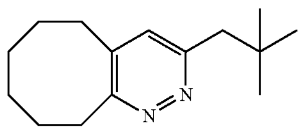 [SMILES: CC(C)(C)Cc1cc2c(nn1)CCCCCC2] | 6 nM |
| 540 | 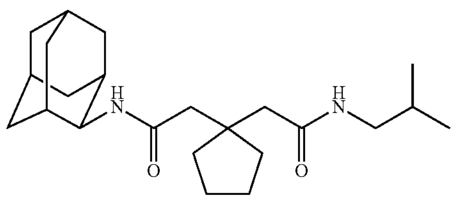 [SMILES: CC(C)CNC(=O)CC1(CC(=O)NC2C3CC4CC(C3)CC2C4)CCCC1] | 9 nM |
| 541 | 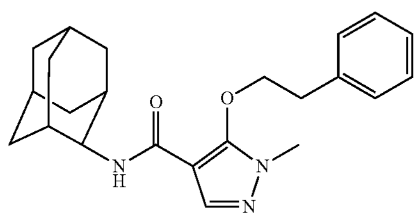 [SMILES: Cn1ncc(C(=O)NC2C3CC4CC(C3)CC2C4)c1OCCc1ccccc1] | 18 nM |
| 542 | 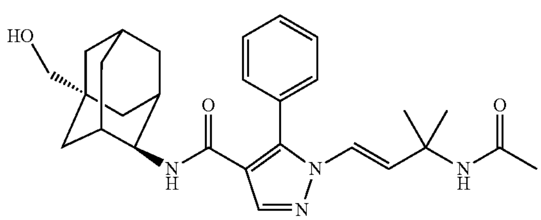 [SMILES: CC(=O)NC(C)(C)/C=C/n1ncc(C(=O)N[C@H]2C3CC4CC2C[C@](CO)(C4)C3)c1-c1ccccc1] | 20.8 nM |
| 543 | 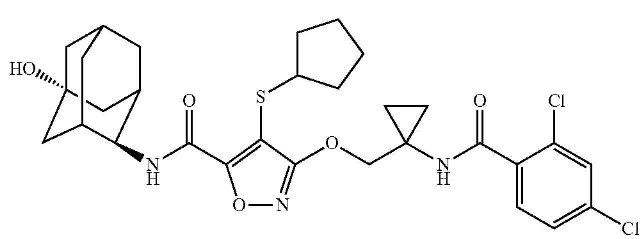 [SMILES: O=C(NC1(COc2noc(C(=O)N[C@H]3C4CC5CC3C[C@](O)(C5)C4)c2SC2CCCC2)CC1)c1ccc(Cl)cc1Cl] | 10 nM |
| 544 | 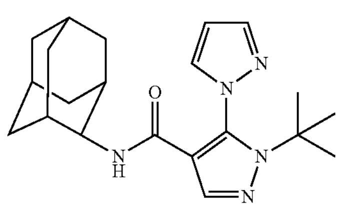 [SMILES: CC(C)(C)n1ncc(C(=O)NC2C3CC4CC(C3)CC2C4)c1-n1cccn1] | 6.8 nM |

TABLE 3-continued

11βHSD-1 Inhibitors (Boyle, C. D. et al., *Expert Opin. Ther. Patents*, 19(6), 801-825 (2009))

| Example | Structure | IC$_{50}$ |
|---|---|---|
| 545 | 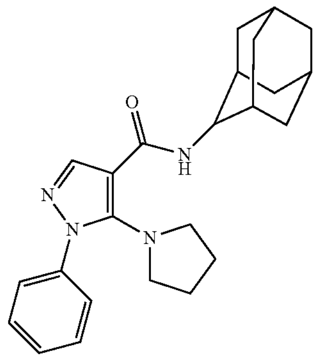 [SMILES: O=C(NC1C2CC3CC(C2)CC1C3)c1cnn(-c2ccccc2)c1N1CCCC1] | 0.55 nM |
| 546 | 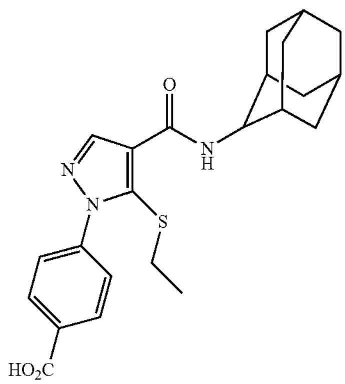 [SMILES: CCSc1c(C(=O)NC2C3CC4CC(C3)CC2C4)cnn1-c1ccc(C(=O)O)cc1] | 3 nM |
| 547 | 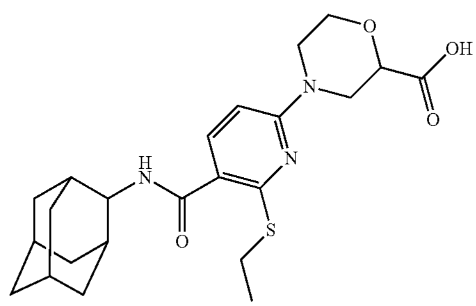 [SMILES: CCSc1nc(N2CCOC(C(=O)O)C2)ccc1C(=O)NC1C2CC3CC(C2)CC1C3] | 6 nM |
| 548 | 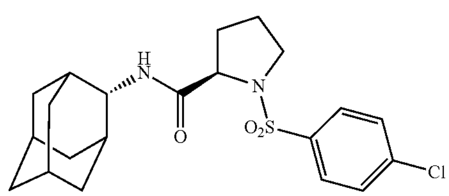 | <0.03 nM |
| 549 | 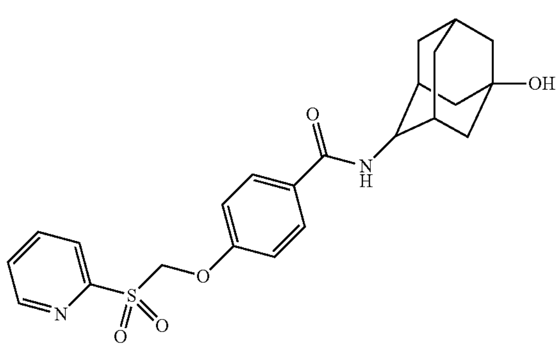 [SMILES: O=C(NC1C2CC3CC1CC(O)(C3)C2)c1ccc(OCS(=O)(=O)c2ccccn2)cc1] | |

TABLE 3-continued

11βHSD-1 Inhibitors (Boyle, C. D. et al., *Expert Opin. Ther. Patents*, 19(6), 801-825 (2009))

| Example | Structure | IC$_{50}$ |
|---|---|---|
| 550 | 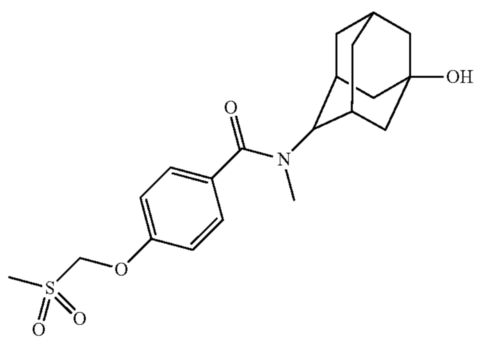 [SMILES: CN(C(=O)c1ccc(OCS(C)(=O)=O)cc1)C1C2CC3CC1CC(O)(C3)C2] | |
| 551 | 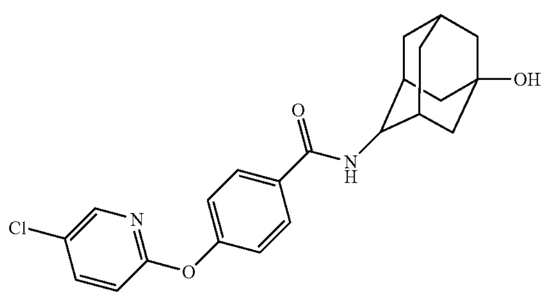 [SMILES: O=C(NC1C2CC3CC1CC(O)(C3)C2)c1ccc(Oc2ccc(Cl)cn2)cc1] | ~70 nM |
| 552 | 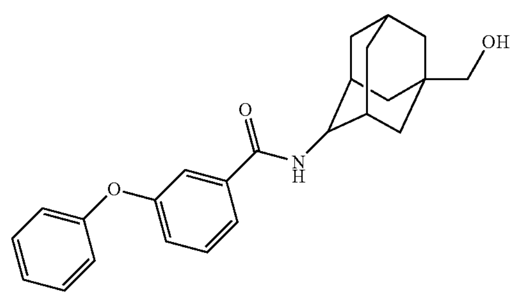 [SMILES: O=C(NC1C2CC3CC1CC(CO)(C3)C2)c1cccc(Oc2ccccc2)c1] | |
| 553 | 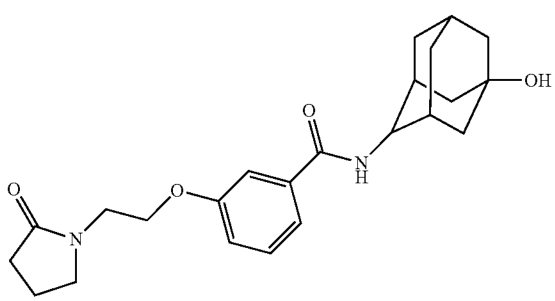 [SMILES: O=C(NC1C2CC3CC1CC(O)(C3)C2)c1cccc(OCCN2CCCC2=O)c1] | |
| 554 | 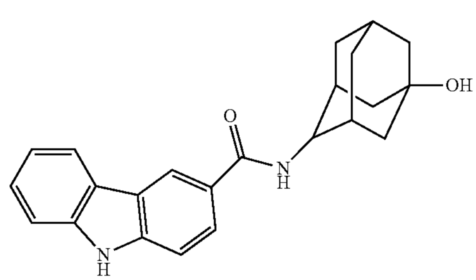 [SMILES: O=C(NC1C2CC3CC1CC(O)(C3)C2)c1ccc2[nH]c3ccccc3c2c1] | 29 nM |

TABLE 3-continued

11βHSD-1 Inhibitors (Boyle, C. D. et al., *Expert Opin. Ther. Patents*, 19(6), 801-825 (2009))

| Example | Structure | IC$_{50}$ |
|---|---|---|
| 555 | 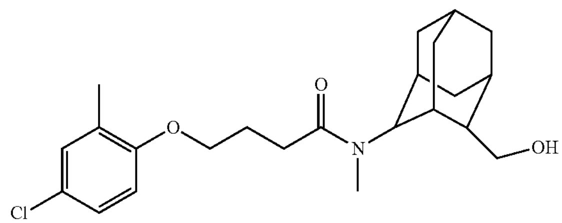 [SMILES: Cc1cc(Cl)ccc1OCCCC(=O)N(C)C1C2CC3CC(C2)C(CO)C1C3] | 1 nM |
| 556 | 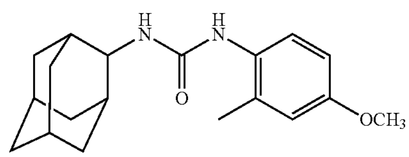 [SMILES: COc1ccc(NC(=O)NC2C3CC4CC(C3)CC2C4)c(C)c1] | 12 nM |
| 557 | 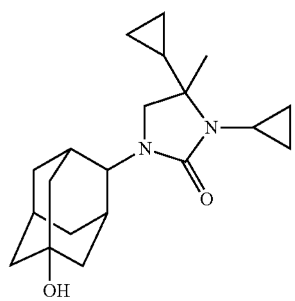 [SMILES: CC1(C2CC2)CN(C2C3CC4CC2CC(O)(C4)C3)C(=O)N1C1CC1] | 3 nM |
| 558 | 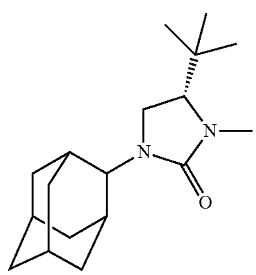 [SMILES: CN1C(=O)N(C2C3CC4CC(C3)CC2C4)C[C@@H]1C(C)(C)C] | <50 nM |
| 559 | 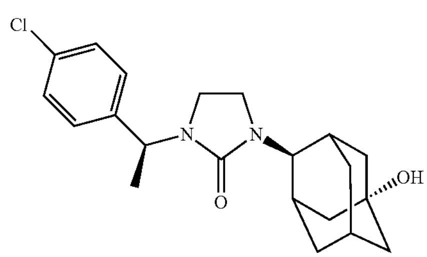 [SMILES: C[C@@H](c1ccc(Cl)cc1)N1CCN([C@H]2C3CC4CC2C[C@](O)(C4)C3)C1=O] | 12 nM |
| 560 | 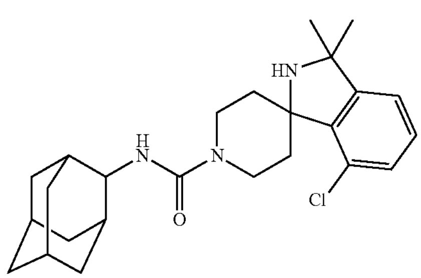 [SMILES: CC1(C)NC2(CCN(C(=O)NC3C4CC5CC(C4)CC3C5)CC2)c2c(Cl)cccc21] | <50 nM |

TABLE 3-continued

11βHSD-1 Inhibitors (Boyle, C. D. et al., *Expert Opin. Ther. Patents*, 19(6), 801-825 (2009))

| Example | Structure | IC$_{50}$ |
| --- | --- | --- |
| 561 | 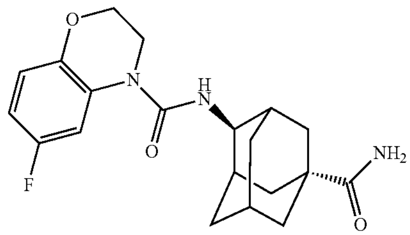 [SMILES: NC(=O)[C@]12CC3CC(C1)[C@@H](NC(=O)N1CCOc4ccc(F)cc41)C(C3)C2] | 0.6 nM |
| 562 | 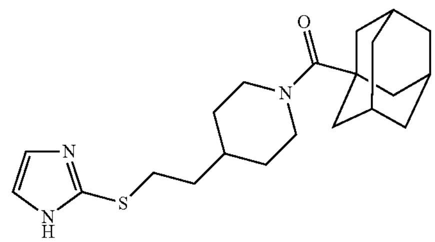 [SMILES: O=C(N1CCC(CCSc2ncc[nH]2)CC1)C12CC3CC(CC(C3)C1)C2] | 120 nM |
| 563 | 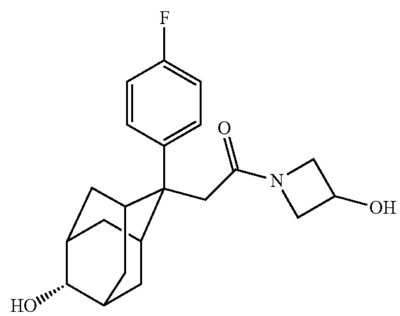 | 8.5 nM |
| 564 | 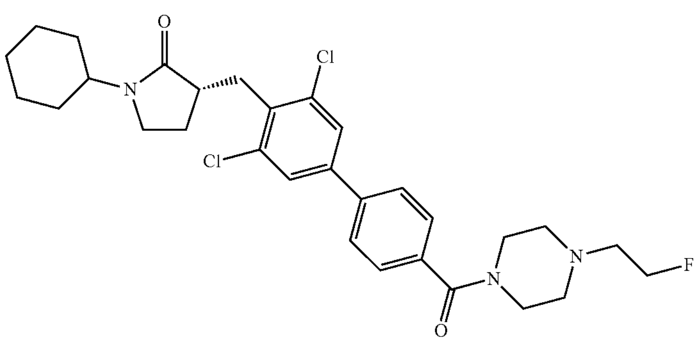 [SMILES: O=C(c1ccc(-c2cc(Cl)c(C[C@@H]3CCN(C4CCCCC4)C3=O)c(Cl)c2)cc1)N1CCN(CCF)CC1] | 115 nM |
| 565 | 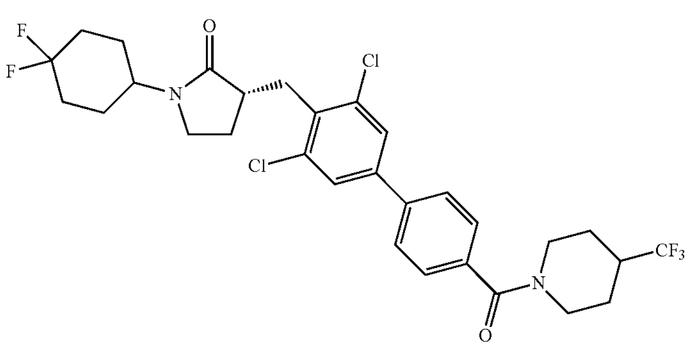 [SMILES: O=C(c1ccc(-c2cc(Cl)c(C[C@@H]3CCN(C4CCC(F)(F)CC4)C3=O)c(Cl)c2)cc1)N1CCC(C(F)(F)F)CC1] | 686.5 nM |

TABLE 3-continued

11βHSD-1 Inhibitors (Boyle, C. D. et al., *Expert Opin. Ther. Patents*, 19(6), 801-825 (2009))

| Example | Structure | IC$_{50}$ |
|---------|-----------|-----------|
| 566 | 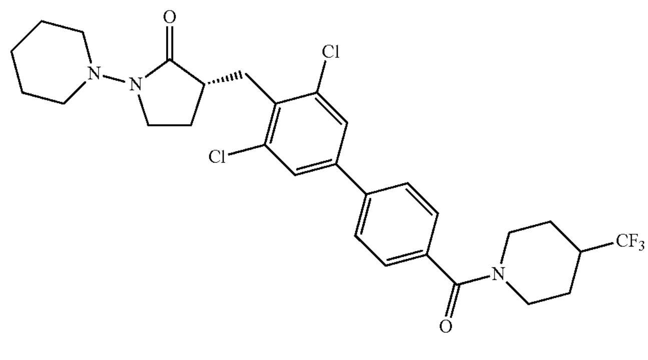 [SMILES: O=C(c1ccc(-c2cc(Cl)c(C[C@@H]3CCN(N4CCCCC4)C3=O)c(Cl)c2)cc1)N1CCC(C(F)(F)F)CC1] | 16.8 nM |
| 567 | 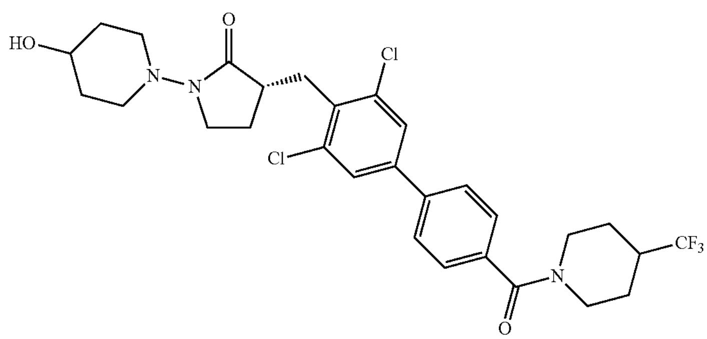 [SMILES: O=C(c1ccc(-c2cc(Cl)c(C[C@@H]3CCN(N4CCC(O)CC4)C3=O)c(Cl)c2)cc1)N1CCC(C(F)(F)F)CC1] | 14.3 nM |
| 568 | 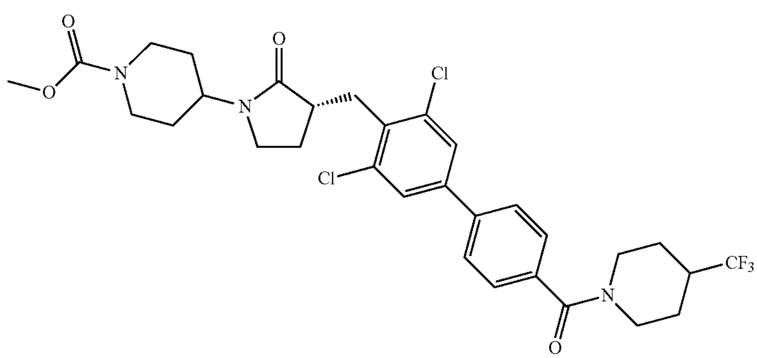 [SMILES: COC(=O)N1CCC(N2CC[C@@H](Cc3c(Cl)cc(-c4ccc(C(=O)N5CCC(C(F)(F)F)CC5)cc4)cc3Cl)C2=O)CC1] | 231 nM |
| 569 | 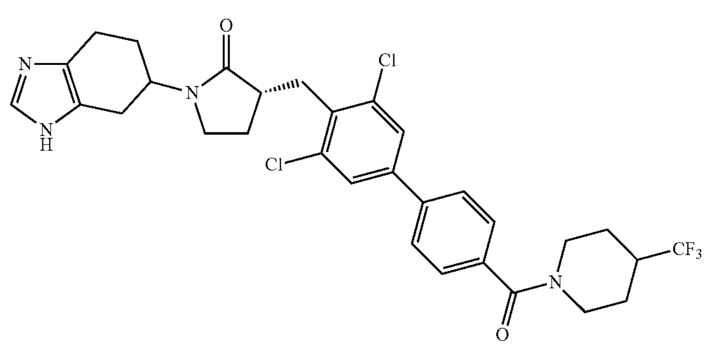 [SMILES: O=C(c1ccc(-c2cc(Cl)c(C[C@@H]3CCN(C4CCc5nc[nH]c5C4)C3=O)c(Cl)c2)cc1)N1CCC(C(F)(F)F)CC1] | 143 nM |

TABLE 3-continued
11βHSD-1 Inhibitors (Boyle, C. D. et al., *Expert Opin. Ther. Patents*, 19(6), 801-825 (2009))
| Example | Structure | IC$_{50}$ |
|---|---|---|
| 570 | 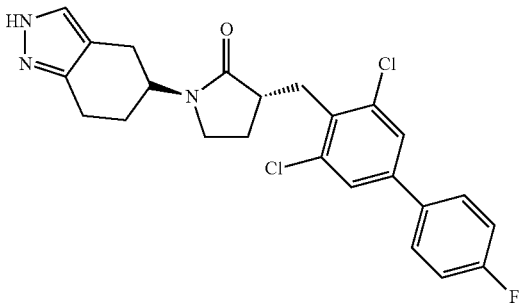 | 276 nM |
| 571 | 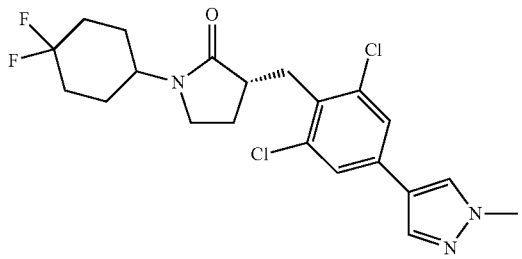 [SMILES: Cn1cc(-c2cc(Cl)c(C[C@@H]3CCN(C4CCC(F)(F)CC4)C3=O)c(Cl)c2)cn1] | 302 nM |
| 572 | 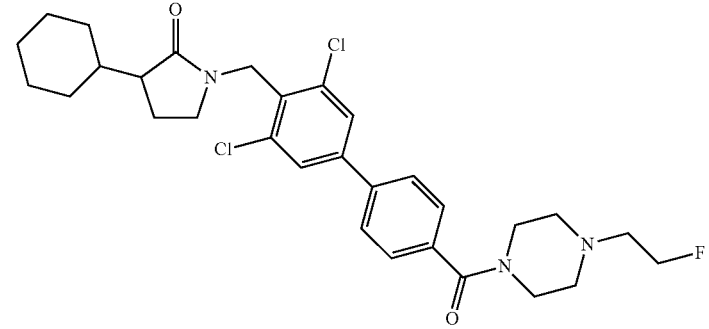 [SMILES: O=C(c1ccc(-c2cc(Cl)c(CN3CCC(C4CCCCC4)C3=O)c(Cl)c2)cc1)N1CCN(CCF)CC1] | 15.4 nM |
| 573 | 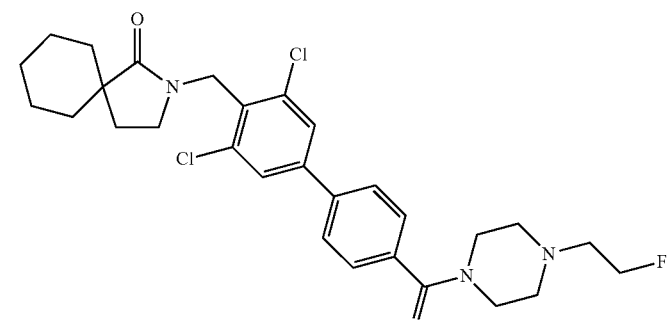 | 888 nM |
| 574 | 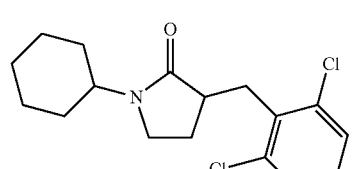 | 7.9 nM |

TABLE 3-continued

11βHSD-1 Inhibitors (Boyle, C. D. et al., *Expert Opin. Ther. Patents*, 19(6), 801-825 (2009))

| Example | Structure | $IC_{50}$ |
|---------|-----------|-----------|
| 575 | 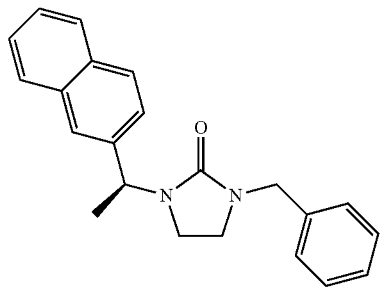 [SMILES: C[C@@H](c1ccc2ccccc2c1)N1CCN(Cc2ccccc2)C1=O] | 2.9 nM |
| 576 | 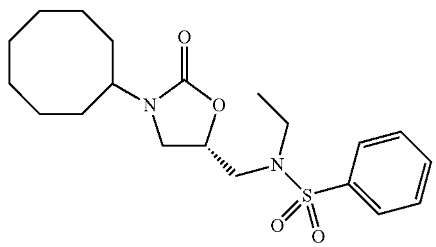 [SMILES: CCN(C[C@@H]1CN(C2CCCCCCC2)C(=O)O1)S(=O)(=O)c1ccccc1] | 430 nM |
| 577 | 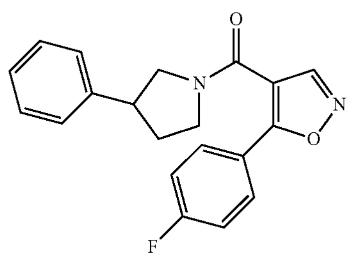 [SMILES: O=C(c1cnoc1-c1ccc(F)cc1)N1CCC(c2ccccc2)C1] | 8 nm - 10 μM |
| 578 | 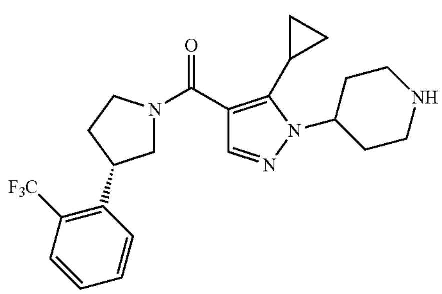 [SMILES: O=C(c1cnn(C2CCNCC2)c1C1CC1)N1CC[C@@H](c2ccccc2C(F)(F)F)C1] | <30 nM |
| 579 | 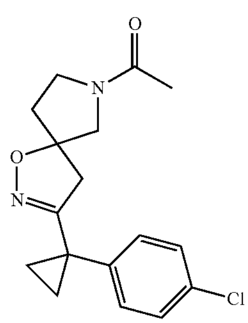 [SMILES: CC(=O)N1CCC2(CC(C3(c4ccc(Cl)cc4)CC3)=NO2)C1] | <5 μM |

TABLE 3-continued

11βHSD-1 Inhibitors (Boyle, C. D. et al., *Expert Opin. Ther. Patents*, 19(6), 801-825 (2009))

| Example | Structure | $IC_{50}$ |
|---|---|---|
| 580 | 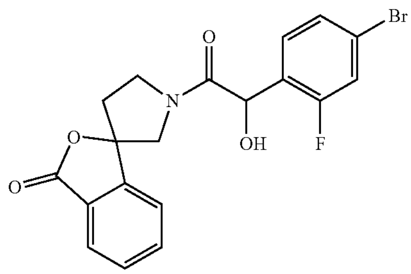 [SMILES: O=C1OC2(CCN(C(=O)C(O)c3ccc(Br)cc3F)C2)c2ccccc21] | <1 μM |
| 581 | 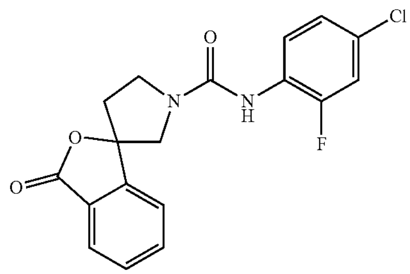 [SMILES: O=C1OC2(CCN(C(=O)Nc3ccc(Cl)cc3F)C2)c2ccccc21] | <20 μM |
| 582 | 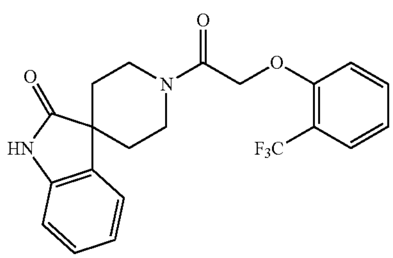 [SMILES: O=C(COc1ccccc1C(F)(F)F)N1CCC2(CC1)C(=O)Nc1ccccc12] | 33 nM |
| 583 | 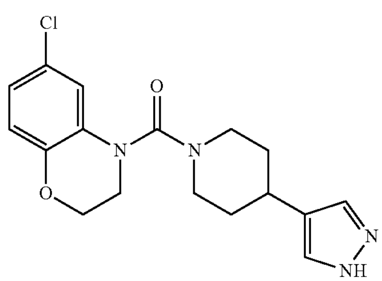 [SMILES: O=C(N1CCC(c2cn[nH]c2)CC1)N1CCOc2ccc(Cl)cc21] | 39 nM |
| 584 | 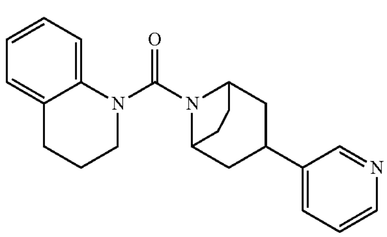 [SMILES: O=C(N1CCCc2ccccc21)N1C2CCC1CC(c1cccnc1)C2] | 19 nM |
| 585 | 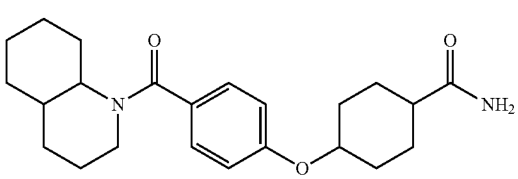 [SMILES: NC(=O)C1CCC(Oc2ccc(C(=O)N3CCCC4CCCCC43)cc2)CC1] | 73 nM |

TABLE 3-continued

11βHSD-1 Inhibitors (Boyle, C. D. et al., *Expert Opin. Ther. Patents*, 19(6), 801-825 (2009))

| Example | Structure | IC$_{50}$ |
|---------|-----------|-----------|
| 586 | 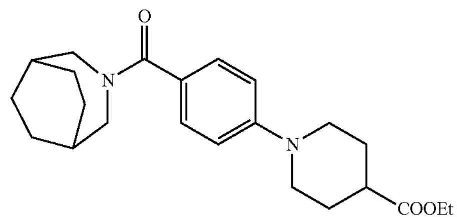 [SMILES: CCOC(=O)C1CCN(c2ccc(C(=O)N3CC4CCC(CC4)C3)cc2)CC1] | |
| 587 | 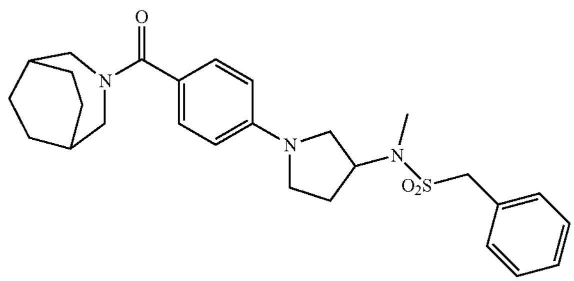 [SMILES: CN(C1CCN(c2ccc(C(=O)N3CC4CCC(CC4)C3)cc2)C1)S(=O)(=O)Cc1ccccc1] | 43 nM |
| 588 | 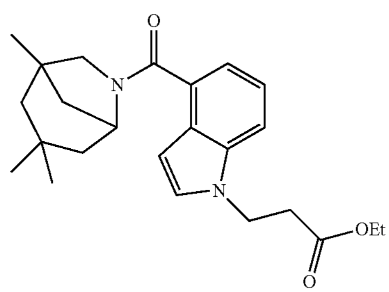 [SMILES: CCOC(=O)CCn1ccc2c(C(=O)N3CC4(C)CC3CC(C)(C)C4)cccc21] | |
| 589 | 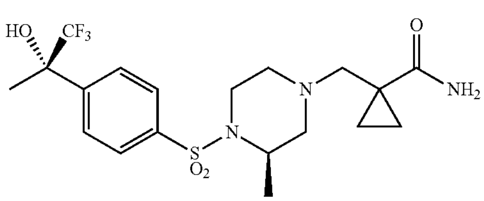 [SMILES: C[C@@H]1CN(CC2(C(N)=O)CC2)CCN1S(=O)(=O)c1ccc([C@](C)(O)C(F)(F)F)cc1] | 0.83 nM |
| 590 | 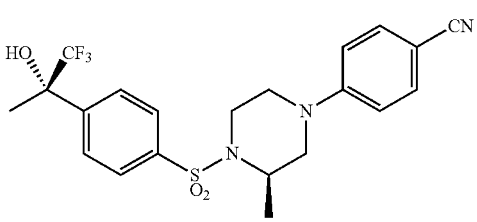 [SMILES: C[C@@H]1CN(c2ccc(C#N)cc2)CCN1S(=O)(=O)c1ccc([C@](C)(O)C(F)(F)F)cc1] | |
| 591 | 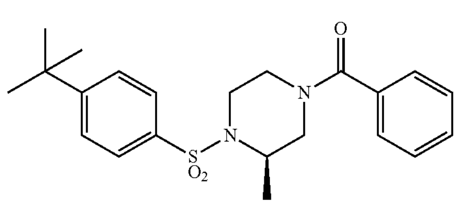 [SMILES: C[C@@H]1CN(C(=O)c2ccccc2)CCN1S(=O)(=O)c1ccc(C(C)(C)C)cc1] | |

TABLE 3-continued
11βHSD-1 Inhibitors (Boyle, C. D. et al., *Expert Opin. Ther. Patents*, 19(6), 801-825 (2009))
| Example | Structure | IC$_{50}$ |
|---|---|---|
| 592 | 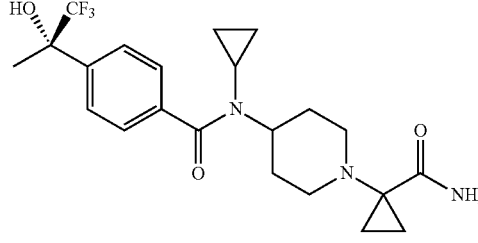 | |
| 593 | 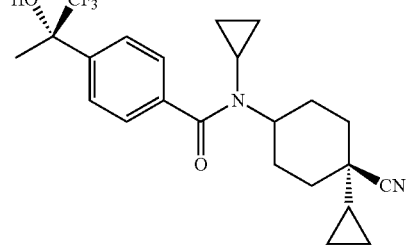 | 1.4 nM |
| 594 | 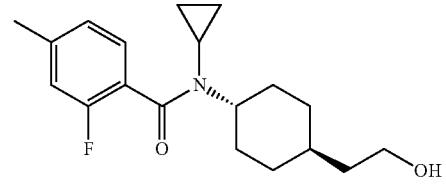 [SMILES: Cc1ccc(C(=O)N(C2CC2)[C@H]2CC[C@H](CCO)CC2)c(F)c1] | 2 nM |
| 595 | 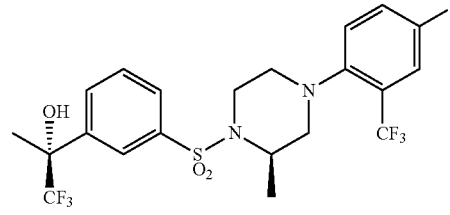 | |
| 596 | 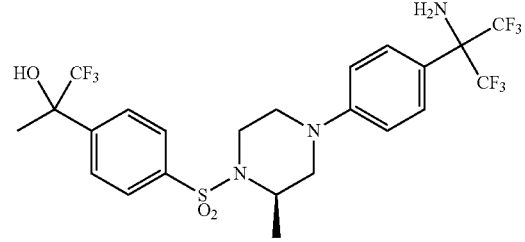 [SMILES: C[C@@H]1CN(c2ccc(C(N)(C(F)(F)F)C(F)(F)F)cc2)CCN1S(=O)(=O)c1ccc(C(C)(O)C(F)(F)F)cc1] | <10 nM |
| 597 | 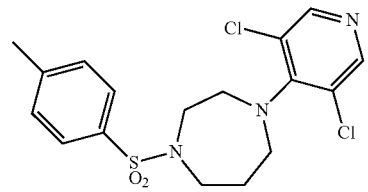 [SMILES: Cc1ccc(S(=O)(=O)N2CCCN(c3c(Cl)cncc3Cl)CC2)cc1] | 910 nM |

TABLE 3-continued

11βHSD-1 Inhibitors (Boyle, C. D. et al., *Expert Opin. Ther. Patents*, 19(6), 801-825 (2009))

| Example | Structure | IC$_{50}$ |
|---|---|---|
| 598 | 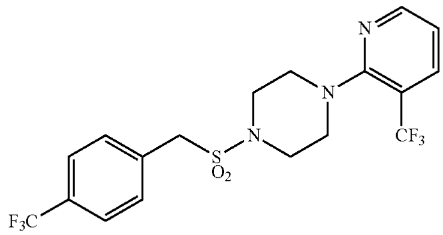 [SMILES: O=S(=O)(Cc1ccc(C(F)(F)F)cc1)N1CCN(c2ncccc2C(F)(F)F)CC1] | 430 nM |
| 599 | 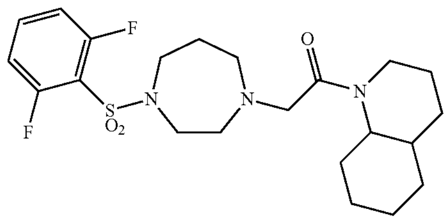 [SMILES: O=C(CN1CCCN(S(=O)(=O)c2c(F)cccc2F)CC1)N1CCCC2CCCCC21] | 17 nM |
| 600 | 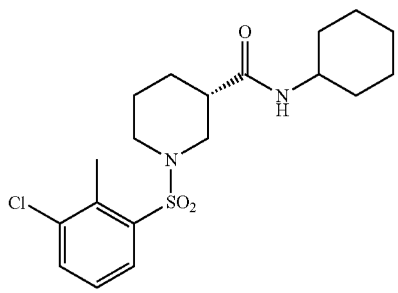 [SMILES: Cc1c(Cl)cccc1S(=O)(=O)N1CCC[C@H](C(=O)NC2CCCCC2)C1] | 3 nM |
| 601 | 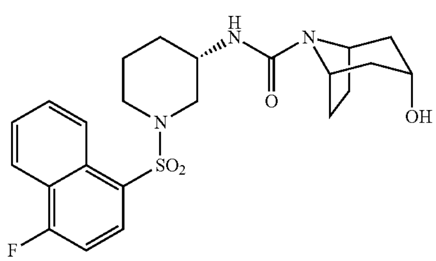 [SMILES: O=C(N[C@H]1CCCN(S(=O)(=O)c2ccc(F)c3ccccc23)C1)N1C2CCC1CC(O)C2] | 3 nM |
| 602 | 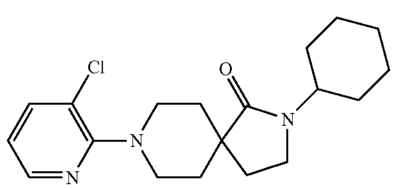 [SMILES: O=C1N(C2CCCCC2)CCC12CCN(c1ncccc1Cl)CC2] | |
| 603 | 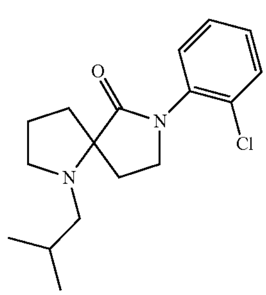 [SMILES: CC(C)CN1CCCC12CCN(c1ccccc1Cl)C2=O] | |

TABLE 3-continued

11βHSD-1 Inhibitors (Boyle, C. D. et al., *Expert Opin. Ther. Patents*, 19(6), 801-825 (2009))

| Example | Structure | IC$_{50}$ |
|---|---|---|
| 604 | 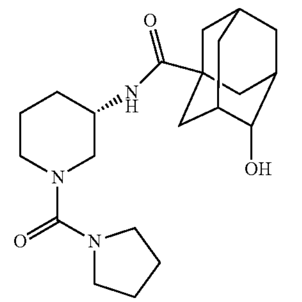 [SMILES: O=C(N1CCCC1)N1CCC[C@H](NC(=O)C23CC4CC(C2)C(O)C(C4)C3)C1] | |
| 605 | 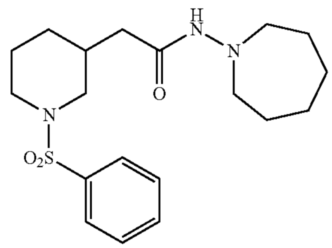 [SMILES: O=C(CC1CCCN(S(=O)(=O)c2ccccc2)C1)NN1CCCCCC1] | |
| 606 | 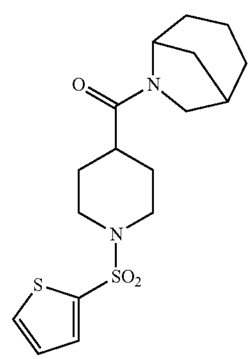 [SMILES: O=C(C1CCN(S(=O)(=O)c2cccs2)CC1)N1CC2CCCC1C2] | |
| 607 | 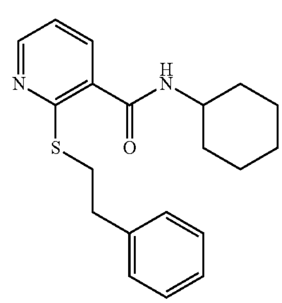 [SMILES: O=C(NC1CCCCC1)c1cccnc1SCCc1ccccc1] | 27 nM |
| 608 | 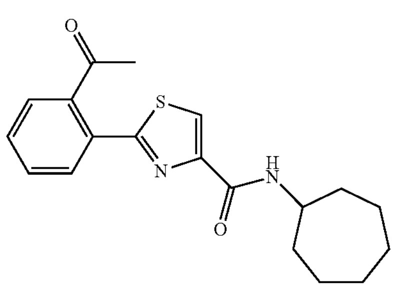 [SMILES: CC(=O)c1ccccc1-c1nc(C(=O)NC2CCCCCC2)cs1] | 32 nM |

TABLE 3-continued

11βHSD-1 Inhibitors (Boyle, C. D. et al., *Expert Opin. Ther. Patents*, 19(6), 801-825 (2009))

| Example | Structure | IC$_{50}$ |
|---|---|---|
| 609 | 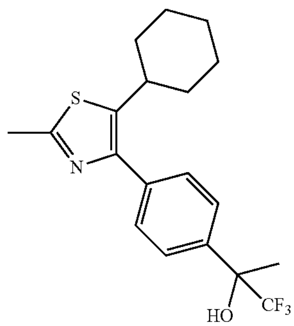 [SMILES: Cc1nc(-c2ccc(C(C)(O)C(F)(F)F)cc2)c(C2CCCCC2)s1] | |
| 610 | 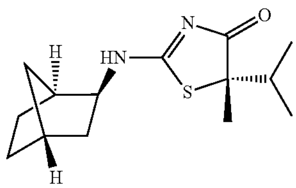 [SMILES: CC(C)[C@]1(C)SC(N[C@H]2C[C@@H]3CC[C@H]2C3)=NC1=O] | |
| 611 | 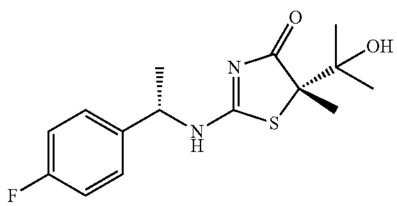 [SMILES: C[C@H](NC1=NC(=O)[C@](C)(C(C)(C)O)S1)c1ccc(F)cc1] | 34 nM |

TABLE 4

11βHSD-1 Inhibitors (Webster, S. P. et al., *Expert Opin. Ther. Patents*, 17(12), 1407-1422 (2007))

| Example | Structure | IC$_{50}$ |
|---|---|---|
| 612 | 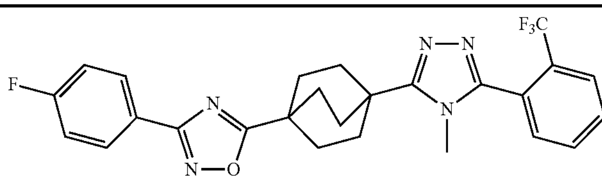 | |
| 613 | 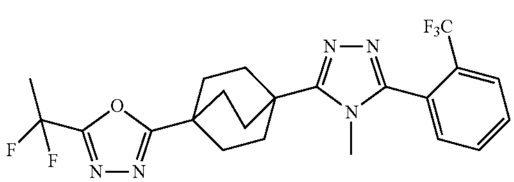 [SMILES: Cn1c(-c2ccccc2C(F)(F)F)nnc1C12CCC(c3nnc(C(C)(F)F)o3)(CC1)CC2] | |
| 614 | 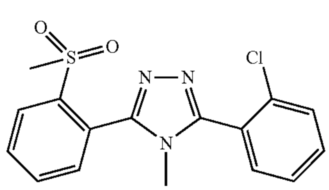 [SMILES: Cn1c(-c2ccccc2Cl)nnc1-c1ccccc1S(C)(=O)=O] | |

TABLE 4-continued

11βHSD-1 Inhibitors (Webster, S. P. et al., *Expert Opin. Ther. Patents*, 17(12), 1407-1422 (2007))

| Example | Structure | IC$_{50}$ |
|---|---|---|
| 615 | 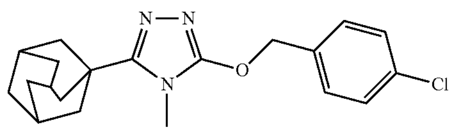 [SMILES: Cn1c(OCc2ccc(Cl)cc2)nnc1C12CC3CC(CC(C3)C1)C2] | |
| 616 | 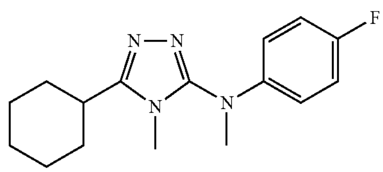 [SMILES: CN(c1ccc(F)cc1)c1nnc(C2CCCCC2)n1C] | |
| 617 | 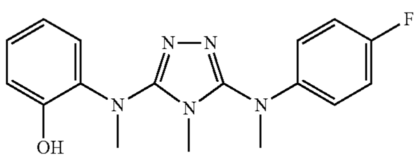 [SMILES: CN(c1ccc(F)cc1)c1nnc(N(C)c2ccccc2O)n1C] | |
| 618 | 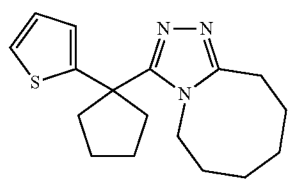 [SMILES: c1csc(C2(c3nnc4n3CCCCCC4)CCCC2)c1] | |
| 619 | 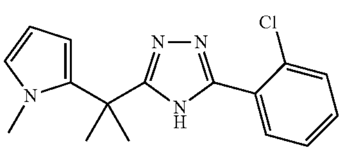 [SMILES: Cn1cccc1C(C)(C)c1nnc(-c2ccccc2Cl)[nH]1] | |
| 620 | 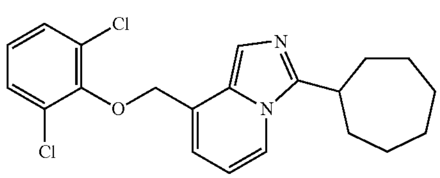 [SMILES: Clc1cccc(Cl)c1OCc1cccn2c(C3CCCCCC3)ncc12] | |
| 621 | 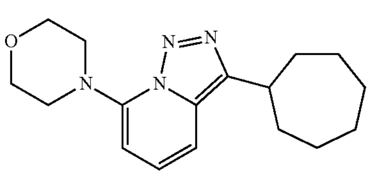 [SMILES: c1cc(N2CCOCC2)n2nnc(C3CCCCCC3)c2c1] | |
| 622 | 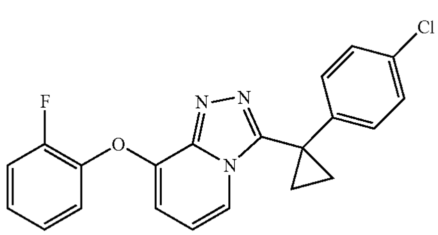 [SMILES: Fc1ccccc1Oc1cccn2c(C3(c4ccc(Cl)cc4)CC3)nnc12] | |

TABLE 4-continued

11βHSD-1 Inhibitors (Webster, S. P. et al., *Expert Opin. Ther. Patents*, 17(12), 1407-1422 (2007))

| Example | Structure | IC$_{50}$ |
|---|---|---|
| 623 | 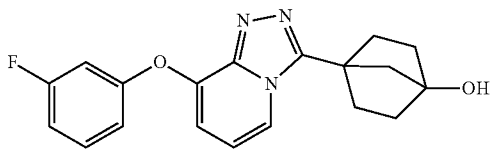 [SMILES: OC12CCC(c3nnc4c(Oc5cccc(F)c5)cccn34)(CC1)C2] | |
| 624 | 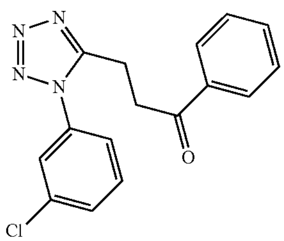 [SMILES: O=C(CCc1nnnn1-c1cccc(Cl)c1)c1ccccc1] | |
| 625 | 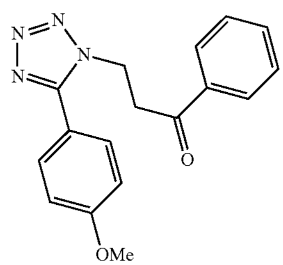 [SMILES: COc1ccc(-c2nnnn2CCC(=O)c2ccccc2)cc1] | |
| 626 | 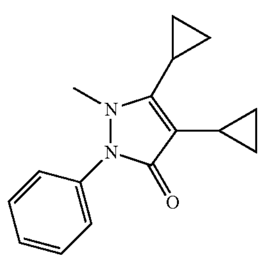 [SMILES: Cn1c(C2CC2)c(C2CC2)c(=O)n1-c1ccccc1] | |
| 627 | 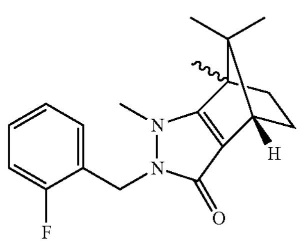 [SMILES: Cn1c2c(c(=O)n1Cc1ccccc1F)[C@H]1CCC2(C)C1(C)C] | |
| 628 | 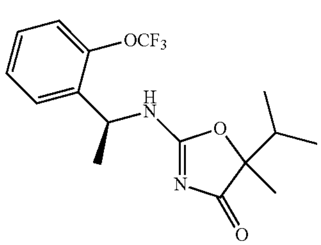 [SMILES: CC(C)C1(C)OC(N[C@@H](C)c2ccccc2OC(F)(F)F)=NC1=O] | |

TABLE 4-continued

11βHSD-1 Inhibitors (Webster, S. P. et al., *Expert Opin. Ther. Patents*, 17(12), 1407-1422 (2007))

| Example | Structure | IC$_{50}$ |
|---------|-----------|-----------|
| 629 | 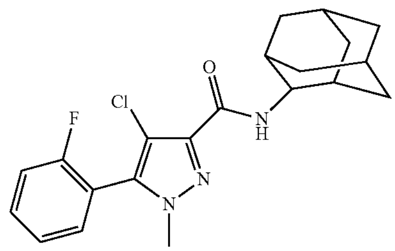 [SMILES: Cn1nc(C(=O)NC2C3CC4CC(C3)CC2C4)c(Cl)c1-c1ccccc1F] | |
| 630 | 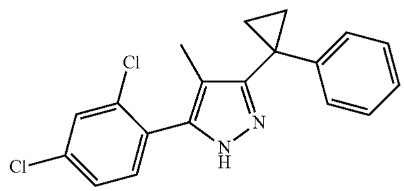 [SMILES: Cc1c(C2(c3ccccc3)CC2)n[nH]c1-c1ccc(Cl)cc1Cl] | |
| 631 | 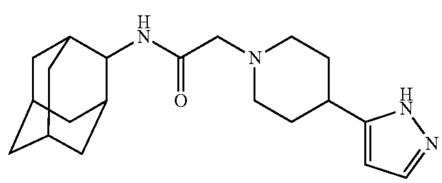 [SMILES: O=C(CN1CCC(c2ccn[nH]2)CC1)NC1C2CC3CC(C2)CC1C3] | |
| 632 | 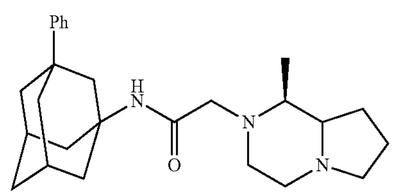 [SMILES: C[C@H]1C2CCCN2CCN1CC(=O)NC12CC3CC(C1)CC(c1ccccc1)(C3)C2] | |
| 633 | 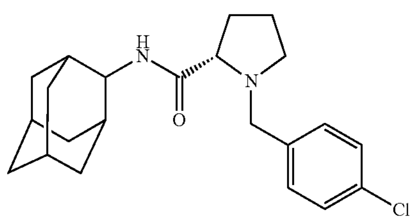 [SMILES: O=C(NC1C2CC3CC(C2)CC1C3)[C@@H]1CCCN1Cc1ccc(Cl)cc1] | |
| 634 | 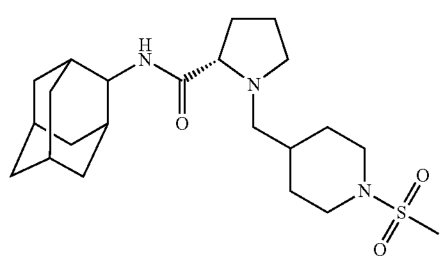 [SMILES: CS(=O)(=O)N1CCC(CN2CCC[C@H]2C(=O)NC2C3CC4CC(C3)CC2C4)CC1] | |
| 635 | 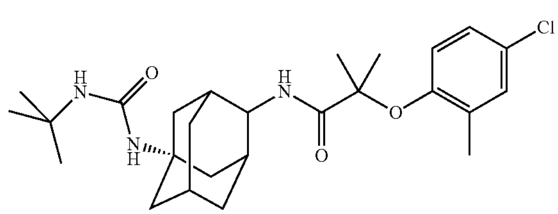 | |

TABLE 4-continued
11βHSD-1 Inhibitors (Webster, S. P. et al., *Expert Opin. Ther. Patents*, 17(12), 1407-1422 (2007))
| Example | Structure | IC$_{50}$ |
|---|---|---|
| 636 | 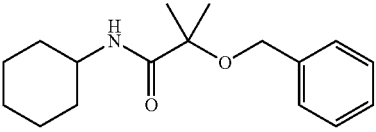 [SMILES: CC(C)(OCc1ccccc1)C(=O)NC1CCCCC1] | |
| 637 | 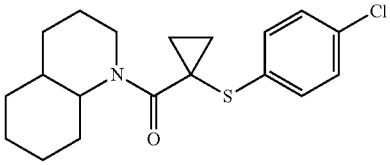 [SMILES: O=C(N1CCCC2CCCCC21)C1(Sc2ccc(Cl)cc2)CC1] | |
| 638 | 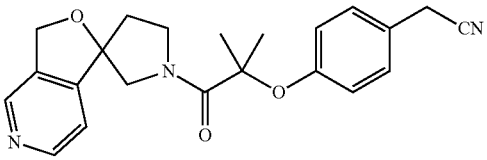 [SMILES: CC(C)(Oc1ccc(CC#N)cc1)C(=O)N1CCC2(C1)OCc1cnccc12] | |
| 639 | 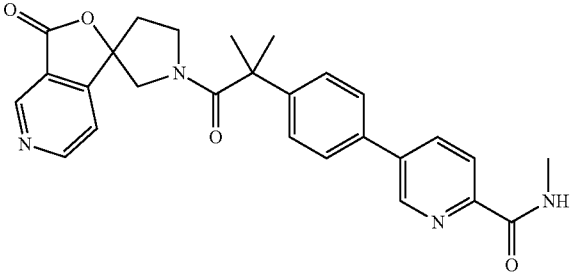 [SMILES: CNC(=O)c1ccc(-c2ccc(C(C)(C)C(=O)N3CCC4(C3)OC(=O)c3cnccc34)cc2)cn1] | |
| 640 | 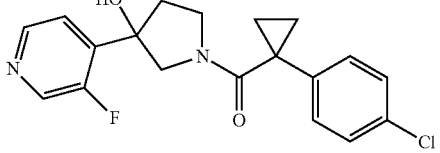 | |
| 641 | 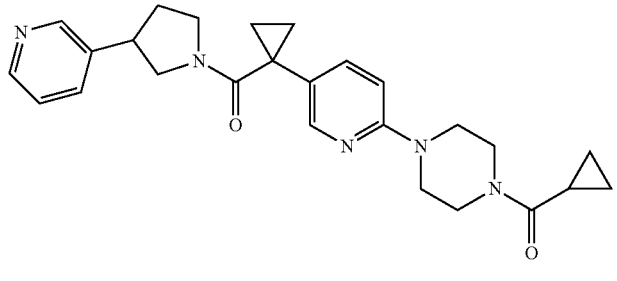 [SMILES: O=C(C1CC1)N1CCN(c2ccc(C3(C(=O)N4CCC(c5cccnc5)C4)CC3)cn2)CC1] | |
| 642 | 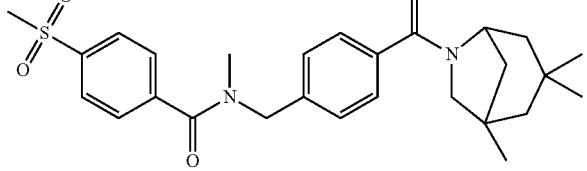 | |

TABLE 4-continued

11βHSD-1 Inhibitors (Webster, S. P. et al., *Expert Opin. Ther. Patents*, 17(12), 1407-1422 (2007))

| Example | Structure | IC$_{50}$ |
|---------|-----------|-----------|
| 643 | 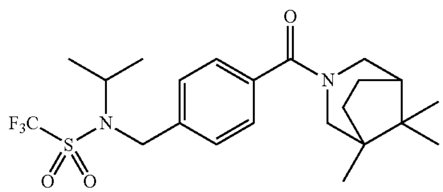 [SMILES: CC(C)N(Cc1ccc(C(=O)N2CC3CCC(C)(C2)C3(C)C)cc1)S(=O)(=O)C(F)(F)F] | |
| 644 | 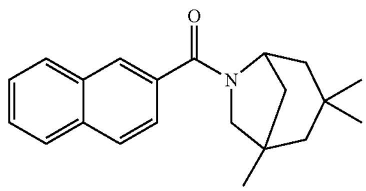 [SMILES: CC1(C)CC2CC(C)(CN2C(=O)c2ccc3ccccc3c2)C1] | |
| 645 | 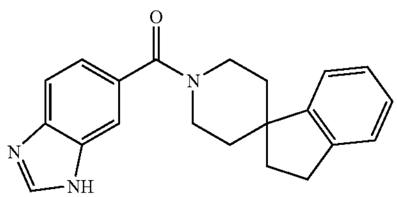 [SMILES: O=C(c1ccc2nc[nH]c2c1)N1CCC2(CCc3ccccc32)CC1] | |
| 646 | 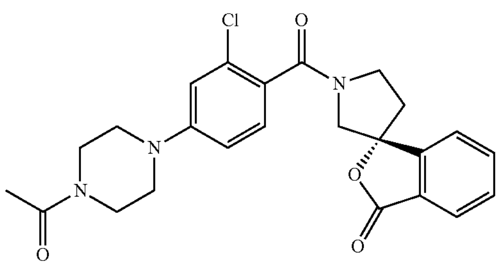 [SMILES: CC(=O)N1CCN(c2ccc(C(=O)N3CC[C@@]4(C3)OC(=O)c3ccccc34)c(Cl)c2)CC1] | |
| 647 | 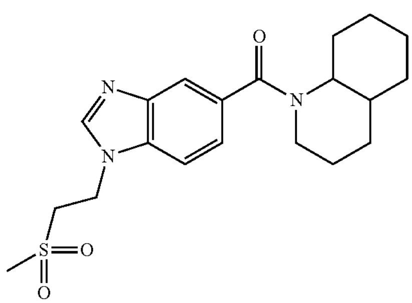 [SMILES: CS(=O)(=O)CCn1cnc2cc(C(=O)N3CCCC4CCCCC43)ccc21] | |
| 648 | 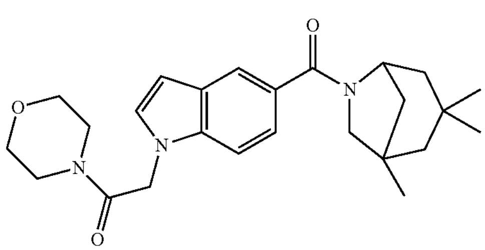 [SMILES: CC1(C)CC2CC(C)(CN2C(=O)c2ccc3c(ccn3CC(=O)N3CCOCC3)c2)C1] | |

TABLE 4-continued

11βHSD-1 Inhibitors (Webster, S. P. et al., *Expert Opin. Ther. Patents*, 17(12), 1407-1422 (2007))

| Example | Structure | $IC_{50}$ |
|---------|-----------|-----------|
| 649 | 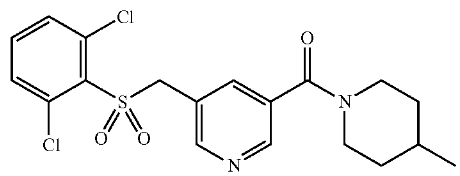 [SMILES: CC1CCN(C(=O)c2cncc(CS(=O)(=O)c3c(Cl)cccc3Cl)c2)CC1] | |
| 650 | 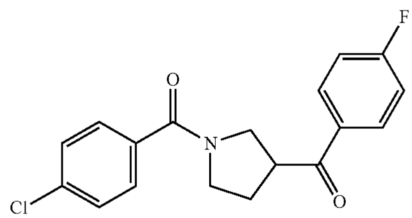 [SMILES: O=C(c1ccc(F)cc1)C1CCN(C(=O)c2ccc(Cl)cc2)C1] | |
| 651 | 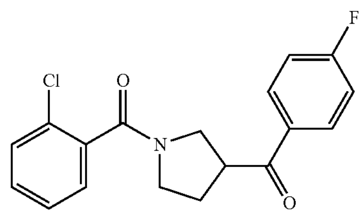 [SMILES: O=C(c1ccc(F)cc1)C1CCN(C(=O)c2ccccc2Cl)C1] | |
| 652 | 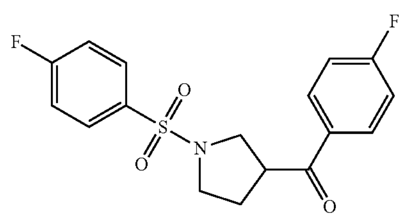 [SMILES: O=C(c1ccc(F)cc1)C1CCN(S(=O)(=O)c2ccc(F)cc2)C1] | |
| 653 | 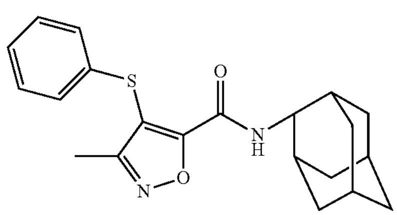 [SMILES: Cc1noc(C(=O)NC2C3CC4CC(C3)CC2C4)c1Sc1ccccc1] | |
| 654 | 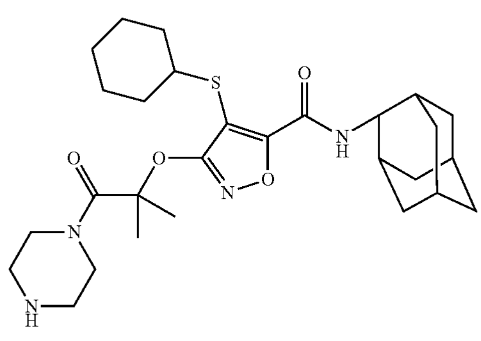 [SMILES: CC(C)(Oc1noc(C(=O)NC2C3CC4CC(C3)CC2C4)c1SC1CCCCC1)C(=O)N1CCNCC1] | |

TABLE 4-continued

11βHSD-1 Inhibitors (Webster, S. P. et al., *Expert Opin. Ther. Patents*, 17(12), 1407-1422 (2007))

| Example | Structure | IC$_{50}$ |
|---|---|---|
| 655 | 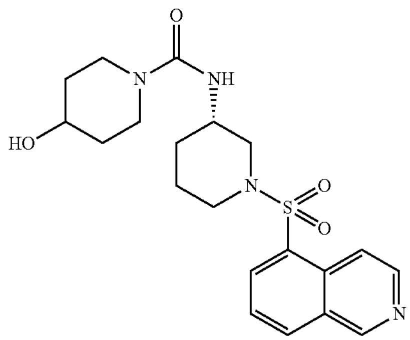 [SMILES: O=C(N[C@H]1CCCN(S(=O)(=O)c2cccc3cnccc23)C1)N1CCC(O)CC1] | |
| 656 | 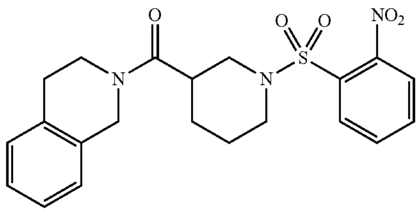 [SMILES: O=C(C1CCCN(S(=O)(=O)c2ccccc2[N+](=O)[O-])C1)N1CCc2ccccc2C1] | |
| 657 | 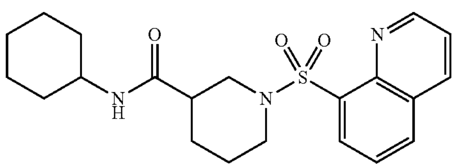 [SMILES: O=C(NC1CCCCC1)C1CCCN(S(=O)(=O)c2cccc3cccnc23)C1] | |
| 658 | 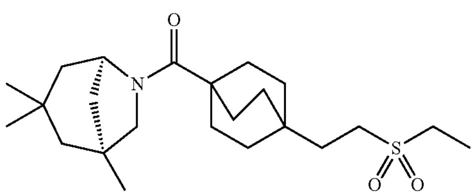 [SMILES: CCS(=O)(=O)CCC12CCC(C(=O)N3C[C@]4(C)C[C@H]3CC(C)(C)C4)(CC1)CC2] | |
| 659 | 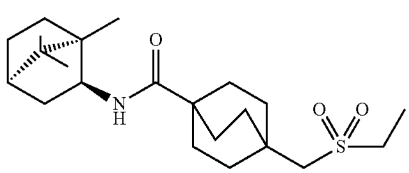 [SMILES: CCS(=O)(=O)CC12CCC(C(=O)N[C@H]3C[C@H]4CC[C@]3(C)C4(C)C)(CC1)CC2] | |
| 660 | 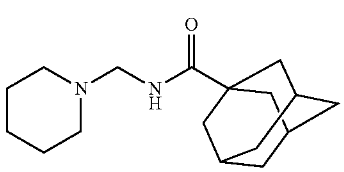 [SMILES: O=C(NCN1CCCCC1)C12CC3CC(CC(C3)C1)C2] | |
| 661 | 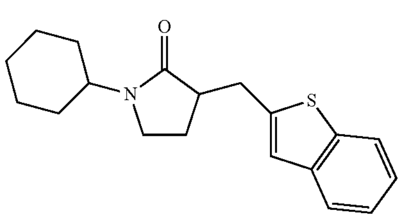 [SMILES: O=C1C(Cc2cc3ccccc3s2)CCN1C1CCCCC1] | |

TABLE 4-continued
11βHSD-1 Inhibitors (Webster, S. P. et al., *Expert Opin. Ther. Patents*, 17(12), 1407-1422 (2007))
| Example | Structure | IC$_{50}$ |
|---|---|---|
| 662 | 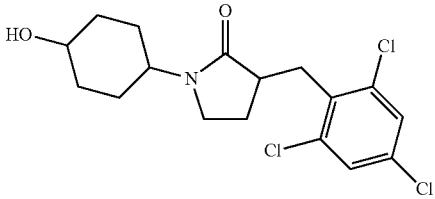 [SMILES: O=C1C(Cc2c(Cl)cc(Cl)cc2Cl)CCN1C1CCC(O)CC1] | |
| 663 | 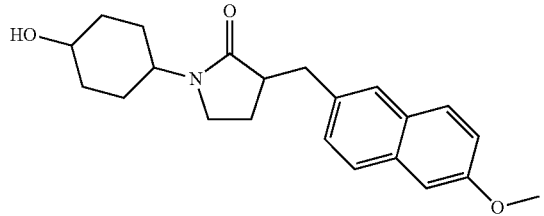 [SMILES: COc1ccc2cc(CC3CCN(C4CCC(O)CC4)C3=O)ccc2c1] | |
| 664 | 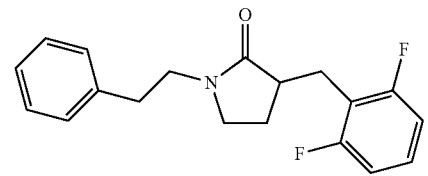 [SMILES: O=C1C(Cc2c(F)cccc2F)CCN1CCc1ccccc1] | |
| 665 | 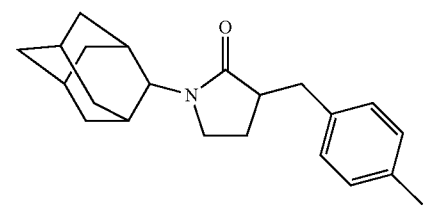 [SMILES: Cc1ccc(CC2CCN(C3C4CC5CC(C4)CC3C5)C2=O)cc1] | |
| 666 | 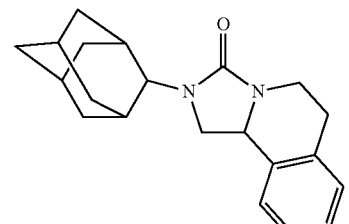 | |
| 667 | 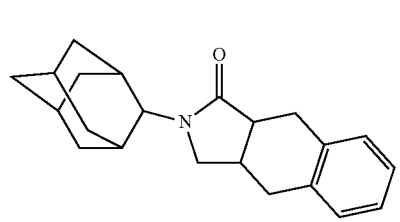 [SMILES: O=C1C2Cc3ccccc3CC2CN1C1C2CC3CC(C2)CC1C3] | |

TABLE 4-continued

11βHSD-1 Inhibitors (Webster, S. P. et al., *Expert Opin. Ther. Patents*, 17(12), 1407-1422 (2007))

| Example | Structure | IC$_{50}$ |
|---|---|---|
| 668 | 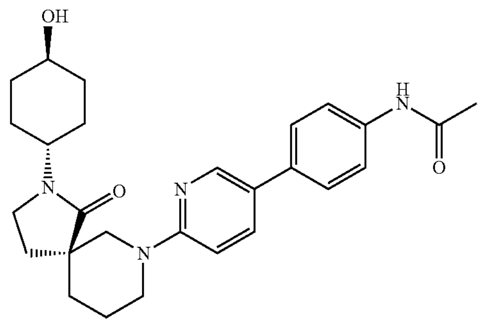 [SMILES: CC(=O)Nc1ccc(-c2ccc(N3CCC[C@]4(CCN([C@H]5CC[C@H](O)CC5)C4=O)C3)nc2)cc1] | |
| 669 | 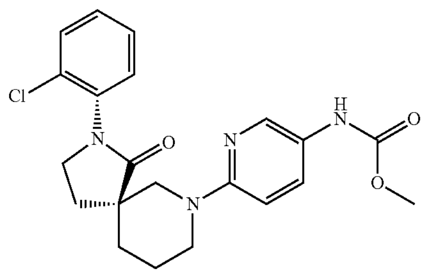 | |
| 670 | 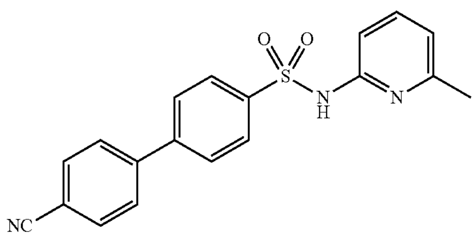 [SMILES: Cc1cccc(NS(=O)(=O)c2ccc(-c3ccc(C#N)cc3)cc2)n1] | Ki = 6.4 nM |
| 671 | 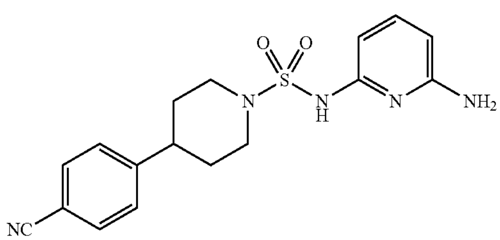 [SMILES: N#Cc1ccc(C2CCN(S(=O)(=O)Nc3cccc(N)n3)CC2)cc1] | Ki = <1 nM |
| 672 | 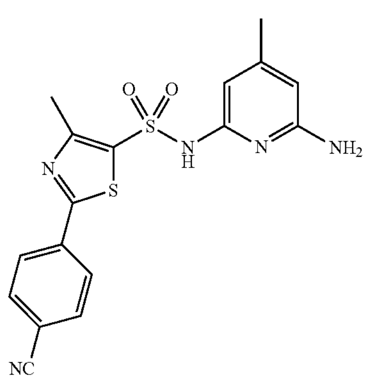 [SMILES: Cc1cc(N)nc(NS(=O)(=O)c2sc(-c3ccc(C#N)cc3)nc2C)c1] | Ki = 2.8 nM |

TABLE 4-continued

11βHSD-1 Inhibitors (Webster, S. P. et al., *Expert Opin. Ther. Patents*, 17(12), 1407-1422 (2007))

| Example | Structure | $IC_{50}$ |
|---------|-----------|-----------|
| 673 | 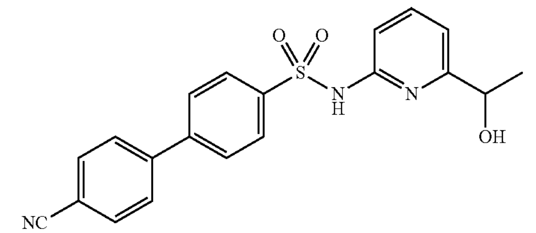 [SMILES: CC(O)c1cccc(NS(=O)(=O)c2ccc(-c3ccc(C#N)cc3)cc2)n1] | Ki = 1.8 nM |
| 674 | 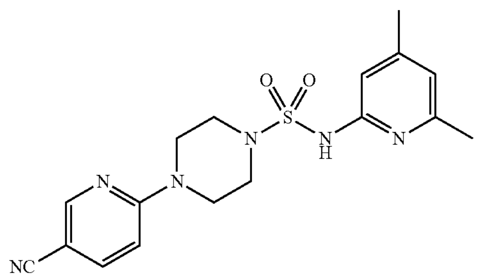 [SMILES: Cc1cc(C)nc(NS(=O)(=O)N2CCN(c3ccc(C#N)cn3)CC2)c1] | Ki = 660 pM |
| 675 | 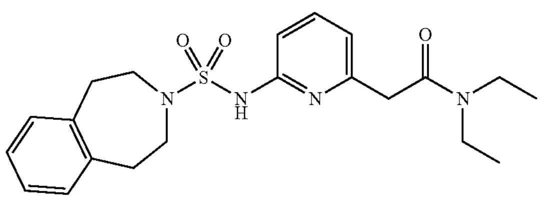 [SMILES: CCN(CC)C(=O)Cc1cccc(NS(=O)(=O)N2CCc3ccccc3CC2)n1] | Ki = 5.7 nM |
| 676 | 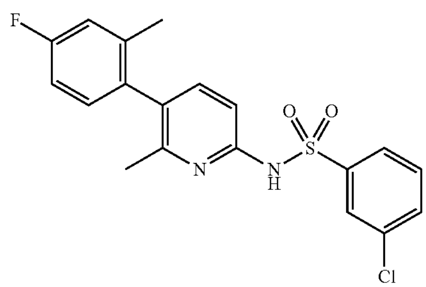 [SMILES: Cc1cc(F)ccc1-c1ccc(NS(=O)(=O)c2cccc(Cl)c2)nc1C] | 12 nM |
| 677 | 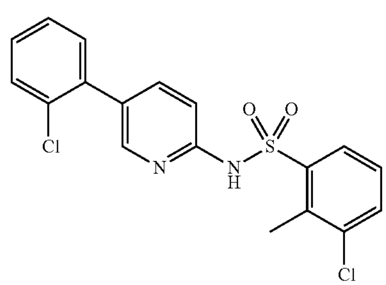 [SMILES: Cc1c(Cl)cccc1S(=O)(=O)Nc1ccc(-c2ccccc2Cl)cn1] | 3 nM |
| 678 | 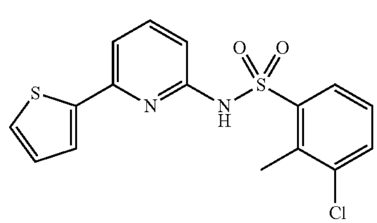 [SMILES: Cc1c(Cl)cccc1S(=O)(=O)Nc1cccc(-c2cccs2)n1] | |

TABLE 4-continued

11βHSD-1 Inhibitors (Webster, S. P. et al., *Expert Opin. Ther. Patents*, 17(12), 1407-1422 (2007))

| Example | Structure | IC$_{50}$ |
|---|---|---|
| 679 | 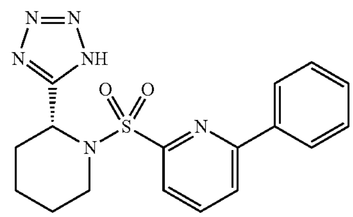 [SMILES: O=S(=O)(c1cccc(-c2ccccc2)n1)N1CCCC[C@@H]1c1nnn[nH]1] | |
| 680 | 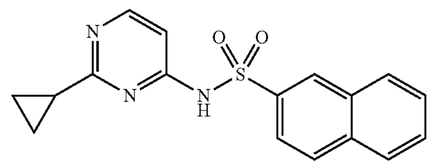 [SMILES: O=S(=O)(Nc1ccnc(C2CC2)n1)c1ccc2ccccc2c1] | 20 nM |
| 681 | 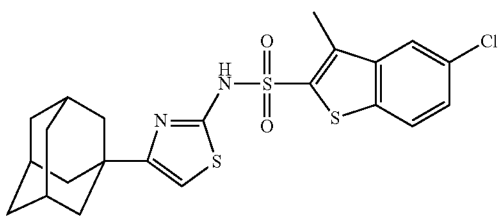 [SMILES: Cc1c(S(=O)(=O)Nc2nc(C34CC5CC(CC(C5)C3)C4)cs2)sc2ccc(Cl)cc12] | 18 nM |
| 682 | 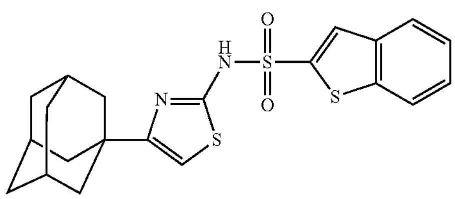 [SMILES: O=S(=O)(Nc1nc(C23CC4CC(CC(C4)C2)C3)cs1)c1cc2ccccc2s1] | 42 nM |
| 683 | 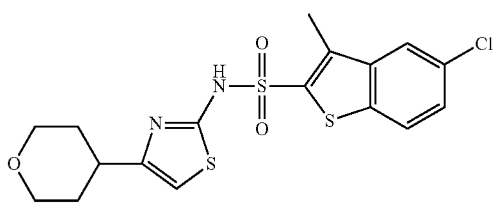 [SMILES: Cc1c(S(=O)(=O)Nc2nc(C3CCOCC3)cs2)sc2ccc(Cl)cc12] | 2 nM |
| 684 | 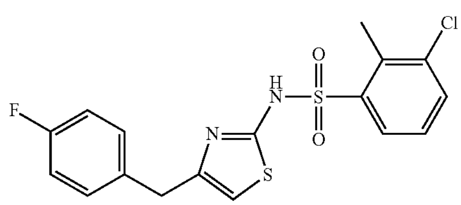 [SMILES: Cc1c(Cl)cccc1S(=O)(=O)Nc1nc(Cc2ccc(F)cc2)cs1] | |
| 685 | 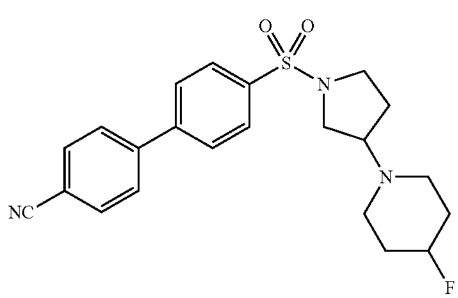 [SMILES: N#Cc1ccc(-c2ccc(S(=O)(=O)N3CCC(N4CCC(F)CC4)C3)cc2)cc1] | Ki = 1.4 pM |

TABLE 4-continued

11βHSD-1 Inhibitors (Webster, S. P. et al., *Expert Opin. Ther. Patents*, 17(12), 1407-1422 (2007))

| Example | Structure | IC$_{50}$ |
|---|---|---|
| 686 | 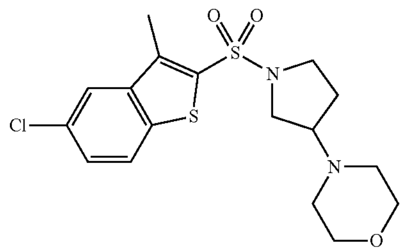 [SMILES: Cc1c(S(=O)(=O)N2CCC(N3CCOCC3)C2)sc2ccc(Cl)cc12] | Ki = 4.4 pM |
| 687 | 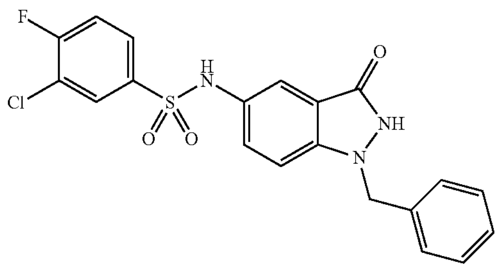 [SMILES: O=c1[nH]n(Cc2ccccc2)c2ccc(NS(=O)(=O)c3ccc(F)c(Cl)c3)cc12] | 7 pM |
| 688 | 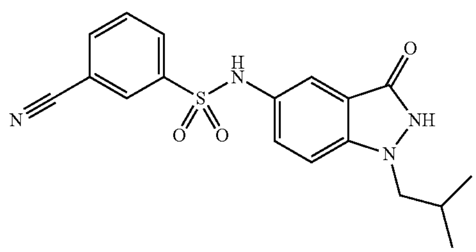 [SMILES: CC(C)Cn1[nH]c(=O)c2cc(NS(=O)(=O)c3cccc(C#N)c3)ccc21] | 101 pM |
| 689 | 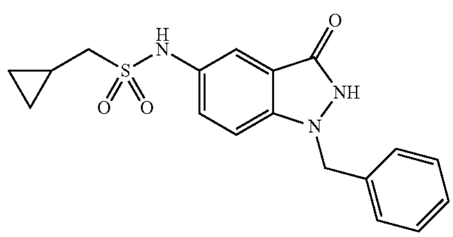 [SMILES: O=c1[nH]n(Cc2ccccc2)c2ccc(NS(=O)(=O)CC3CC3)cc12] | |
| 690 | 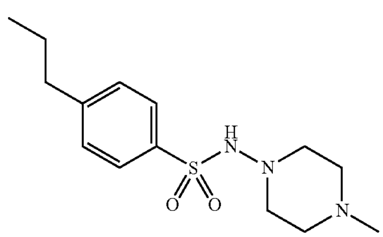 [SMILES: CCCc1ccc(S(=O)(=O)NN2CCN(C)CC2)cc1] | |
| 691 | 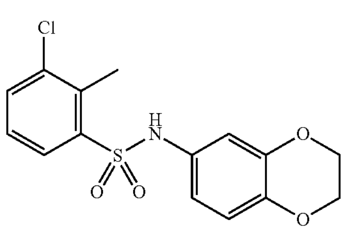 [SMILES: Cc1c(Cl)cccc1S(=O)(=O)Nc1ccc2c(c1)OCCO2] | |

TABLE 4-continued
11βHSD-1 Inhibitors (Webster, S. P. et al., *Expert Opin. Ther. Patents*, 17(12), 1407-1422 (2007))
| Example | Structure | $IC_{50}$ |
|---|---|---|
| 692 | 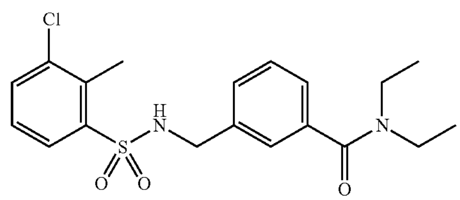 [SMILES: CCN(CC)C(=O)c1cccc(CNS(=O)(=O)c2cccc(Cl)c2C)c1] | |
TABLE 5
11βHSD-1 Inhibitors (Boyle, C. D. *Current Opinion in Drug Discovery & Development* 2008, 11(4), 495-511)
| Example | Structure | $IC_{50}$ |
|---|---|---|
| 683 | 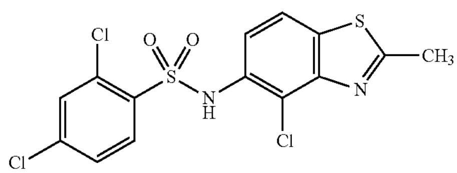 [SMILES: Cc1nc2c(Cl)c(NS(=O)(=O)c3ccc(Cl)cc3Cl)ccc2s1] | 3.2 μM |
| 684 | 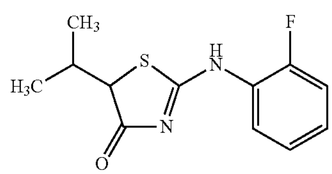 [SMILES: CC(C)C1SC(Nc2ccccc2F)=NC1=O] | 50 nM |
| 685 | 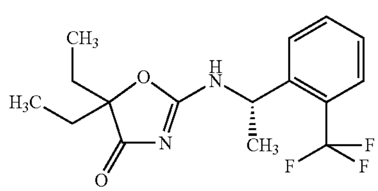 [SMILES: CCC1(CC)OC(N[C@@H](C)c2ccccc2C(F)(F)F)=NC1=O] | 95 nM |
| 686 | 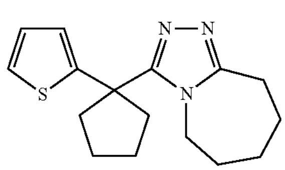 [SMILES: c1csc(C2(c3nnc4n3CCCCC4)CCCC2)c1] | 4.4 nM |
| 687 | 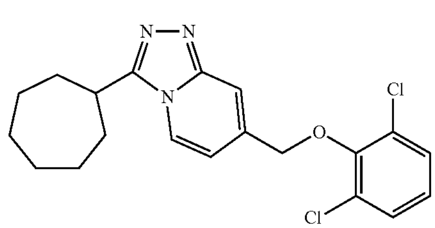 [SMILES: Clc1cccc(Cl)c1OCc1ccn2c(C3CCCCCC3)nnc2c1] | |

TABLE 5-continued

11βHSD-1 Inhibitors (Boyle, C. D. *Current Opinion in Drug Discovery & Development* 2008, 11(4), 495-511)

| Example | Structure | IC$_{50}$ |
|---|---|---|
| 688 | 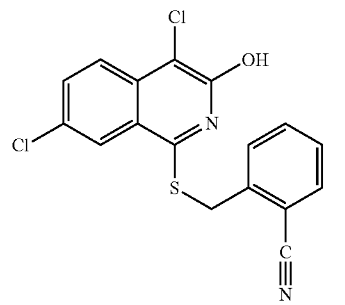 [SMILES: N#Cc1ccccc1CSc1nc(O)c(Cl)c2ccc(Cl)cc12] | 2.3 nM |
| 689 | 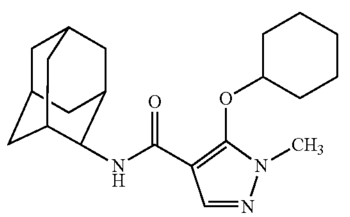 [SMILES: Cn1ncc(C(=O)NC2C3CC4CC(C3)CC2C4)c1OC1CCCCC1] | 18 nM |
| 690 | 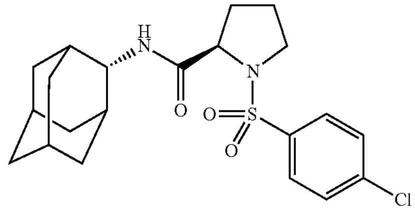 | <0.03 nM |
| 691 | 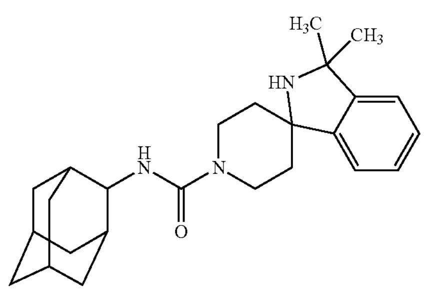 [SMILES: CC1(C)NC2(CCN(C(=O)NC3C4CC5CC(C4)CC3C5)CC2)c2ccccc21] | <50 nM |
| 692 | 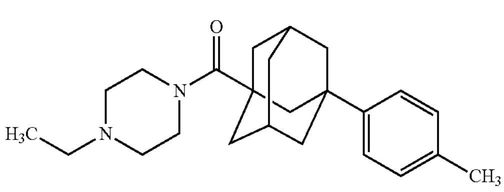 [SMILES: CCN1CCN(C(=O)C23CC4CC(C2)CC(c2ccc(C)cc2)(C4)C3)CC1] | 82 nM |
| 693 | 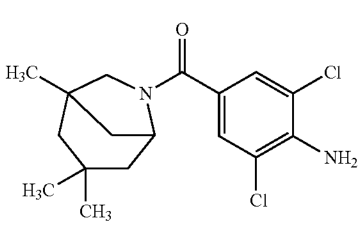 | 4 nM |

TABLE 5-continued
11βHSD-1 Inhibitors (Boyle, C. D. *Current Opinion in Drug Discovery & Development* 2008, 11(4), 495-511)
| Example | Structure | IC$_{50}$ |
|---|---|---|
| 694 | 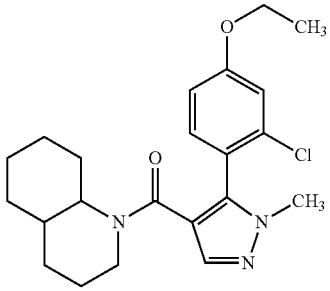 [SMILES: CCOc1ccc(-c2c(C(=O)N3CCCC4CCCCC43)cnn2C)c(Cl)c1] | 21 nM |
| 695 | 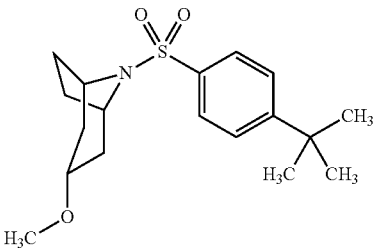 [SMILES: COC1CC2CCC(C1)N2S(=O)(=O)c1ccc(C(C)(C)C)cc1] | 37 nM |
| 696 | 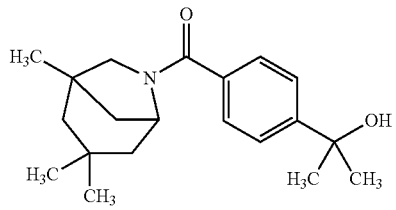 | 7 nM |
| 697 | 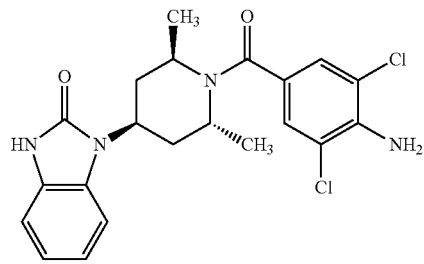 | 22 nM |
| 698 | 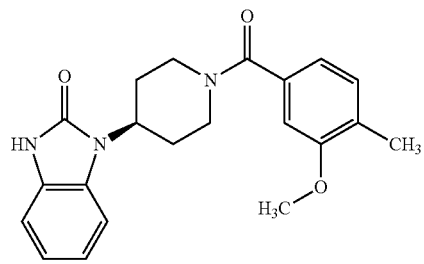 | 110 nM |
| 699 | 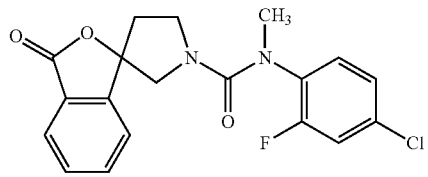 [SMILES: CN(C(=O)N1CCC2(C1)OC(=O)c1ccccc12)c1ccc(Cl)cc1F] | |

TABLE 5-continued
11βHSD-1 Inhibitors (Boyle, C. D. *Current Opinion in Drug Discovery & Development* 2008, 11(4), 495-511)
| Example | Structure | IC$_{50}$ |
|---|---|---|
| 700 | 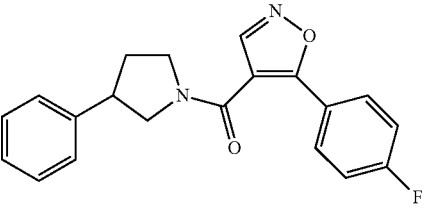 [SMILES: O=C(c1cnoc1-c1ccc(F)cc1)N1CCC(c2ccccc2)C1] | 8 – 10,000 nM |
| 701 | 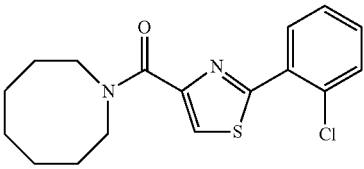 [SMILES: O=C(c1csc(-c2ccccc2Cl)n1)N1CCCCCCC1] | 50 nM |
| 702 | 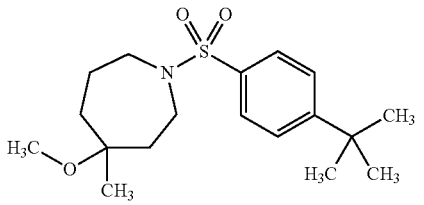 [SMILES: COC1(C)CCCN(S(=O)(=O)c2ccc(C(C)(C)C)cc2)CC1] | 3 nM |
| 703 | 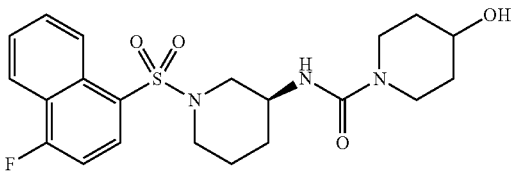 [SMILES: O=C(N[C@H]1CCCN(S(=O)(=O)c2ccc(F)c3ccccc23)C1)N1CCC(O)CC1] | 13 nM |
| 704 | 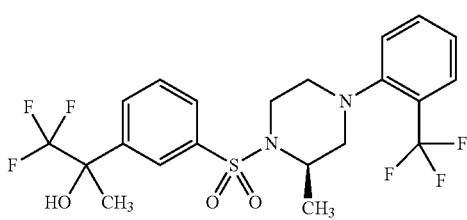 [SMILES: C[C@@H]1CN(c2ccccc2C(F)(F)F)CCN1S(=O)(=O)c1cccc(C(C)(O)C(F)(F)F)c1] | |
| 705 | 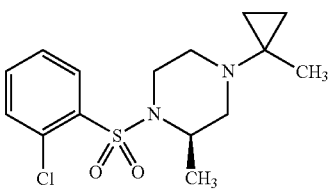 [SMILES: C[C@@H]1CN(C2(C)CC2)CCN1S(=O)(=O)c1ccccc1Cl] | |
| 706 | 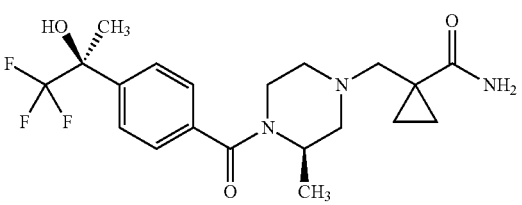 [SMILES: C[C@@H]1CN(CC2(C(N)=O)CC2)CCN1C(=O)c1ccc([C@](C)(O)C(F)(F)F)cc1] | |

TABLE 5-continued
11βHSD-1 Inhibitors (Boyle, C. D. *Current Opinion in Drug Discovery & Development* 2008, 11(4), 495-511)
| Example | Structure | IC$_{50}$ |
| --- | --- | --- |
| 707 | 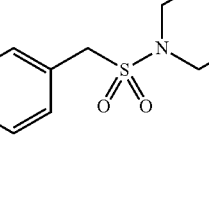 | 430 nM |
| 708 | 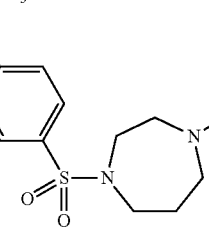 | 19 nM |
| 709 | 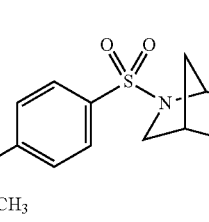 | 40 nM |
| 710 | 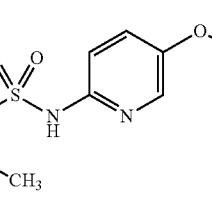 | 5 nM |
| 711 | 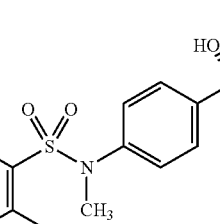 | |
| 712 | 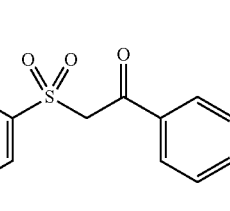 | 187 nM |

TABLE 5-continued

11βHSD-1 Inhibitors (Boyle, C. D. *Current Opinion in Drug Discovery & Development* 2008, 11(4), 495-511)

| Example | Structure | $IC_{50}$ |
|---|---|---|
| 713 | 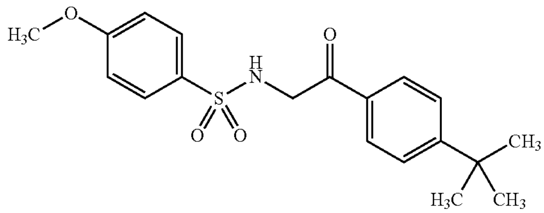 [SMILES: COc1ccc(S(=O)(=O)NCC(=O)c2ccc(C(C)(C)C)cc2)cc1] | 82 nM |

TABLE 6

11βHSD-1 Inhibitors (Rew, Y., et al., *Bioorganic & Medicinal Chemistry Letters*, 19, 1797-1801 (2009))

| Example | Structure | $IC_{50}$ |
|---|---|---|
| 714 | 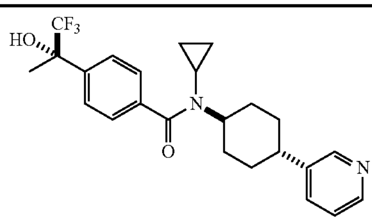 | 1.4 nM |

Compounds including geometric isomers of carbon-carbon double bonds and carbon-nitrogen double are included in the present disclosure. Substituents around a carbon-carbon or a carbon-nitrogen double bond are designated as being of Z or E configuration and substituents around a cycloalkyl or heterocycloalkyl are designated as being of cis or trans configuration. Furthermore, substituents around an adamantane ring system are designated as being of Z or E relative configuration. For examples, see C. D. Jones, et al., J. Org. Chem., Vol. 63 pages 2758-2760, 1998. All geometric isomeric forms and mixtures thereof of the compounds described herein are encompassed within the scope of the present disclosure.

Asymmetric centers exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein and resolved by techniques well known in the art.

Compounds used in the treatment include at least one chiral center and can exist as single stereoisomers (e.g. single enantiomer), mixtures of stereoisomers (e.g. any mixture of enantiomers or diastereomers) or racemic mixtures thereof. As a result, all stereoisomers of the compounds of the disclosure are included in the present disclosure, including racemic mixtures, mixtures of diastereomers, mixtures of enantiomers, as well as individual optical isomers, including, enantiomers and single diastereomers of the compounds of the disclosure substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound. Where the stereochemistry of the chiral centers present in the chemical structures illustrated herein is not specified, the chemical structure is intended to encompass compounds including either stereoisomer of each chiral center present in the compound.

Another embodiment is a method comprising administering an 11-β-HSD-1 inhibitor having an $IC_{50}$ value less than 200 nM, to a mammal in need thereof.

Another embodiment is a method comprising administering an 11-β-HSD-1 inhibitor having an $IC_{50}$ value less than 100 nM, to a mammal in need thereof.

Another embodiment is a method comprising administering an 11β-HSD-1 inhibitor having an $IC_{50}$ value less than 10 nM, to a mammal in need thereof.

Another embodiment is a method comprising administering an 11-β-HSD-1 inhibitor having an $IC_{50}$ value less than 1 nM, to a mammal in need thereof.

Using the methods described in International Publication WO 2007/120656, effective 11β-HSD-1 inhibitors may be determined or confirmed, and, subsequently, used in the method of treating RA. Another embodiment provides a method for determining the efficacy of 11β-HSD-1 inhibitors for treating RA in a subject, using the American College of Rheumatology (ACR) response. The American College of Rheumatology preliminary criteria for improvement in RA (ACR20, 50, 70 responses) was developed to provide an efficacy measures for RA treatments. ACR20, ACR50 and ACR70 requires a greater than 20%, 50% and 70% improvement respectively. Response criteria are detailed in Felson et al., American College of Rheumatology preliminary definition of improvement in rheumatoid arthritis, *Arthritis Rheum.*, 38, 727-35 (1995). Accordingly, an embodiment provides a method of determination of effective dose of treatment comprising administering an 11β-HSD-1 inhibitor to a subject and measuring ACR responses, such as ACR20, ACR50, and ACR70.

Disorders can be treated or prevented in a patient by administering to the patient, a therapeutically effective amount of the compound of the present disclosure in such an amount and for such time as is necessary to achieve the desired result.

The total daily dose of the compounds of the present disclosure necessary to inhibit the action of 11-beta-hydroxysteroid dehydrogenase Type 1 enzyme in single or divided doses can be in amounts, for example, from about 0.01 mg/kg to about 50 mg/kg body weight. In another embodiment, compounds of the present disclosure inhibit the action of 11-beta-hydroxysteroid dehydrogenase Type 1 enzyme in a single or divided doses from about 0.05 mg/kg to about 25 mg/kg body weight. Single dose compositions can contain such amounts or submultiple doses thereof of the compounds of the present disclosure to make up the daily dose. In general, treatment regimens include administration to a patient in need of such treatment from about 1 mg to about 1000 mg of the compounds per day in single or multiple doses.

Another embodiment provides a method for treating RA in a subject such that signs and symptoms are reduced. In one embodiment, the methods include inducing a major clinical response of a subject having RA (WO 2007/120656).

Another embodiment provides methods for determining whether an 11β-HSD-1 inhibitor is effective at treating RA in a subject. Such methods may be used to determine the efficacy of an 11β-HSD-1 inhibitor, including those which are unknown or unconfirmed to have such efficacy. Using the methods described in WO 2007/120656 effective 11β-HSD-1 inhibitors may be determined or confirmed, and, subsequently, used in the method of treating RA.

Another embodiment provides a method of treatment comprising administering an 11β-HSD-1 inhibitor in combination with one or more of drugs selected from corticosteroids, nonsteroidal anti-inflammatory drugs (NSAIDs), analgesics and disease modifying antirheumatic drugs (DMARDs). Corticosteroids include synthetic corticoids such as triamcinolone, methylprednisolone, prednisolone and dexamethasone. NSAIDs include, but are not limited to, acetylsalicylate, naproxen, ibuprofen, etodolac and selective Cox-2 inhibitors like celecoxib. Analgesics include, but are not limited to, creams (capsaicin) or pain medication pills such as propoxyphene or oxycodone. DMARDs include, but are not limited to, etanercept, infliximab, anakinra, adalimumab, rituximab and abatacept. Another embodiment provides methods of treatment comprising administering 11β-HSD-1 inhibitors in combination with TNFα inhibitors, such as anti-INFα human antibodies described in U.S. Pat. Nos. 6,090,382; 6,258,562; 6,509,015, and in U.S. patent application Ser. Nos. 09/801,185 and 10/302,356. In one embodiment, the TNFα inhibitor is an anti-TNFα antibody, or a fragment thereof, including infliximab (U.S. Pat. No. 5,656,272), CDP571 (a humanized monoclonal anti-TNF-alpha IgG4 antibody), CDP 870 (a humanized monoclonal anti-TNF-alpha antibody fragment), an anti-TNF dAb, CNTO 148 (golimumab, WO 02/12502), and adalimumab (a human anti-TNF mAb, described in U.S. Pat. No. 6,090,382 as D2E7). Additional TNF antibodies, which may be used in the method of treatment are described in U.S. Pat. Nos. 6,593,458; 6,498,237; 6,451,983; and 6,448,380. In another embodiment, the TNFα inhibitor is a TNF fusion protein, e.g., etanercept (described in WO 91703553 and WO 09/406,476). In another embodiment, the TNFα inhibitor is a recombinant TNF binding protein (r-TBP-I). Examples of other methods and uses of TNFα inhibitors for the treatment of RA are also described in 60/793,737, 60/812,705, 60/798,149, 60/801,584, 60/858,328, 60/872,753, and 60/857,352.

Another embodiment provides methods of treatment comprising administering 11β-HSD-1 inhibitors in combination with an inhibitor or an antibody to Nerve Growth Factor (NGF) for osteoarthritic, RA, or other inflammatory conditions of pain.

Another embodiment is a method for treating RA comprising administering an effective amount of a pharmaceutical preparation to a patient in need of such treatment.

Another embodiment is a method to treat, control, ameliorate, delay, or prevent the onset of conditions of glucocorticoid-induced or age-dependent osteoporosis comprising administering an effective amount of a pharmaceutical preparation to a patient in need of such treatment.

Another embodiment is a method of determine the efficacy of inhibition of 11-β-HSD-1 in a subject, resulting in protection from prednisolone-induced bone loss comprising administering an 11-β-HSD-1 inhibitor to the subject.

Another embodiment is a method of determine the efficacy of inhibition of 11-β-HSD-1 in a subject, resulting in protection from prednisolone-induced bone loss comprising administering an 11-β-HSD-1 inhibitor to the subject, and measuring bone mineral apposition rate.

Another embodiment is a method of determine the efficacy of inhibition of 11β-HSD-1 in a subject, resulting in protection from prednisolone-induced bone loss comprising administering an 11β-HSD-1 inhibitor to the subject, and bone formation rate/bone volume (BFR/BV).

Another embodiment is a method of determine the efficacy of inhibition of 11-β-HSD-1 in a subject, resulting in protection from prednisolone-induced bone loss comprising administering an 1'-β-HSD-1 inhibitor to the subject, and measuring bone formation rate/bone volume (BFR/BV) and bone mineral apposition rate.

Another embodiment is a method of determine the efficacy of inhibition of 11-β-HSD-1 in a subject, resulting in protection from prednisolone-induced bone loss comprising administering an II-β-HSD-1 inhibitor to the subject, and measuring N-terminal propeptide of type I procollagen (P1NP), bone formation rate/bone volume (BFR/BV), or bone mineral apposition rate, bone formation rate/bone volume (BFR/BV), and bone mineral apposition rate. Another embodiment is a method of determination of an effective dose of an 11β-HSD-1 inhibitor for treating RA comprising administering the 11β-HSD-1 inhibitor to a subject as in claim 1, and measuring N-terminal propeptide of type I procollagen (P1NP), bone formation rate/bone volume (BFR/BV), or bone mineral apposition rate.

Another embodiment is a pharmaceutical preparation comprising at least one 11β-HSD-1 inhibitor, appropriate pharmaceutical excipients and at least one further compound selected from the group consisting of TNF antagonists; TNF antibodies; antagonists of IL-1, IL-5, IL-8, VLA$_4$, VCAM$_1$, LFA$_1$, Mac$_1$, or ICAMs; immunosuppressants; NGF inhibitors or antibodies; and dihydrofolate reductase inhibitors.

Another embodiment is a pharmaceutical preparation comprising an II-β-HSD-1 inhibitor, appropriate pharmaceutical excipients and at least one further compound selected from the group consisting of collagenase, PDGF antagonists and matrix metalloproteinases (MMPs).

One aspect of the disclosure pertains to use of a DVD binding protein comprising binding proteins capable of binding to a first and a second target, in combination with an 11-β-HSD-1 inhibitor. Another embodiment relates to the use of an 11-β-HSD-1 inhibitor in combination with a DVD binding protein capable of binding a first and a second target, wherein the targets are independently selected from the group consisting of TNF, NGF, IL-1, IL-5, and IL-8. Another embodiment relates to the use of an 11-β-HSD-1 inhibitor in combination with a DVD binding protein capable of binding TNF and a second target, wherein the second target is selected from the group consisting of NGF, IL-1, IL-5, and IL-8 (see for example, US Patent Application No. 2009-0311253).

Biological Data
Measurement of Inhibition Constants:

The ability of test compounds to inhibit human 11β-HSD-1 enzymatic activity in vitro was evaluated in a Scintillation Proximity Assay (SPA). Tritiated-cortisone substrate, NADPH cofactor and titrated compound were incubated with truncated human 11β-HSD-1 enzyme (24-287AA) at room temperature to allow the conversion to cortisol to occur. The reaction was stopped by adding a non-specific 11β-HSD inhibitor, 18β-glycyrrhetinic acid. The tritiated cortisol was captured by a mixture of an anti-cortisol monoclonal antibody and SPA beads coated with anti-mouse antibodies. The reaction plate was shaken at room temperature and the radioactivity bound to SPA beads was then measured on a β-scintillation counter. The 11β-HSD-1 assay was carried out in 96-well microtiter plates in a total volume of 220 μl. To start the assay, 188 μl of master mix which contained 17.5 nM $^3$H-cortisone, 157.5 nM cortisone, and 181 mM NADPH was added to the wells. In order to drive the reaction in the forward direction, 1 mM G-6-P was also added. Solid compound was dissolved in DMSO to make a 10 mM stock followed by a subsequent 10-fold dilution with 3% DMSO in Tris/EDTA buffer (pH 7.4). 22 μl of titrated compounds was then added in triplicate to the substrate. Reactions were initiated by the addition of 10 μl of 0.1 mg/ml E. coli lysates overexpressing 11β-HSD-1 enzyme. After shaking and incubating plates for 30 minutes at room temperature, reactions were stopped by adding 10 μl of 1 mM glycyrrhetinic acid. The product, tritiated cortisol, was captured by adding 10 μl of 1 μM monoclonal anti-cortisol antibodies and 100 μl SPA beads coated with anti-mouse antibodies. After shaking for 30 minutes, plates were read on a liquid scintillation counter Topcount. Percent inhibition was calculated based on the background and the maximal signal. Wells that contained substrate without compound or enzyme were used as the background, while the wells that contained substrate and enzyme without any compound were considered as maximal signal. Percent of inhibition of each compound was calculated relative to the maximal signal and IC$_{50}$ curves were generated. This assay was applied to 11β-HSD-2 as well, whereby tritiated cortisol and NAD$^+$ were used as substrate and cofactor, respectively.

Compounds of the present disclosure are active in the 11β-HSD-1 SPA assay described above, and show selectivity for human 11β-HSD-1 over human 11β-HSD-2, as indicated in Table 7.

TABLE 7

Human 11β-HSD-1 and 11β-HSD-2 enzymatic SPA assay.

| Compound | 11β-HSD-1 IC$_{50}$ (nM) | 11β-HSD-2 IC$_{50}$ (nM) |
|---|---|---|
| 2-[(cis)-2,6-dimethylmorpholin-4-yl]-n-[(e)-5-hydroxy-2-adamantyl]propanamide | 110 | >10,000 |
| 2-azepan-1-yl-n-[(e)-5-hydroxy-2-adamantyl]propanamide | 92 | >10,000 |
| (E)-4-[({4-[5-(Trifluoromethyl)pyridin-2-yl]piperazin-1-yl}acetyl)amino]-1-adamantyl carbamate | 150 | >10,000 |
| N-[(e)-5-fluoro-2-adamantyl]-2-{4-[5-(trifluoromethyl)pyridin-2-yl]piperazin-1-yl}acetamide | 140 | >10,000 |
| N-[(Z)-5-Fluoro-2-adamantyl]-2-{4-[5-(trifluoromethyl)pyridin-2-yl]piperazin-1-yl}acetamide | 82 | >10,000 |
| (E)-4-({2-Methyl-2-[(2S)-2-methyl-4-pyridin-2-ylpiperazin-1-yl]propanoyl}amino)adamantane-1-carboxylic acid | 53 | >30,000 |
| (E)-4-{[2-Methyl-2-(4-pyridin-2-ylpiperazin-1-yl)propanoyl]amino}adamantane-1-carboxamide | 37 | >30,000 |
| (E)-4-{[2-Methyl-2-(4-pyrazin-2-ylpiperazin-1-yl)propanoyl]amino}adamantane-1-carboxamide | 35 | >30,000 |
| N-{(E)-5-[(Methylsulfonyl)amino]-2-adamantyl}-2-{4-[5-(trifluoromethyl)pyridin-2-yl]piperazin-1-yl}propanamide | 67 | >30,000 |
| {(E)-4-[(2-methyl-2-{4-[5-(trifluoromethyl)pyridin-2-yl]piperazin-1-yl}propanoyl)amino]-1-adamantyl}acetic acid | 80 | >10,000 |
| (E)-4-({2-[(3R)-3-Fluoropyrrolidin-1-yl]-2-methylpropanoyl}amino)adamantane-1-carboxylic acid | 58 | >10,000 |
| E-4-[2-Methyl-2-(4-(trifluoromethyl-benzyloxy)-propionylamino]-adamantane-1-carboxylic acid amide | 28 | >10,000 |
| E-4-[2-Methyl-2-(2-methyl-cyclohexyloxy)-propionylamino]-adamantane-1-carboxylic acid | 35 | 10,000 |
| E-4-(2-Cycloheptyloxy-2-methyl-propionylamino)-adamantane-1-carboxylic acid | 35 | |
| E-4-(2-(Cyclohexylmethoxy-2-methyl-propionylamino)-adamantane-1-carboxylic acid | 34 | |
| E-4-[2-(4-Chloro-phenoxy)-2-methyl-propionylamino]-adamantane-1-carboxylic acid | 72 | 29,000 |
| E-4-{[2-(4-methoxyphenoxy)-2-methylpropanoyl]amino}adamantane-1-carboxamide | 24 | 32,000 |
| E-4-({2-methyl-2-[3-(trifluoromethyl)phenoxy]propanoyl}amino)adamantane-1-carboxamide | 44 | 11,000 |
| E-4-({2-Methyl-2-[4-(trifluoromethoxy)phenoxy]propanoyl}amino)adamantane-1-carboxamide | 40 | 2,600 |
| 4-({[((E)-4-{[2-(4-Chlorophenoxy)-2-methylpropanoyl]amino}-1-adamantyl)carbonyl]amino}methyl)benzoic acid | 38 | 15,000 |
| tert-Butyl 4-(2-{[(E)-5-(aminocarbonyl)-2-adamantyl]amino}-1,1-dimethyl-2-oxoethoxy)phenylcarbamate | 45 | 37,000 |
| E-4-{[2-(4-Hydroxyphenoxy)-2-methylpropanoyl]amino}adamantane-1-carboxamide | 18 | 35,000 |
| ((E)-4-{[2-(4-Chlorophenoxy)-2-methylpropanoyl]amino}-1-adamantyl)acetic acid | 45 | 59,000 |

TABLE 7-continued

Human 11β-HSD-1 and 11β-HSD-2 enzymatic SPA assay.

| Compound | 11β-HSD-1 IC$_{50}$ (nM) | 11β-HSD-2 IC$_{50}$ (nM) |
|---|---|---|
| N-[(E)-5-(2-Amino-2-oxoethyl)-2-adamantyl]-2-(4-chlorophenoxy)-2-methylpropanamide | 43 | 21,000 |
| 2-(4-Chlorophenoxy)-2-methyl-N-[(E)-5-(2H-tetraazol-5-ylmethyl)-2-adamantyl]propanamide | 41 | >100,000 |
| N-{(E)-5-[(Aminosulfonyl)methyl]-2-adamantyl}-2-(4-chlorophenoxy)-2-methylpropanamide | 96 | 100,000 |
| N-{(E)-5-[(Z)-Amino(hydroxyimino)methyl]-2-adamantyl}-2-(4-chlorophenoxy)-2-methylpropanamide | 41 | >100,000 |
| E-4-({2-[(4-Methoxyphenyl)thio]-2-methylpropanoyl}amino)adamantane-1-carboxamide amide | 29 | 10,000 |
| E-4-[(2-{4-Chloro-2-[(diethylamino)sulfonyl]phenoxy}-2-methylpropanoyl)amino]adamantane-1-carboxamide | 68 | 65,000 |
| 2-(2-Chloro-4-fluorophenoxy)-2-methyl-N-[(E)-5-(methylsulfonyl)-2-adamantyl]propanamide | 53 | 10,000 |
| 2-(2-Chloro-4-fluorophenoxy)-2-methyl-N-[(E)-5-(methylsulfinyl)-2-adamantyl]propanamide | 28 | 10,000 |
| N-[(E)-5-(Aminosulfonyl)-2-adamantyl]-2-(4-chlorophenoxy)-2-methylpropanamide | 26 | 14,000 |
| E-4-({[1-(4-Chlorophenoxy)cyclobutyl]carbonyl}amino)adamantane-1-carboxamide | 89 | 90,000 |
| 4-[({[((E)-4-{[2-(4-Chlorophenoxy)-2-methylpropanoyl]amino}-1-adamantyl)methyl]sulfonyl}amino)methyl]benzoic acid | 48 | 18,000 |
| (2E)-3-((E)-4-{[2-(4-Chlorophenoxy)-2-methylpropanoyl]amino}-1-adamantyl)acrylic acid | 30 | >100,000 |
| (E)-4-[(2-Methyl-2-{5-(1H-pyrazol-1-yl)pyridin-2-yl]oxy}propanoyl)amino]adamantane-1-carboxamide | 30 | >100,000 |
| N-[(E)-5-(Aminosulfonyl)-2-adamantyl]-2-(2-chloro-4-fluorophenoxy)-2-methylpropanamide | 89 | >100,000 |
| E-4-{[1-(4-Chloro-phenyl)-cyclobutanecarbonyl]-amino}-adamantane-1-carboxylic acid | 43 | >10,000 |
| E-4-[(1-Phenyl-cyclopropanecarbonyl)-amino]-adamantane-1-carboxylic acid | 102 | |
| E-4-(2-methyl-2-phenyl-propionylamino)-adamantane-1-carboxylic acid | 82 | >10,000 |
| E-4-{[1-(4-chloro-phenyl)-cyclobutanecarbonyl]-amino}-adamantane-1-carboxylic acid amide | 24 | |
| E-4-({[1-(4-chlorophenyl)cyclohexyl]carbonyl}amino)adamantane-1-carboxamide | 59 | 7,400 |
| E-4-({[1-(4-chlorophenyl)cyclopropyl]carbonyl}amino)adamantane-1-carboxamide | 33 | >30,000 |
| E-4-({[1-(4-chlorophenyl)cyclopentyl]carbonyl}amino)adamantane-1-carboxamide | 35 | 12,000 |
| E-4-{[2-(4-chlorophenyl)-2-methylpropanoyl]amino}adamantine-1-carboxamide | 33 | 30,000 |
| E-4-{[(1-phenylcyclopentyl)carbonyl]amino}adamantane-1-carboxamide | 43 | 16,000 |
| E-4-({[1-(3-fluorophenyl)cyclopentyl]carbonyl}amino)adamantane-1-carboxamide | 25 | 16,000 |
| E-4-({[1-(2-chloro-4-fluorophenyl)cyclopentyl]carbonyl}amino)adamantane-1-carboxamide | 30 | >30,000 |
| E-4-({[1-(4-fluorophenyl)cyclopentyl]carbonyl}amino)adamantane-1-carboxamide | 31 | >30,000 |
| E-4-({[1-(2-fluorophenyl)cyclopentyl]carbonyl}amino)adamantane-1-carboxamide | 38 | 16,000 |
| E-4-{[(1-methylcyclohexyl)carbonyl]amino}adamantane-1-carboxamide | 38 | >30,000 |
| E-4-({[1-(2,4-dichlorophenyl)cyclopropyl]carbonyl}amino)adamantane-1-carboxamide | 36 | 16,000 |
| E-4-({[1-(4-methoxyphenyl)cyclopropyl]carbonyl}amino)adamantane-1-carboxamide | 27 | 21,000 |
| E-4-({[1-(4-methylphenyl)cyclopropyl]carbonyl}amino)adamantane-1-carboxamide | 37 | 15,000 |
| E-4-{[2-methyl-2-(4-pyridin-4-ylphenyl)propanoyl]amino}adamantine-1-carboxamide | 31 | >30,000 |
| E-4-[(2-methyl-2-thien-2-ylpropanoyl)amino]adamantane-1-carboxamide | 16 | 12,000 |
| E-4-[(2-methyl-2-thien-3-ylpropanoyl)amino]adamantane-1-carboxamide | 19 | 15,000 |
| E-4-({2-methyl-2-[5-(trifluoromethyl)pyridin-2-yl]propanoyl}amino)adamantane-1-carboxamide | 23 | >30,000 |
| E-4-[(2-methyl-2-{4-[5-(trifluoromethyl)pyridin-2-yl]phenyl}propanoyl)amino]adamantane-1-carboxamide | 104 | >30,000 |
| E-4-({[1-(4-methoxyphenyl)cyclopentyl]carbonyl}amino)adamantane-1-carboxamide | 18 | 13,000 |

TABLE 7-continued

Human 11β-HSD-1 and 11β-HSD-2 enzymatic SPA assay.

| Compound | 11β-HSD-1 IC$_{50}$ (nM) | 11β-HSD-2 IC$_{50}$ (nM) |
|---|---|---|
| E-4-{[2-(4-bromophenyl)-2-methylpropanoyl]amino} adamantane-1-carboxamide | 21 | 23,000 |
| E-4-[5-(aminocarbonyl)-2-adamantyl]-3-methyl-1-(2-methylbenzyl)-2-oxopiperidine-3-carboxamide | 15 | 15,000 |
| E-4-(aminocarbonyl)-2-adamantyl]-1-benzyl-3-methyl-2-oxopyrrolidine-3-carboxamide | 26 | 30,000 |
| E-4-(aminocarbonyl)-2-adamantyl]-3-methyl-1-(2-methylbenzyl)-2-oxopyrrolidine-3-carboxamide | 23 | 12,000 |
| E-4-(aminocarbonyl)-2-adamantyl]-1-(2-chlorobenzyl)-3-methyl-2-oxopyrrolidine-3-carboxamide | 23 | 6,300 |
| E-4-(aminocarbonyl)-2-adamantyl]-1-(3-chlorobenzyl)-3-methyl-2-oxopyrrolidine-3-carboxamide | 29 | 10,000 |
| E-4-({2-methyl-2-[4-(1-methyl-1H-pyrazol-4-yl)phenyl]propanoyl}amino)adamantane-1-carboxamide | 28 | >100,000 |
| E-4-{[2-(3-bromophenyl)-2-methylpropanoyl]amino} adamantine-1-carboxamide | 17 | 9,300 |
| E-4-({2-[4-(3,5-dimethylisoxazol-4-yl)phenyl]-2-methylpropanoyl}amino)adamantane-1-carboxamide | 44 | 40,000 |
| E-4-{[2-methyl-2-(4-pyridin-3-yl)phenyl)propanoyl]amino}adamantane-1-carboxamide | 62 | 44,000 |
| 4-{[({(E)-4-[(2-methyl-2-thien-2-ylpropanoyl)amino]-1-adamantyl}carbonyl)amino]methyl}benzoic acid | 95 | 60,000 |
| 9-(4-{[(5-cyanopyridin-2-yl)oxy]methyl}-3,3-dimethyl-2-oxopyrrolidin-1-yl)bicyclo[3.3.1]nonane-3-carboxamide | 51 | 8,280 |
| B E-4-(4-{[(5-cyanopyridin-2-yl)oxy]methyl}-3,3-dimethyl-2-oxopyrrolidin-1-yl)adamantane-1-carbonitrile | 29 | 5,270 |
| 1-cycloheptyl-4-{[(2-fluorophenyl)(methyl)amino]methyl}-3,3-dimethylpyrrolidin-2-one | 73 | >10,000 |
| 1-cycloheptyl-3,3-dimethyl-4-(phenoxymethyl)pyrrolidin-2-one | 95 | >8,750 |
| E-4-(4-{[(5-cyanopyridin-2-yl)oxy]methyl}-3,3-dimethyl-2-oxopyrrolidin-1-yl)adamantane-1-carboxamide | 29 | 5,170 |
| 6-[(l-cycloheptyl-4,4-dimethyl-5-oxopyrrolidin-3-yl)methoxy]nicotinonitrile | 62 | >10,000 |
| 6-{[4,4-dimethyl-1-(4-methylbicyclo[2.2.2]oct-1-yl)-5-oxopyrrolidin-3-yl]methoxy}nicotinonitrile | 77 | 8,470 |
| E-4-(4-{[4-(1H-imidazol-1-yl)phenoxy]methyl}-3,3-dimethyl-2-oxopyrrolidin-1-yl)adamantane-1-carboxamide | 76 | 1,850 |
| E-4-[3,3-dimethyl-2-oxo-4-({[5-(trifluoromethyl)pyridin-2-yl]oxy}methyl)pyrrolidin-1-yl]adamantane-1-carboximidamide | 51 | 90,000 |
| E-4-[3,3-dimethyl-2-oxo-4-({[5-(trifluoromethyl)pyridin-2-yl]oxy}methyl)pyrrolidin-1-yl]-N'-hydroxyadamantane-1-carboximidamide | 99 | 13,900 |
| E-4-(3,3-dimethyl-2-oxo-4-{[4-(1H-1,2,4-triazol-1-yl)phenoxy]methyl}pyrrolidin-1-yl)adamantane-1-carboxamide | 41 | 1,600 |
| E-4-[3,3-dimethyl-2-oxo-4-({[5-(trifluoromethyl)pyridin-2-yl]oxy}methyl)pyrrolidin-1-yl]adamantane-1-carboxamide | 39 | 1,360 |

Evaluation of Effects of 11β-HSD-1 Inhibitors on Prednisolone-Induced Osteocalcin Release Prednisolone (active GC) administration to rats induces a variety of acute physiological effects including an increase in liver tyrosine amino transferase, increase in serum free fatty acids, increase in liver glycogen levels, hyperglycemia, decrease in osteocalcin, among others. Osteocalcin is of particular interest since a decrease in this hormone leads to decreased bone formation, increasing the potential for osteoporosis. Administration of an 11β-HSD-1 inhibitor would be expected to reduce local reactivation of prednisolone from prednisone in the bone or relevant tissue, and thereby reduce loss of osteocalin levels. When prednisolone is normally administered, it acts as the active hormone, but it is also converted to its inactive form, prednisone, in the kidney by HSD2. Prednisone is reactivated, however, to prednisolone in the liver, bone and other tissues where 11β-HSD-1 is expressed. By blocking this reactivation through the use of an 11β-HSD-1 inhibitor, the exposure of active glucocorticoid in bone would be minimized. This example would pertain to normal older individuals as well where cortisol levels increase with age, and likely contribute to age-dependent osteoporosis. This would be an acute study design. To validate this hypothesis, effects of the 11β-HSD-1 inhibitor (compound A) on prednisolone-induced osteocalcin reduction was evaluated in rats using two separate protocols as indicated in the Table 8 below.

TABLE 8

| Pre-treatment | | Sacrifice | (EDTA plasma) | |
|---|---|---|---|---|
| (t = minus 1 h) | Treatment (t = 0) | t = 0 n | t = 2 h n | t = 4 h n |
| Study A | | | | |
| Vehicle (HPMC, po) | Vehicle | 8 | 8 | 8 |
| Vehicle (HPMC, po) | Prednisolone (10 mg/kg, po) | x | 8 | 8 |

TABLE 8-continued

| Pre-treatment | | Sacrifice | (EDTA plasma) | |
|---|---|---|---|---|
| (t = minus 1 h) | Treatment (t = 0) | t = 0 n | t = 2 h n | t = 4 h n |
| Compound A (30 mg/kg, po) | Vehicle (HPMC) | x | 8 | 8 |
| Compound A (30 mg/kg, po) | Prednisolone (10 mg/kg, po) | x | 8 | 8 |
| | TOTAL | 8 | 32 | 32 |
| Study B | | | | |
| Vehicle (HPMC, po) | Vehicle | 8 | 8 | 8 |
| Vehicle (HPMC, po) | Prednisone (10 mg/kg, po) | x | 8 | 8 |
| Compound A (30 mg/kg, po) | Vehicle (HPMC) | x | 8 | 8 |
| Compound A (30 mg/kg, po) | Prednisone (10 mg/kg, po) | x | 8 | 8 |
| | TOTAL | 8 | 32 | 32 |

In Study A, rats were pre-dosed with Compound A at 30 mg/kg 1 hour prior to administration with the active glucocorticoid, prednisolone, at 10 mg/kg, po. At 2 and 4 hours after dosing prednisolone, rats were sacrificed, and blood evaluated for levels of osteocalcin. Since prednisolone is the active glucocorticoid, and is not generated via 11β-HSD-1, it was expected that Compound A would have no effect on osteocalcin reduction. This is demonstrated in FIG. 1. At the 4 hour time point, rats pre-treated with vehicle or prednisolone had significant reductions in plasma osteocalcin. Pre-treatment with Compound A did not prevent the significant reduction of osteocalcin induced by prednisolone.

Figure 2:
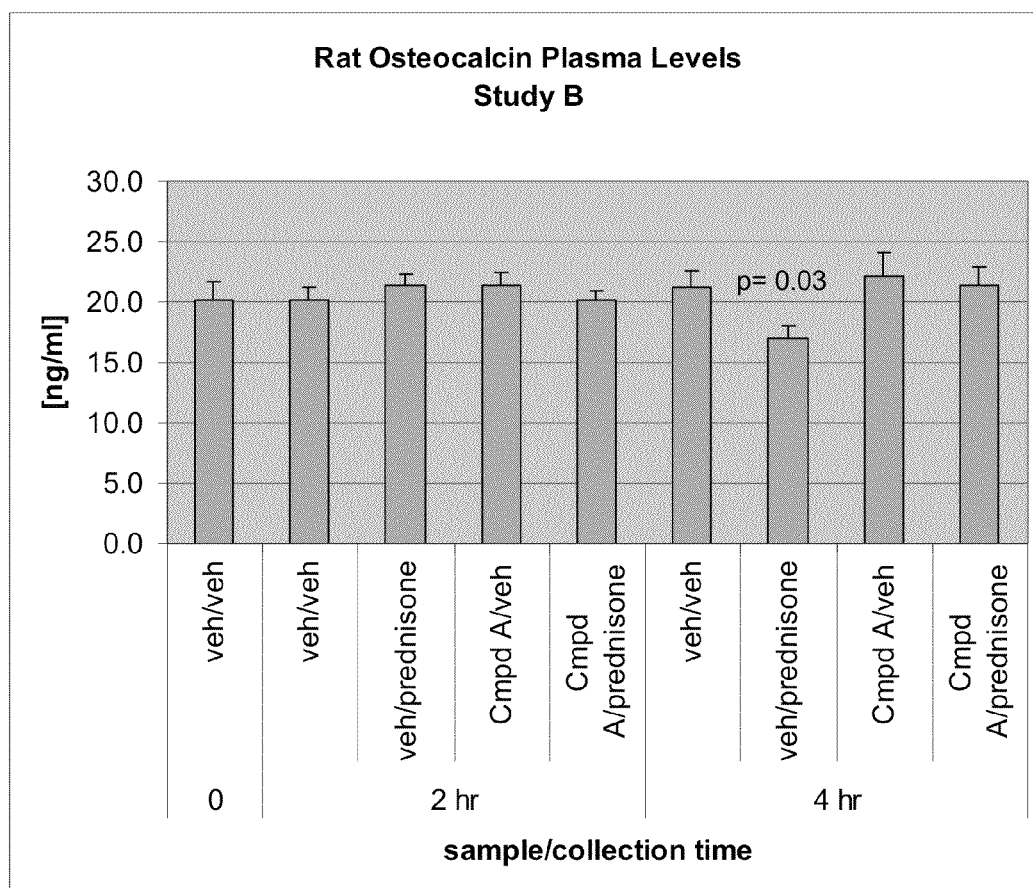
FIG. 2 shows the results of study B where the inactive glucocorticoid prednisone was administered to rats at 10 mg/kg, 1 hour after administration of the 11β-HSD-1 inhibitor Compound A, and osteocalcin levels measured 2 and 4 hours later. As shown in this FIG. 2, pre-treatment of rats with vehicle, followed by the prednisone challenge, resulted in a significant reduction in plasma osteocalcin 4 hours later due to conversion of inactive prednisone to active prednisolone via 11β-HSD-1. In contrast, when rats were pre-treated with Compound A, and then challenged with prednisone, no reduction in osteocalin was observed, demonstrating that 11β-HSD-1 inhibition can prevent glucocorticoid-induced reductions in osteocalcin levels.

In Study B, the inactive glucocorticoid prednisone was administered at 10 mg/kg, 1 hour after administration of the 11β-HSD-1 inhibitor, Compound A, and osteocalcin levels measured 2 and 4 hours later. As shown in FIG. 2, pre-treatment of rats with vehicle, followed by the prednisone challenge, resulted in a significant reduction in plasma osteocalcin 4 hours later due to conversion of inactive prednisone to active prednisolone via 11β-HSD-1. However, when rats were pre-treated with Compound A, and then challenged with prednisone, no reduction in osteocalin was observed, demonstrating that 11β-HSD-1 inhibition can prevent glucocorticoid-induced reductions in osteocalcin levels by blocking the conversion of inactive to active glucocorticoids.

Evaluation of 11β-HSD-1 Inhibitors in a Mouse Model of Glucocorticoid-Induced Osteoporosis Purpose: The purpose of this experiment was to determine if inhibiting 11β-HSD-1 in mice results in protection from prednisolone-induced bone loss over a 28-day period, while maintaining the same anti-inflammatory efficacy against lipopolysaccharide(LPS)-induced TNFα.

Animals: Female Swiss Webster mice from Charles River Laboratories (CFW mice) were used in this study. Mice were 10 weeks old at the start of the study. Two identical prednisolone dose responses were run with a vehicle control (n=12), 5, 1.5, and 0.5 mg/kg dosed for 28 days (n=8 each), and 1.5 mg/kg dosed for 27 days (n=8, to determine if prednisolone needed to be on board to affect tumor necrosis factor-alpha (TNFα), procollagen type 1 N-terminal propeptide(P1NP), and Osteocalcin). One set of animals received control diet while the other set received diet containing 2-(2-chloro-4-fluorophenoxy)-2-methyl-N-[(E)-5-(methylsulfonyl)-2-adamantyl]propanamide (Compound B). The groups were labeled A (vehicle control), B (5 mg/kg prednisolone), C (1.5 mg/kg prednisolone), D (1.5 mg/kg prednisolone), and E (0.5 mg/kg prednisolone) received the diet without the 11b-HSD-1 inhibitor. By contrast, the groups were labeled F (vehicle control), G (5 mg/kg prednisolone), H (1.5 mg/kg prednisolone), I (1.5 mg/kg prednisolone), and J (0.5 mg/kg prednisolone) received the diet with the 11b-HSD-1 inhibitor. The total number of animals used was 88.

Experimental Design: All animals were placed on the control diet (Research Diets Rodent Diet with 60 kcal % Fat: D12492i) upon arrival. Half of the animals (44) were converted to the diet containing Compound B (Research Diets Rodent Diet with 60 kcal % Fat and 873 mg Compound B/kg: D07113001i) two days before the start of the study. Also on this day, animals were weighed for baselines and ear-tagged for identification. On day 1 of the study, all animals were injected intraperitoneally (i.p.) with 10 mg/kg of calcein (Sigma #C0875) in 2% sodium bicarbonate (Sigma #S6014, dissolved in deionized water). Animals were then given an oral (p.o.) dose of vehicle (0.5% hydroxyproplymethylcellulose(HPMC) [Sigma #H3785]/0.02% Tween 80 [Sigma #P-4780]) or prednisolone (Sigma #P6004) at 5, 1.5, and 0.5 mg/kg. Animals were then dosed daily with vehicle or prednisolone from days 1-28, or days 1-27 for groups D and I. Animals were weighed once a week and prednisolone and fluorescent label formulations were adjusted based on average weight. On day 15, all animals were injected intraperitoneally (i.p.) with 80 mg/kg xylenol orange (Baker #584-02). On day 26, all animals were injected i.p. with 25 mg/kg tetracycline (Sigma #87128, lot 0001428858). On day 27, 4 animals from each vehicle control group were challenged with 5 mg/kg of 11-dehydrocorticosterone (11-DHC [Steraloids #Q3690-000]) p.o., and plasma was collected 30 minutes later for corticosterone analysis by mass spec. On day 28, groups A-C, E, F-H, and J were given the last prednisolone dose. Thirty minutes later, all groups were challenged with 0.1 mg/kg of LPS (Sigma #L4130) to induce TNFα. Animals were bled by cardiac puncture 90 minutes after LPS challenge, and plasma was collected in lithium-heparin microtainers (BD #365958) for assessing TNFα (ELISA, R&D Systems #MTA00), P1NP (N-terminal propeptide of type I procollagen [ELISA, Immunodiagnostic Systems #AC-33F1], and Osteocalcin (Milliplex, Millipore #MBN-41K-1OC) levels. Right leg bones, left leg bones, and the spinal columns of all mice were collected and stored as follows:

Right leg bones were removed from the animal and cleaned of most muscle. The femur was cut at the third trochanter (just below the femoral head), and the tibia was cut just below the tibial-fibular junction, using a scalpel. Legs were left intact, and placed in individual glass vials containing 70% ethanol (Decon Laboratories #2401). Samples were stored at 4° C.

Left leg bones were removed, cleaned, and cut identically to the right leg bones. However, left legs were separated at the knee joint by carefully teasing apart with a scalpel. Femurs and tibias were placed in individual cassettes and fixed in 4% paraformaldehyde (32% Paraformaldehyde [Electron Microscopy Sciences #15714-S] was diluted in phosphate buffered saline (PBS) to 4%). After 48 hours in 4% paraformaldehyde, femurs were transferred to 30% sucrose (USB #21938, dissolved in deionized water). Three days following the transfer to sucrose, femurs were frozen in 3.5% carboxy methylcellulose (CMC) [Sigma #C4888 CAS#9004-32-4], dissolved in deionized water) for sectioning and histomorphometric analysis. After 24 hours in 4% paraformaldehyde, tibias were decalcified in 12.7% ethylenediaminetetraacetic acid (EDTA) solution, and embedded in paraffin for a potential TRACP-5b stain and analysis.

Spinal columns were removed by cutting between the hip joints and at the rib cage (leaving some ribs intact). Spines were carefully cut out by trimming up the sides until free from the body. Spines were then placed in cassettes and stored in 70% ethanol at 4° C.

N-terminal propeptide of type I procollagen (PINP) was measured using the Rat/Mouse PINP EIA kit from Immunodiagnostic Systems. The protocol was followed as outlined in the kit, except for that sample dilutions were made in a separate plate instead of directly in the ELISA plate. Samples were read using a Molecular Devices Spectra Max 190 plate reader and Soft Max Pro 5.2 software. Results shown in Table 9 demonstrate a significant reduction in prednisolone-induced release of P1NP in the presence of the 11β-HSD-1 inhibitor (18% vs. 51% in absence of inhibitor). This data suggests that administration of a selective 11β-HSD-1 inhibitor may ameliorate glucocorticoid-induced bone loss as reflected by reduced levels of P1NP.

TABLE 9

| Prednisolone | P1NP (N-Terminal Propeptide of Type-1 Procollagen) % Inhibition of P1NP | |
| --- | --- | --- |
| Dose (mg/kg) | (−) Inhibitor | (+) Inhibitior |
| 0.5 | 33% | 25% |
| 1.5 | 40% | 28% |
| 5 | 51% | 18%* |

*p < 0.001 vs. 5 mg/kg prednisolone (−) inhibitor

Osteocalcin was measured using the Millipore Milliplex Mouse Osteocalcin Single-Plex Kit. The protocol was followed exactly as outlined in the kit. Samples were read on a BioRad Bio-Plex System, model # Luminex 100 and Bio-Plex Manager 4.1.1 software. Results are shown in Table 10. As with P1NP, prednisolone-induced reduction of osteocalcin was significantly attenuated in both the 1.5 and 5 mg/kg prednisolone groups.

TABLE 10

| Prednisolone | Osteocalcin % Inhibition of Osteocalcin | |
| --- | --- | --- |
| Dose (mg/kg) | (−) Inhibitor | (+) Inhibitor |
| 0.5 | 10% | 18% |
| 1.5 | 35% | 10%^ |
| 5 | 45% | 28%* |

^p < 0.01 vs 1.5 mg/kg prednisolone (−) inhibitor
*p < 0.05 vs. 5 mg/kg prednisolone (−) inhibitor TNFα was measured using the Mouse INFα/TNFSF1A Quantikine ELISA kit from R&D Systems. The protocol was followed as outlined in the kit. Samples were read using a Molecular Devices Spectra Max 250 plate reader and Soft Max Pro 4.8 software. Results are shown in Table 11. TNFα was not significantly inhibited in the presence of inhibitor, suggesting that in this acute inflammatory LPS challenge model, the presence of an 11β-HSD-1 inhibitor does not impact the anti-inflammatory effects of prednisolone on TNFα production.

TABLE 11

| Prednisolone | TNFα % Inhibition of TNFα$ | |
| --- | --- | --- |
| Dose (mg/kg) | (−) Inhibitor | (+) Inhibitor |
| 0.5 | 80% | 80% |
| 1.5 | 95% | 94% |
| 5 | 98% | 98% |

$p < 0.001 vs. vehicle control for all doses

Femurs were fixed in 4% paraformaldehyde for 48 hours, and transferred to 30% sucrose for 24 hours before embedding in a CMC (carboxymethylcellulose) block. Blocks were frozen in liquid nitrogen-cooled hexanes (−60° C. or colder) for 3-5 minutes, and stored at −80° C. Femurs were then sectioned on a cryomicrotome. Sections of 4 or 5 μM were collected at the midvein and bonded to microscope slides using the Cryojane tape transfer system, and cover-slipped for histomorphometric measurements.

Trabecular bone parameters were measured in the secondary spongiosa of the distal femur, beginning 0.5 mm distal to the growth plate, and extending 1.16-2.45 mm. Bone was measured from 8-10 fields per femur, with each field being 400×500 microns in size. All dynamic measurement calculations were made from scoring the second and third fluorochrome labels, which were administered 11 days apart. OsteoMeasure software was used to obtain all values.

Bone formation rate/bone volume (BFR/BV) refers to the volume of new bone formed per unit of time, and is measured as a percent per day. BFR is the most significant measure of bone formation. Results are shown in Table 12. A significant difference was observed in both dose groups in the presence of the inhibitor suggesting 11β-HSD-1 inhibition has the potential to increase bone formation rate in trabecular bone.

TABLE 12

| Bone Formation Rate/Bone Volume (BFR/BV) (Trabecular bone at Femoral Metaphysis) | | |
| --- | --- | --- |
| Prednisolone Dose (mg/kg) | % Inhibition of BFR/BV (−) Inhibitor | % Increase in BFR/BV (+) Inhibitor |
| 0.5 | No Inhibition | 47%# |
| 5 | 27% | 30%* |

*p < 0.05 vs. 5 mg/kg prednisolone (−) inhibitor
p < 0.05 vs. vehicle control

Mineral apposition rate (MAR) refers to the distance between two fluorochrome labels divided by the number of days between label administration, and is indicative of osteoblastic activity. Results are shown in Table 13, indicating that in the presence of inhibitor, there was a trend toward reduced inhibition of MAR as a result of prednisolone treatment.

TABLE 13

| Prednisolone | Mineral Apposition Rate (MAR) (Trabecular bone at Femoral Metaphysis) % Inhibition of MAR | |
| --- | --- | --- |
| Dose (mg/kg) | (−) Inhibitor | (+) Inhibitor |
| 0.5 | 33% | 9% |
| 5 | 52% | 23% |

Double labeled surface/bone surface (dLS/BS) refers to the percentage of trabecular bone surface which is double-labeled, and is another readout indicative of bone formation. Results are shown in Table 14 where a significant dose-dependent increase in trabecular bone was observed in the presence of the inhibitor.

TABLE 14

% Double Labeled Surface/Bone Surface (dLS/BS)
(Trabecular bone at Femoral Metaphysis)

| Prednisolone | % Increase in dLS/BS | |
|---|---|---|
| Dose (mg/kg) | (−) Inhibitor | (+) Inhibitor |
| 0.5 | No Increase | 22%[#] |
| 5 | No Increase | 46%[#] |

[#]p < 0.05 vs. vehicle control

Evaluation of Effects of 11β-HSD-1 Inhibitors in Chronic Neuropathic Pain

Glucocorticoids serve a protective role early in inflammatory and pain responses, but may contribute to the progression of the inflammatory diseases and neuropathic pain, following chronic exposure. Dysregulation of the immune system and hypothalamic pituitary adrenal (HPA) axis promote alterations in brain circuitry that modulate mood, pain, and HPA responsiveness. Over time, these changes promote phenotypic changes in macrophages, neutrophils, microglia, astrocytes, and other inflammatory cells that contribute to glia-neuronal reactivity, and contribute to the process of central sensitization of pain, as well as other CNS disorders. Activated glia (mainly microglia, astrocytes, and infiltrating immune-like cells) at the level of the spinal cord and dorsal root ganglion (DRG) clearly play an important role in the development and maintenance of neuropathic, inflammatory and post-operative pain. Inhibition of 11β-HSD-1 should reduce local levels of active glucocorticoids in the spinal cord, DRG, and in the brain, thereby reversing glucocorticoid-induced changes in microglial function, and reducing the activation state of microglia which are known to contribute to development and maintenance of neuropathic pain (Alexander et al., Brain Behav Immun 23(6): 851-60, 2009). To evaluate the impact of 11β-HSD-1 inhibition on neuropathic pain, two animal models can be utilized: chronic constriction injury and the spinal nerve ligation rat models.

Chronic Constriction Injury (CCI) of Sciatic Nerve-Induced Neuropathic Pain

A model of chronic constriction of sciatic nerve injury-induced neuropathic pain in rats can be produced by following the method of Bennett and Xie (Bennett GJ, and Xie YK. Pain; 33(1): 87-107; 1988). The right common sciatic nerve is isolated at mid-thigh level, and loosely ligated by 4 chromic gut (4-0) ties separated by an interval of 1 mm. Sham rats undergo the same procedure, but without sciatic nerve constriction. All animals are allowed to recover for at least 2 weeks and no more than 5 weeks prior to testing of mechanical allodynia. Mechanical allodynia is measured using calibrated von Frey filaments (Stoelting, Wood Dale, Ill.) as previously described (Chaplan, S. R., et al., Journal of Neuroscience Methods, 53, 55-63 (1994). Rats are placed into inverted individual plastic containers (20×12.5×20 cm) on top of a suspended wire mesh grid, and acclimated to the test chambers for 20 min. The von Frey filaments are presented perpendicularly to the plantar surface of the selected hind paw, and then held in this position for approximately 8 sec with enough force to cause a slight bend in the filament. Positive responses include an abrupt withdrawal of the hind paw from the stimulus, or flinching behavior immediately following removal of the stimulus. A 50% paw withdrawal threshold (PWT) is determined using an up-down procedure (Dixon W. J., Annu Rev Pharmacol Toxicol, 20, 441-62 (1980)). Only rats with a PWT≤5.0 g are considered allodynia and utilized to test the analgesic activity of 11β-HSD-1 inhibitors. For efficacy evaluation, 11β-HSD-1 inhibitors will be dosed acutely and sub-chronically (7-10 days), 14 days following unilateral CCI, and effects on tactile allodynia will be evaluated at selected time points.

Spinal Nerve Ligation (SNL)-Induced Neuropathic Pain

Rats will receive unilateral ligation of the L5 and L6 spinal nerves as previously described (Kim SH, and Chung J. M., Pain, 50(3), 355-63 (1992). The left L5 and L6 spinal nerves of the rat are isolated adjacent to the vertebral column and tightly ligated with a 5-0 silk suture distal to the dorsal root ganglion, and care taken to avoid injury of the L4 spinal nerve. Sham rats will undergo the same procedure, but without nerve ligation. All animals are allowed to recover for at least 1 week and not more than 3 weeks prior to assessment of mechanical allodynia. Allodynic PWT is assessed in these animals in a manner similar to that described for CCI animals. Only rats with a PWT 5.0 g are considered allodynia and utilized to test the analgesic activity of 11β-HSD-1 inhibitors. For efficacy evaluation, 11β-HSD-1 inhibitors will be dosed acutely and sub-chronically (7-10 days), 14 days following unilateral SNL, and effects on tactile allodynia will be evaluated at selected time points.

Evaluation of Effects of 11β-HSD-1 Inhibitors in Chronic Inflammatory Models Using a Preventive vs. Established Therapeutic Regimen Glucocorticoids serve a protective role early in the inflammatory response, but may contribute to the disease process with chronic exposure. One way to evaluate this is to evaluate an 11β-HSD-1 inhibitor in rat adjuvant arthritis. Two protocols can be used. First, evaluate efficacy using a prophylactic dosing regimen (give inhibitor before arthritis is induced): Second, evaluate efficacy in an established model of rat adjuvant arthritis where the inflammatory component has subsided, and the disease has progressed to a more chronic, bone-injury model. In this case, high levels of endogenous glucocorticoids may prolong or exacerbate the disease, and 11β-HSD-1 inhibitors might prove to have a bone-sparing effect, and be more realistic of the human situation.

Therapeutic Compositions-Administration-Dose Ranges

Therapeutic compositions of the present compounds comprise an effective amount of the same formulated with one or more therapeutically suitable excipients. The term "therapeutically suitable excipient," as used herein, generally refers to pharmaceutically suitable, solid, semi-solid or liquid fillers, diluents, encapsulating material, formulation auxiliary and the like. Solid dosage forms for oral administration include, but are not limited to, capsules, tablets, gels, pills, powders, granules and the like. The drug compound is generally combined with at least one therapeutically suitable excipient, such as carriers, fillers, extenders, disintegrating agents, solution retarding agents, wetting agents, absorbents, lubricants and the like. Capsules, tablets, and pills may also contain buffering agents. Suppositories for rectal administration may be prepared by mixing the compounds with a suitable non-irritating excipient that is solid at ordinary temperature but fluid in the rectum. Examples of therapeutically suitable excipients include, but are not limited to, sugars, cellulose and derivatives thereof, oils, glycols, solutions, buffers, colorants, releasing agents, coating agents, sweetening agents, flavoring agents, perfuming agents, and the like. Such therapeutic compositions may be administered parenterally, intracisternally, orally, rectally, intraperitoneally or by other dosage forms known in the art.

The present drug compounds may also be microencapsulated with one or more excipients. Tablets, dragees, capsules, pills, and granules may also be prepared using coatings and shells, such as enteric and release or rate controlling polymeric and nonpolymeric materials. For example, the compounds may be mixed with one or more inert diluents. Tableting may further include lubricants and other processing aids. Similarly, capsules may contain opacifying agents that delay release of the compounds in the intestinal tract.

Liquid dosage forms for oral administration include, but are not limited to, emulsions, microemulsions, solutions, suspensions, syrups, and elixirs. Liquid dosage forms may also contain diluents, solubilizing agents, emulsifying agents, inert diluents, wetting agents, emulsifiers, sweeteners, flavorants, perfuming agents and the like.

Injectable preparations include, but are not limited to, sterile, injectable, aqueous, oleaginous solutions, suspensions, emulsions and the like. Such preparations may also be formulated to include, but are not limited to, parenterally suitable diluents, dispersing agents, wetting agents, suspending agents and the like. Such injectable preparations may be sterilized by filtration through a bacterial-retaining filter. Such preparations may also be formulated with sterilizing agents that dissolve or disperse in the injectable media or other methods known in the art.

Transdermal patches have the added advantage of providing controlled delivery of the present compounds to the body. Such dosage forms are prepared by dissolving or dispensing the compounds in suitable medium. Absorption enhancers may also be used to increase the flux of the compounds across the skin. The rate of absorption may be controlled by employing a rate controlling membrane. The compounds may also be incorporated into a polymer matrix or gel.

The absorption of the compounds of the present disclosure may be delayed using a liquid suspension of crystalline or amorphous material having poor water solubility. The rate of absorption of the compounds generally depends upon the rate of dissolution and crystallinity. Delayed absorption of a parenterally administered compound may also be accomplished by dissolving or suspending the compound in oil. Injectable depot dosage forms may also be prepared by microencapsulating the same in biodegradable polymers. The rate of drug release may also be controlled by adjusting the ratio of compound to polymer and the nature of the polymer employed. Depot injectable formulations may also prepared by encapsulating the compounds in liposomes or microemulsions compatible with body tissues.

For a given dosage form, disorders of the present disclosure may be treated, prophylatically treated, or have their onset delayed in a patient by administering to the patient a therapeutically effective amount of compound of the present disclosure in accordance with a suitable dosing regimen. In other words, a therapeutically effective amount of any one of compounds of formulas (I) is administered to a patient to treat and/or prophylatically treat disorders modulated by the 11-beta-hydroxysteroid dehydrogenase type 1 enzyme. The specific therapeutically effective dose level for a given patient population may depend upon a variety of factors including, but not limited to, the specific disorder being treated, the severity of the disorder; the activity of the compound, the specific composition or dosage form, age, body weight, general health, sex, diet of the patient, the time of administration, route of administration, rate of excretion, duration of the treatment, drugs used in combination, coincidental therapy and other factors known in the art.

The present disclosure also includes therapeutically suitable metabolites formed by in vivo biotransformation of any of the compounds of formula (I). The term "therapeutically suitable metabolite", as used herein, generally refers to a pharmaceutically active compound formed by the in vivo biotransformation of compounds of formula (I). For example, pharmaceutically active metabolites include, but are not limited to, compounds made by adamantane hydroxylation or polyhydroxylation of any of the compounds of formulas (I). A discussion of biotransformation is found in Goodman and Gilman's, The Pharmacological Basis of Therapeutics, seventh edition, MacMillan Publishing Company, New York, N.Y., (1985).

Administration and Dose Ranges

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula (I) are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula (I) are indicated, generally satisfactory results are obtained when the compounds of the present disclosure are administered at a daily dosage of from about 0.1 milligram to about 100 milligram per kilogram of animal body weight, given as a single daily dose or in divided doses about two to about six times a day, or in a sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

It is understood that the foregoing detailed description and accompanying examples are merely illustrative and are not to be taken as limitations upon the scope of the disclosure, which is defined solely by the appended claims and their equivalents. Various changes and modifications to the disclosed aspects will be apparent to those skilled in the art. Such changes and modifications, including without limitation those relating to the chemical structures, substituents, derivatives, intermediates, syntheses, formulations and/or methods of use of the disclosure, may be made without departing from the spirit and scope thereof.

All documents cited herein, and documents referenced or cited in documents cited herein, are hereby incorporated herein by reference.

What is claimed is:

1. A method for treating a patient suffering from chronic inflammation or neuropathic pain, comprising administering to the patient an effective amount of a selective inhibitor of 11-beta-hydroxysteroid dehydrogenase Type 1 enzyme activity, wherein the inhibitor is a compound of formula (I):

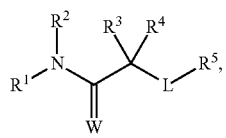

wherein
L is —(CH$_2$)$_n$;
n is independently at each occurrence 0, 1, or 2;
R$^1$ is adamantyl;
R$^2$ is hydrogen, alkyl, or aryl; or R$^2$ and R$^3$ together with the atoms to which they are attached form a heterocycle;
R$^3$ and R$^4$ are independently hydrogen or alkyl; or R$^3$ and R$^4$ together with the atom to which they are attached form a cycloalkyl or heterocycle;
R$^5$ is heterocycle, wherein the heterocycle contains at least one nitrogen atom;
and
W is N—CN, or O;
or a pharmaceutically acceptable salt thereof.

2. The method of claim 1, wherein the inhibitor shows an IC$_{50}$ value less than 200 nM.

3. The method of claim 1, wherein the inhibitor shows an IC$_{50}$ value less than 100 nM.

4. The method of claim 1, wherein the inhibitor shows an IC$_{50}$ value less than 10 nM.

5. The method of claim 1, wherein the inhibitor shows an IC$_{50}$ value less than 1 nM.

6. The method of claim 1, wherein the compound of formula (I) is selected from the group consisting of:
N—[(Z)-5-hydroxy-2-adamantyl]-2-{4-[5-(trifluoromethyl)pyridin-2-yl]piperazin-1-yl}acetamide;
N-[(E)-5-hydroxy-2-adamantyl]-2-{4-[5-(trifluoromethyl)pyridin-2-yl]piperazin-1-yl}acetamide;
N-[(E)-5-hydroxy-2-adamantyl]-2-{4-[5-(trifluoromethyl)pyridin-2-yl]piperazin-1-yl}propanamide;
2-[(cis)-2,6-dimethylmorpholin-4-yl]-N-[(E)-5-hydroxy-2-adamantyl]propanamide;
N—[(Z)-5-hydroxy-2-adamantyl]-2-(4-hydroxypiperidin-1-yl)propanamide;
N-[(E)-5-hydroxy-2-adamantyl]-2-(4-hydroxypiperidin-1-yl)propanamide;
2-azepan-1-yl-N-[(E)-5-hydroxy-2-adamantyl]propanamide;
(E)-4-[({4-[5-(trifluoromethyl)pyridin-2-yl]piperazin-1-yl}acetyl)amino]-1-adamantyl carbamate;
(E)-4-[(2-{4-[5-(trifluoromethyl)pyridin-2-yl]piperazin-1-yl}acetyl)amino]-1-adamantyl acetate;
N-[(E)-5-(acetylamino)-2-adamantyl]-2-{4-[5-(trifluoromethyl)pyridin-2-yl]piperazin-1-yl}acetamide;
N-[(E)-5-fluoro-2-adamantyl]-2-{4-[5-(trifluoromethyl)pyridin-2-yl]piperazin-1-yl}acetamide;
N—[(Z)-5-fluoro-2-adamantyl]-2-{4-[5-(trifluoromethyl)pyridin-2-yl]piperazin-1-yl}acetamide;
N-[(E)-5-hydroxy-2-adamantyl]-2-[4-(5-methylpyridin-2-yl)piperazin-1-yl]propanamide;
N-[(E)-5-hydroxy-2-adamantyl]-2-methyl-2-{4-[5-(trifluoromethyl)pyridin-2-yl]piperazin-1-yl}propanamide;
(E)-4-{2-methyl-2-[4-(5-trifluoromethyl-pyridin-2-yl)-piperazin-1-yl]-propionylamino}-adamantane-1-carboxylic acid;
(E)-4-({1-[4-(5-trifluoromethyl-pyridin-2-yl)-piperazin-1-yl]-cyclopropanecarbonyl}-amino)-adamantane-1-carboxylic acid;
(E)-4-({1-[4-(5-trifluoromethyl-pyridin-2-yl)-piperazin-1-yl]-cyclopropanecarbonyl}-amino)-adamantane-1-carboxyamide;
(E)-4-{2-[4-(5-trifluoromethyl-pyridin-2-yl)-piperazin-1-yl]-butyrylamino}-adamantane-1-carboxyamide;
(E)-4-{2-cyclopropyl-2-[4-(5-trifluoromethyl-pyridin-2-yl)-piperazin-1-yl]-acetylamino}-adamantane-1-carboxyamide;
(E)-4-({1-[4-(5-trifluoromethyl-pyridin-2-yl)-piperazin-1-yl]-cyclobutanecarbonyl}-amino)-adamantane-1-carboxamide;
(E)-N-(5-hydroxymethyl-adamantan-2-yl)-2-[4-(5-trifluoromethyl-pyridin-2-yl)-piperazin-1-yl]-isobutyramide;
(E)-N-(5-formyl-adamantan-2-yl)-2-[4-(5-trifluoromethyl-pyridin-2-yl)-piperazin-1-yl]-isobutyramide;
(E)-4-{2-methyl-2-[4-(5-trifluoromethyl-pyridin-2-yl)-piperazin-1-yl]-propionylamino}-adamantane-1-carboxyamide;
(E)-4-{2-methyl-2-[4-(5-trifluoromethyl-pyridin-2-yl)-piperazin-1-yl]-propionylamino}-adamantane-1-carboxylic acid hydroxyamide;
(E)-4-{2-[4-(5-trifluormethyl-pyridin-2-yl)-piperazin-1-yl]-acetylamino}-adamantane-1-carboxylic acid;
(E)-4-[2-(3,3-difluoro-piperidin-1-yl)-acetylamino]-adamantane-1-carboxylic acid;
(E)-4-[2-(2-trifluoromethyl-pyrrolidin-1-yl)-acetylamino]-adamantane-1-carboxylic acid;
(E)-4-{2-[4-(5-trifluoromethyl-pyridin-2-yl)-piperazin-1-yl]-acetylamino}-adamantane-1-carboxyamide;
(E)-4-[2-(2-trifluoromethyl-pyrrolidin-1-yl)-acetylamino]-adamantane-1-carboxyamide;
(E)-4-[2-(3,3-difluoro-piperidin-1-yl)-acetylamino]-adamantane-1-carboxyamide;
(E)-4-[2-(3-fluoropyaolidin-1-yl)-propionylamino]-adamantane-1-carboxyamide;
(E)-4-[2-(3,3-difluoropiperidine-1-yl)-propionylamino]-adamantane-1-carboxyamide;
(E)-4-[2-(2-trifluoromethylpyrrolidin-1-yl)-propionylamino]-adamantane-1-carboxyamide;
(E)-4-{2-[4-(5-chloro-pyridin-2-yl)-piperazin-1-yl]-2-methyl-propionylamino}-adamantane-1-carboxylic acid;
(E)-4-[2-methyl-2-(1,2,4,5-tetrahydro-benzo[d]azepin-3-yl)-propionylamino]-adamantane-1-carboxylic acid;
(E)-4-[2-methyl-2-(4-m-tolyl-[1,4]diazepan-1-yl)-propionylamino]-adamantane-1-carboxylic acid;
(E)-4-[2-methyl-2-(4-phenyl-piperidin-1-yl)-propionylamino]-adamantane-1-carboxylic acid;
(E)-4-{2-[4-(4-chloro-phenyl)-piperidin-1-yl]-2-methyl-propionylamino}-adamantane-1-carboxylic acid;
(E)-4-{2-[5-(6-chloro-pyridin-3-yl)-hexahydro-pyrrolo[3,4-c]pyrrol-2-yl]-2-methyl-propionylamino}-adamantane-1-carboxyamide;
(E)-4-{2-[4-(5-fluoro-pyridin-3-yl)-[1,4]diazepan-1-yl]-2-methyl-propionylamino}-adamantane-1-carboxyamide;
(E)-4-[2-methyl-2-(3-pyridin-3-yl-3,9-diazbicyclo[4.2.1]non-9-yl)-propionylamino]-adamantane-1-carboxyamide;
(E)-4-[2-methyl-2-(2-trifluoromethyl-pyrrolidin-1-yl)-propionylamino]-adamantane-1-carboxyamide;
(E)-4-[2-(3,3-difluoro-piperidin-1-yl)-2-methyl-propionylamino]-adamantane-1-carboxyamide;

(E)-4-[2-(3-fluoro-pyrrolidin-1-yl)-2-methyl-propionylamino]-adamantane-1-carboxyamide;
(E)-4-{2-[4-(5-Trifluormethyl-pyridin-2-yl)-piperazin-1-yl]-acetylamino}-adamantane-1-carboxamide;
(E)-4-[2-(3,3-difluoro-piperidin-1-yl)-2-methyl-propionylamino]-adamantane-1-carboxylic acid 3,4-dimethoxy-benzylamide;
(E)-4-[({4-[2-(3,3-difluoro-piperidin-1-yl)-2-methyl-propionylamino]-adamantane-1-carbonyl}-amino)-methyl]-benzoic acid;
(E)-4-[2-(3,3-difluoro-piperidin-1-yl)-2-methyl-propionylamino]-adamantane-1-carboxylic acid (furan-2-ylmethyl)-amide;
(E)-4-[2-(3,3-Difluoro-piperidin-1-yl)-2-methyl-propionylamino]-adamantane-1-carboxylic acid (thiazol-5-ylmethyl)-amide;
(E)-4-[2-(3,3-difluoro-piperidin-1-yl)-2-methyl-propionylamino]-adamantane-1-carboxylic acid 2-methoxybenzylamide;
(E)-4-(2-methyl-2-phenylamino-propionylamino)-adamantane-1-carboxyamide;
(E)-4-[2-methyl-2-(3-pyridin-3-yl-3,9-diazbicyclo[4.2.1]non-9-yl)-propionylamino]-adamantane-1-carboxyamide;
(E)-4-{2-methyl-2-[5-(3-trifluoromethyl-phenyl)-[1,5]diazocan-1-yl]-propionylamino}-adamantane-1-carboxylic acid;
(E)-4-{2-[7-(5-bromo-pyridin-2-yl)-3,7-diazbicyclo[3.3.1]non-3-yl]-2-methyl-propionylamino}-adamantane-1-carboxyamide;
2-(4-benzylpiperidin-1-yl)-N-[(E)-5-hydroxy-2-adamantyl]propanamide;
N-[(E)-5-hydroxy-2-adamantyl]-2-(6,7,9,10-tetrahydro-8H-[1,3]dioxolo[4,5-g][3]benzazepin-8-yl)propanamide;
N-[(E)-5-hydroxy-2-adamantyl]-2-(4-pyridin-2-ylpiperazin-1-yl)propanamide;
2-[4-(4-fluorophenyl)piperazin-1-yl]-N-[(E)-5-hydroxy-2-adamantyl]propanamide;
N-[(E)-5-hydroxy-2-adamantyl]-2-[4-(4-methoxyphenyl)piperazin-1-yl]propanamide;
2-[4-(5-cyanopyridin-2-yl)piperazin-1-yl]-N-[(E)-5-hydroxy-2-adamantyl]propanamide;
2-[4-(2-furoyl)piperazin-1-yl]-N-[(1R,3S)-5-hydroxy-2-adamantyl]propanamide;
2-(1,3-dihydro-2H-isoindol-2-yl)-N-[(E)-5-hydroxy-2-adamantyl]propanamide;
N-[(E)-5-hydroxy-2-adamantyl]-2-{4-[4-(trifluoromethyl)phenyl]piperazin-1-yl}propanamide;
(2S)—N-[(E)-5-hydroxy-2-adamantyl]-2-{4-[5-(trifluoromethyl)pyridin-2-yl]piperazin-1-yl}propanamide;
(2R)—N-[(E)-5-hydroxy-2-adamantyl]-2-{4-[5-(trifluoromethyl)pyridin-2-yl]piperazin-1-yl}propanamide;
2-[3-(4-chlorophenoxy)azetidin-1-yl]-N-[(E)-5-hydroxy-2-adamantyl]propanamide;
2-[4-(2-fluorophenoxy)piperidin-1-yl]-N-[(E)-5-hydroxy-2-adamantyl]propanamide;
2-[3-(2-fluorophenoxy)piperidin-1-yl]-N-[(E)-5-hydroxy-2-adamantyl]propanamide;
2-[3-(3-fluorophenoxy)pyrrolidin-1-yl]-N-[(E)-5-hydroxy-2-adamantyl]propanamide;
2-(5-chloro-2,3-dihydro-1H-indol-1-yl)-N-[(E)-5-hydroxy-2-adamantyl]propanamide;
2-[4-(6-chloropyridin-3-yl)piperazin-1-yl]-N-[(E)-5-hydroxy-2-adamantyl]propanamide;
N-[(E)-5-hydroxy-2-adamantyl]-2-(3-phenylazetidin-1-yl)propanamide;
(E)-N-methyl-4-[(2-methyl-2-{4-[5-(trifluoromethyl)pyridin-2-yl]piperazin-1-yl}propanoyl)amino]adamantane-1-carboxamide;
(E)-N-methoxy-4-[(2-methyl-2-{4-[5-(trifluoromethyl)pyridin-2-yl]piperazin-1-yl}propanoyl)amino]adamantane-1-carboxamide;
N-[(E)-5-(aminomethyl)-2-adamantyl]-2-methyl-2-{4-[5-(trifluoromethyl)pyridin-2-yl]piperazin-1-yl}propanamide;
N-[(E)-5-hydroxy-2-adamantyl]-1-piperidin-1-ylcyclopropanecarboxamide;
2-methyl-N-[(E)-5-(5-methyl-1,2,4-oxadiazol-3-yl)-2-adamantyl]-2-{4-[5-(trifluoromethyl)pyridin-2-yl]piperazin-1-yl}propanamide;
2-methyl-N-[(E)-5-(2H-tetraazol-5-yl)-2-adamantyl]-2-{4-[5-(trifluoromethyl)pyridin-2-yl]piperazin-1-yl}propanamide;
(E)-4-[(2-{4-[[(4-chlorophenyl)sulfonyl](cyclopropyl)amino]piperidin-1-yl}propanoyl)amino]adamantane-1-carboxamide;
N-[(E)-5-hydroxy-2-adamantyl]-2-methyl-2-[2-(trifluoromethyl)pyrrolidin-1-yl]propanamide;
(E)-4-({2-[(3S)-3-fluoropyrrolidin-1-yl]-2-methylpropanoyl}amino)adamantane-1-carboxamide;
methyl (E)-4-{[2-methyl-2-(4-pyridin-2-ylpiperazin-1-yl)propanoyl]amino}adamantane-1-carboxylate;
(E)-4-{[2-methyl-2-(4-pyridin-2-ylpiperazin-1-yl)propanoyl]amino}adamantane-1-carboxylic acid;
(E)-4-({2-methyl-2-[(2S)-2-methyl-4-pyridin-2-ylpiperazin-1-yl]propanoyl}amino)adamantane-1-carboxylic acid;
(E)-4-{[2-methyl-2-(4-pyridin-2-ylpiperazin-1-yl)propanoyl]amino}adamantane-1-carboxamide;
2-methyl-N-[(E)-5-(4H-1,2,4-triazol-3-yl)-2-adamantyl]-2-{4-[5-(trifluoromethyl)pyridin-2-yl]piperazin-1-yl}propanamide;
(E)-4-{[2-(3,3-difluoropiperidin-1-yl)-2-methylpropanoyl]amino}-N-(pyridin-4-ylmethyl)adamantane-1-carboxamide;
(E)-4-[(2-methyl-2-{4-[4-(trifluoromethyl)phenyl]piperazin-1-yl}propanoyl)amino]adamantane-1-carboxylic acid;
(E)-4-({2-methyl-2-[(2R)-2-methyl-4-(5-methylpyridin-2-yl)piperazin-1-yl]propanoyl}amino)adamantane-1-carboxylic acid;
(E)-4-({2-[(3S)-3-fluoropiperidin-1-yl]propanoyl}amino)adamantane-1-carboxamide;
(E)-4-[((2S)-2-{4-[5-(trifluoromethyl)pyridin-2-yl]piperazin-1-yl}propanoyl)amino]adamantine-1-carboxamide;
(E)-4-[((2R)-2-{4-[5-(trifluoromethyl)pyridin-2-yl]piperazin-1-yl}propanoyl)amino]adamantane-1-carboxamide;
(E)-4-[({2-(trifluoromethyl)-4-[5-(trifluoromethyl)pyridin-2-yl]piperazin-1-yl}acetyl)amino]adamantane-1-carboxamide;
(E)-4-[(cyclopropyl{4-[5-(trifluoromethyl)pyridin-2-yl]piperazin-1-yl}acetyl)amino]adamantane-1-carboxylic acid;
(E)-4-{[(1-{4-[5-(trifluoromethyl)pyridin-2-yl]piperazin-1-yl}cyclobutyl)carbonyl]amino}adamantane-1-carboxylic acid;
(E)-4-({2-[9-(6-Chloropyridin-3-yl)-3,9-diazabicyclo[4.2.1]non-3-yl]-2-methylpropanoyl}amino)adamantane-1-carboxamide;

(E)-4-({2-[4-(2,3-dichlorophenyl)piperazin-1-yl]-2-methylpropanoyl}amino)adamantane-1-carboxylic acid;
(E)-4-{[2-methyl-2-(4-phenylpiperazin-1-yl)propanoyl]amino}adamantane-1-carboxylic acid;
(E)-4-({2-methyl-2-[4-(4-methylphenyl)piperazin-1-yl]propanoyl}amino)adamantane-1-carboxylic acid;
(E)-4-({2-[4-(1,3-benzothiazol-2-yl)piperazin-1-yl]-2-methylpropanoyl}amino)adamantane-1-carboxylic acid;
(E)-4-({2-[4-(3,4-dichlorophenyl)piperazin-1-yl]-2-methylpropanoyl}amino)adamantane-1-carboxylic acid;
(E)-4-({2-methyl-2-[4-(3-methylphenyl)piperazin-1-yl]propanoyl}amino)adamantane-1-carboxylic acid;
(E)-4-[(2-methyl-2-{4-[2-(trifluoromethyl)phenyl]piperazin-1-yl}propanoyl)amino]adamantane-1-carboxylic acid;
(E)-4-({2-[4-(2,4-difluorophenyl)piperazin-1-yl]-2-methylpropanoyl}amino)adamantane-1-carboxylic acid;
(E)-4-({2-methyl-2-[4-(6-methylpyridin-2-yl)piperazin-1-yl]propanoyl}amino)adamantane-1-carboxylic acid;
(E)-4-{[2-methyl-2-(4-pyrimidin-2-ylpiperazin-1-yl)propanoyl]amino}adamantane-1-carboxylic acid;
(E)-4-({2-[4-(4-fluorophenyl)piperazin-1-yl]-2-methylpropanoyl}amino)adamantane-1-carboxylic acid;
(E)-4-[(2-methyl-2-{4-[3-(trifluoromethyl)phenyl]piperazin-1-yl}propanoyl)amino]adamantane-1-carboxylic acid;
(E)-4-[(2-methyl-2-{4-[3-(trifluoromethyl)pyridin-2-yl]piperazin-1-yl}propanoyl)amino]adamantane-1-carboxylic acid;
(E)-4-({2-[4-(3-chlorophenyl)piperazin-1-yl]-2-methylpropanoyl}amino)adamantane-1-carboxylic acid;
(E)-4-({2-[4-(4-acetylphenyl)piperazin-1-yl]-2-methylpropanoyl}amino)adamantane-1-carboxylic acid;
(E)-N,N-dimethyl-4-[(2-methyl-2-{4-[5-(trifluoromethyl)pyridin-2-yl]piperazin-1-yl}propanoyl)amino]adamantane-1-carboxamide;
N-[(E)-5-(acetylamino)-2-adamantyl]-2-{4-[5-(trifluoromethyl)pyridin-2-yl]piperazin-1-yl}propanamide;
(E)-4-{[2-methyl-2-(4-pyrimidin-2-ylpiperazin-1-yl)propanoyl]amino}adamantane-1-carboxamide;
(E)-4-{[2-methyl-2-(4-pyrazin-2-ylpiperazin-1-yl)propanoyl]amino}adamantane-1-carboxamide;
(E)-4-({2-[4-(4-fluorophenyl)piperazin-1-yl]-2-methylpropanoyl}amino)adamantane-1-carboxamide;
(E)-4-({2-[4-(3-cyanopyridin-2-yl)piperazin-1-yl]-2-methylpropanoyl}amino)adamantane-1-carboxamide;
(E)-4-({2-methyl-2-[4-(6-methylpyridin-3-yl)-1,4-diazepan-1-yl]propanoyl}amino) adamantane-1-carboxamide;
(E)-4-[(2-{4-[3-chloro-5-(trifluoromethyl)pyridin-2-yl]piperazin-1-yl}-2-methylpropanoyl)amino]adamantane-1-carboxylic acid;
4-(2-{[((E)-4-{[2-(3,3-difluoropiperidin-1-yl)-2-methylpropanoyl]amino}-1-adamantyl)carbonyl]amino}ethyl)benzoic acid;
N-{(E)-5-[(methylsulfonyl)amino]-2-adamantyl}-2-{4-[5-(trifluoromethyl)pyridin-2-yl]piperazin-1-yl}propanamide;
N-[(E)-5-(1-hydroxy-1-methylethyl)-2-adamantyl]-2-methyl-2-{4-[5-(trifluoromethyl)pyridin-2-yl]piperazin-1-yl}propanamide;
(E)-4-{[2-methyl-2-(4-phenylpiperazin-1-yl)propanoyl]amino}adamantane-1-carboxamide;
(E)-4-({2-[4-(2-methoxyphenyl)piperazin-1-yl]-2-methylpropanoyl}amino)adamantane-1-carboxamide;
(E)-4-({2-[4-(2,4-dimethoxyphenyl)piperazin-1-yl]-2-methylpropanoyl}amino)adamantane-1-carboxamide;
(E)-4-({2-[4-(2,3-dicyanophenyl)piperazin-1-yl]-2-methylpropanoyl}amino)adamantane-1-carboxamide;
N-[(E)-5-(cyanomethyl)-2-adamantyl]-2-methyl-2-{4-[5-(trifluoromethyl)pyridin-2-yl]piperazin-1-yl}propanamide;
(E)-4-({2-methyl-2-[4-(4-nitrophenyl)piperazin-1-yl]propanoyl}amino)adamantane-1-carboxylic acid;
(E)-4-({2-[4-(2,4-dichlorophenyl)piperazin-1-yl]-2-methylpropanoyl}amino)adamantane-1-carboxylic acid;
{(E)-4-[(2-methyl-2-{4-[5-(trifluoromethyl)pyridin-2-yl]piperazin-1-yl}propanoyl)amino]-1-adamantyl}acetic acid;
(E)-4-({2-[4-(4-chloro-2-fluorophenyl)piperazin-1-yl]-2-methylpropanoyl}amino) adamantane-1-carboxylic acid;
(E)-4-[(2-methyl-2-{4-[4-(trifluoromethyl)pyrimidin-2-yl]piperazin-1-yl}propanoyl)amino]adamantane-1-carboxylic acid;
(E)-4-({2-[4-(3-chloro-4-fluorophenyl)piperazin-1-yl]-2-methylpropanoyl}amino) adamantane-1-carboxylic acid;
(E)-4-({2-[4-(4-cyanophenyl)piperazin-1-yl]-2-methylpropanoyl}amino)adamantane-1-carboxylic acid;
(E)-4-({2-[4-(4-bromophenyl)piperazin-1-yl]-2-methylpropanoyl}amino)adamantane-1-carboxylic acid;
(E)-4-({2-[4-(5-chloro-2-methoxyphenyl)piperazin-1-yl]-2-methylpropanoyl}amino)adamantane-1-carboxylic acid;
(E)-4-({2-[4-(2-chlorophenyl)piperazin-1-yl]-2-methylpropanoyl}amino)adamantane-1-carboxylic acid;
(E)-4-({2-[4-(2-cyanophenyl)piperazin-1-yl]-2-methylpropanoyl}amino)adamantane-1-carboxylic acid;
(E)-4-({2-[4-(2-fluorophenyl)piperazin-1-yl]-2-methylpropanoyl}amino)adamantane-1-carboxylic acid;
(E)-4-({2-methyl-2-[4-(2-methylphenyl)piperazin-1-yl]propanoyl}amino)adamantane-1-carboxylic acid;
(E)-4-({2-[4-(4-chlorophenyl)piperazin-1-yl]-2-methylpropanoyl}amino)adamantane-1-carboxylic acid;
(E)-4-({2-[4-(3-chloropyridin-2-yl)piperazin-1-yl]-2-methylpropanoyl}amino)adamantane-1-carboxylic acid;
(E)-4-[(2-{4-[2-chloro-4-(trifluoromethyl)phenyl]piperazin-1-yl}-2-methylpropanoyl)amino]adamantane-1-carboxylic acid;
(E)-4-({2-[(3R)-3-fluoropyrrolidin-1-yl]-2-methylpropanoyl}amino)-N-(pyridin-3-ylmethyl)adamantane-1-carboxamide;
(E)-4-{[2-methyl-2-(3-phenylpiperidin-1-yl)propanoyl]amino}adamantane-1-carboxamide;

(E)-4-({2-[4-(2-chloro-4-methylphenyl)piperazin-1-yl]-2-methylpropanoyl}amino)adamantane-1-carboxylic acid;

(E)-4-({2-[4-(2-fluorophenyl)piperidin-1-yl]-2-methylpropanoyl}amino)adamantane-1-carboxylic acid;

(E)-4-({2-methyl-2-[4-(2-methylphenyl)piperidin-1-yl]propanoyl}amino)adamantane-1-carboxylic acid;

(E)-4-({2-[4-(2-chloro-4-fluorophenyl)piperazin-1-yl]-2-methylpropanoyl}amino) adamantane-1-carboxamide;

(E)-4-({2-[4-(2-furoyl)piperazin-1-yl]-2-methylpropanoyl}amino)adamantane-1-carboxylic acid;

(E)-4-({2-[4-(2-chloro-4-cyanophenyl)piperazin-1-yl]-2-methylpropanoyl}amino) adamantane-1-carboxylic acid;

(E)-4-({2-[4-(2-chloro-4-fluorophenyl)piperazin-1-yl]-2-methylpropanoyl}amino) adamantane-1-carboxylic acid;

(E)-4-[(2-methyl-2-{4-[5-(trifluoromethyl)pyridin-2-yl]piperazin-1-yl}propanoyl)amino]-1-adamantyl carbamate;

(E)-4-[(2-{4[(4-chlorophenyl)sulfonyl]piperazin-1-yl}-2-methylpropanoyl)amino]adamantane-1-carboxylic acid;

(E)-4-({2-[4-(2,4-difluorophenyl)piperidin-1-yl]-2-methylpropanoyl}amino)adamantane-1-carboxylic acid;

(E)-4-({2-[4-(4-cyano-2-fluorophenyl)piperazin-1-yl]-2-methylpropanoyl}amino) adamantane-1-carboxylic acid;

(E)-4-[(2-methyl-2-{3-methyl-4-[5-(trifluoromethyl)pyridin-2-yl]piperazin-1-yl}propanoyl)amino]adamantane-1-carboxylic acid;

tert-butyl 4-(2-{[(E)-5-(aminocarbonyl)-2-adamantyl]amino}-1,1-dimethyl-2-oxoethyl)piperazine-1-carboxylate;

(2R)-2-[(3R)-3-fluoropyrrolidin-1-yl]-N-[(E)-5-hydroxy-2-adamantyl]propanamide;

(E)-4-({2-[4-(2-bromophenyl)piperazin-1-yl]-2-methylpropanoyl}amino)adamantane-1-carboxylic acid;

(E)-4-({2-[4-(6-chloropyrimidin-4-yl)piperazin-1-yl]-2-methylpropanoyl}amino)adamantane-1-carboxylic acid;

(E)-4-({2-[4-(6-chloropyridazin-3-yl)piperazin-1-yl]-2-methylpropanoyl}amino)adamantane-1-carboxylic acid;

(E)-4-({2-[4-(2-chloropyrimidin-4-yl)piperazin-1-yl]-2-methylpropanoyl}amino)adamantane-1-carboxylic acid;

N-[({(E)-4-[(2-methyl-2-{4-[5-(trifluoromethyl)pyridin-2-yl]piperazin-1-yl}propanoyl)amino]-1-adamantyl}amino)carbonyl]glycine;

(E)-4-({2-[4-(5-cyanopyridin-2-yl)piperazin-1-yl]-2-methylpropanoyl}amino)adamantane-1-carboxylic acid;

(E)-4-({2-[4-(3-chloro-5-cyanopyridin-2-yl)piperazin-1-yl]-2-methylpropanoyl}amino)adamantane-1-carboxylic acid;

(E)-4-({2-methyl-2-[4-(1,3-thiazol-2-yl)piperazin-1-yl]propanoyl}amino)adamantane-1-carboxylic acid;

(E)-4-({2-[4-(2-hydroxyphenyl)piperazin-1-yl]-2-methylpropanoyl}amino)adamantane-1-carboxylic acid;

4-(2-{[(E)-5-(aminocarbonyl)-2-adamantyl]amino}-1,1-dimethyl-2-oxoethyl)-N-(tert-butyl)piperazine-1-carboxamide;

N-[(E)-5-(formylamino)-2-adamantyl]-2-methyl-2-{4-[5-(trifluoromethyl)pyridin-2-yl]piperazin-1-yl}propanamide;

or a pharmaceutically acceptable salt thereof.

7. The method as in claim 1, wherein the pain is central neuropathic pain or peripheral neuropathic pain.

8. The method as in claim 1, wherein the method is for treating neuropathic pain.

* * * * *